(12) United States Patent
Nair et al.

(10) Patent No.: US 8,703,801 B2
(45) Date of Patent: Apr. 22, 2014

(54) PYRIDINONE HYDROXYCYCLOPENTYL CARBOXAMIDES: HIV INTEGRASE INHIBITORS WITH THERAPEUTIC APPLICATIONS

(75) Inventors: Vasu Nair, Athens, GA (US); Maurice O. Okello, Athens, GA (US); Abdumalik A. Nishonov, Boulder, CO (US); Sanjaykumar Mishra, Pune (IN)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/513,448

(22) PCT Filed: Dec. 7, 2010

(86) PCT No.: PCT/US2010/059183
§ 371 (c)(1),
(2), (4) Date: Jul. 26, 2012

(87) PCT Pub. No.: WO2011/071849
PCT Pub. Date: Jun. 16, 2011

(65) Prior Publication Data
US 2012/0282218 A1 Nov. 8, 2012

Related U.S. Application Data

(60) Provisional application No. 61/320,429, filed on Apr. 2, 2010, provisional application No. 61/283,675, filed on Dec. 7, 2009.

(51) Int. Cl.
C07D 213/64 (2006.01)
C07D 401/12 (2006.01)
A61K 31/44 (2006.01)

(52) U.S. Cl.
USPC ......... 514/343; 514/346; 546/278.4; 546/291

(58) Field of Classification Search
None
See application file for complete search history.

(56) References Cited

U.S. PATENT DOCUMENTS

| | | | |
|---|---|---|---|
| 7,098,201 B2 | 8/2006 | Fujishita et al. |
| 2003/0171406 A1 | 9/2003 | Sato |
| 2005/0261322 A1 | 11/2005 | Naidu et al. |
| 2006/0084665 A1 | 4/2006 | Satoh et al. |
| 2006/0122205 A1 | 6/2006 | Belyk et al. |
| 2006/0172973 A1 | 8/2006 | Nair et al. |
| 2006/0199956 A1 | 9/2006 | Naidu et al. |
| 2006/0217413 A1 | 9/2006 | Satoh et al. |
| 2007/0249687 A1 | 10/2007 | Yoshida |
| 2008/0020010 A1 | 1/2008 | Nair et al. |

FOREIGN PATENT DOCUMENTS

| | | |
|---|---|---|
| WO | 9962513 A1 | 12/1999 |
| WO | 9962520 A1 | 12/1999 |
| WO | 9962897 A1 | 12/1999 |
| WO | 0100578 A1 | 1/2001 |
| WO | 0230426 A1 | 4/2002 |
| WO | 035077 A1 | 5/2003 |
| WO | 2005113509 A1 | 12/2005 |
| WO | 2005115398 A2 | 12/2005 |
| WO | 2005118593 A1 | 12/2005 |
| WO | 2006027694 A1 | 3/2006 |
| WO | 2006060712 A2 | 6/2006 |
| WO | 2007106450 A2 | 9/2007 |
| WO | 2008010953 A2 | 1/2008 |
| WO | 2011071849 A2 | 6/2011 |

OTHER PUBLICATIONS

Katz R.A, Skalka A.M. The Retroviral Enzymes. Annu Rev Biochem, 1994;63;133-173.
Frankel A.D, YoungJ.A.T. HIV-1: Fifteen proteins and an RNA. Annu Rev Biochem 1998:67:1-25.
Johnson S.C, Gerber J.G. Advances in HIV/AIDS therapy. Advances in Internal Medicine, 2000:44;1-40.
De Clercq E. Strategies in the design of antiviral drugs. Nat. Rev. Drug Discovery, 2002:1(1);13-25.
Asante-Appiah E. Skalka A.M. HIV-1 integrase: Structural organization, conformational changes, and catalysis. Adv.Virus Res, 1999:52;351-369.
Nair V. Antiviral isonucleosides: discovery, chemistry and chemical biology. In Recent Adv. Nucleosides, Chu, C. K., Ed. Elsevier Science B.V. Amsterdam, Neth: 2002; pp. 149-166.
Miller M.D, Hazuda D.J. New antiretroviral agents: looking beyond protease and reverse transcriptase. Current Opinion in Microbiology, 2001:4(5);535-539.
Nair V. HIV integrase as a target for antiviral chemotherapy. Reviews in Medical Virology, 2002:12(3);179-193.
Nair V, CHI G. HIV integrase inhibitors as therapeutic agents in AIDS. Reviews in Medical Virology, 2007:17 (4);277-295.

(Continued)

*Primary Examiner* — Zinna Northington Davis
(74) *Attorney, Agent, or Firm* — Henry D. Coleman; R. Neil Sudol

(57) ABSTRACT

New chiral and achiral oxy-substituted cyclopentyl pyridinone diketocarboxamides and their derivatives and methods for their preparations are disclosed. The compounds include tautomers, regioisomers and geometric isomers. These complex carboxamides are designed as inhibitors of HIV replication through inhibition of HIV integrase. The compounds are useful in the prevention or treatment of infection by HIV and in the treatment of AIDS and ARC, either as the compounds, or as pharmaceutically acceptable salts, with pharmaceutically acceptable carriers, used alone or in combination with antivirals, immunomodulators, antibiotics, vaccines, and other therapeutic agents, especially other anti-HIV compounds (including other anti-HIV integrase agents), which can be used to create combination anti-HIV cocktails. Methods of treating AIDS and ARC and methods of treating or preventing infection by HIV are also described.

45 Claims, No Drawings

(56) References Cited

OTHER PUBLICATIONS

Nair V. Novel inhibitors of HIV integrase: The discovery of potential anti-HIV therapeutic agents. Current Pharmaceutical Design, 2003:9(31);2553-2565.
Pommier Y, Johnson A.A, Marchand C. Integrase inhibitors to treat HIV/Aids. Nat. Rev. Drug Discovery, 2005:4 (3);236-248.
Summa V, et al. Discovery of Raltegravir, a Potent, Selective Orally Bioavailable HIV-Integrase Inhibitor for the Treatment of HIV-Aids Infection. J. Med. Chem, 2008:51(18);5843-5855.
Egbertson M.S. HIV integrase inhibitors: from diketoacids to heterocyclic templates: a history of HIV integrase medicinal chemistry at merck west point and merck rome (IRBM). Curr. Top. Med. Chem. (Sharjah, United Arab Emirates) 2007:7(13);1251-1272.
Wai J.S, et al. 4-Aryl-2,4-dioxobutanoic Acid Inhibitors of HIV-1 Integrase and Viral Replication in Cells. J. Med. Chem. 2000:43(26);4923-4926.
Pais G.C.G, et al. Structure Activity of 3-Aryl-1,3-diketo-Containing Compounds as HIV-1 Integrase Inhibitors. J. Med. Chem, 2002:45(15);3184-3194.
Sechi M, et al. Design and Synthesis of Novel Indole $I^2$-Diketo Acid Derivatives as HIV-1 Integrase Inhibitors. J. Med. Chem, 2004:47(21);5298-5310.
Nair V, Chi G, Ptak R, Neamati N. HIV integrase inhibitors with nucleobase scaffolds: Discovery of a highly potent anti-HIV agent. J. Med. Chem, 2006:49(2);445-447.
Nair V, Chi G, Cox A, Ptak R, Neamati N. Conceptually novel HIV integrase inhibitors with nucleobase scaffolds: Discovery of a highly potent anti-HIV agent. Antiviral Research, 2006:70(1);A26-A26.
Uchil V, Seo B, Nair V. A novel strategy to assemble the beta-diketo acid pharmacophore of HIV integrase inhibitors on purine nucleobase scaffolds. Journal of Organic Chemistry, 2007:72(22);8577-8579.
Sato M, et al. Novel HIV-1 Integrase Inhibitors Derived from Quinolone Antibiotics. J. Med. Chem, 2006:49(5); 1506-1508.
Garvey E.P, et al. The naphthyridinone GSK364735 is a novel, potent human immunodeficiency virus type 1 integrase inhibitor and antiretroviral. Antimicrob. Agents Chemother, 2008:52(3);901-908.
Min S, et al. Pharmacokinetics (PK) and Safety in Healthy and HIV-Infected Subjects and Short-Term Antiviral Efficacy of S/GSK1265744, a Next Generation Once Daily HIV Integrase Inhibitor. Abstracts of the Interscience Conference on Antimicrobial Agents and Chemotherapy, 2009:49;249.
Xu L, et al. A Novel Pharmacoenhancer without Anti-HIV Activity. Abstracts of the Interscience Conference on Antimicrobial Agents and Chemotherapy, 2009:49;248.
Min S, et al. Pharmacokinetics and Safety of S/GSK1349572, a Next-Generation HIV Integrase Inhibitor, in Healthy Volunteers. Antimicrob. Agents Chemother, 2010:54(1);254-258.
Johns B, et al. "Discovery of S/GSK1349572: a once-daily next generation integrase inhibitor with a superior resistance profile," 17th CROI, 2010; Abstract No. 55, p. 86.
Cohen C, et al. "Single-tablet, fixed-dose regimen of elvitegravir/emtricitabine/tenofovir disoproxil furriarate/GS-9350 achieves a high rate of virologic suppression and GS-9350 is an effective booster," 17th CROI, 2010: Abstract No. 58LB, p. 87.
Nair V, et al. New Pyridinone Diketo Acid Inhibitors of HIV-1 Integrase: Anti-HIV Data, SAR Analysis, Microsome Stability, Cytochrome P450 Studies and Rodent Pharmacokinetics. Abstracts of the Interscience Conference on Antimicrobial Agents and Chemotherapy 2009, 49, 211.
Nair V, Uchil V, Neamati N. beta-Diketo acids with purine nucleobase scaffolds: Novel, selective inhibitors of the strand transfer step of HIV integrase. Bioorganic & Medicinal Chemistry Letters, 2006:16(7);1920-1923.
Chi G.C, Nair V, Semenova E, Pommier Y. A novel diketo phosphonic acid that exhibits specific, strand-transfer inhibition of HIV integrase and anti-HIV activity. Bioorganic & Medicinal Chemistry Letters, 2007:17(5);1266-1269.
Connolly T.P, et al. Novel spirocyclobutyl- and spirocyclooxetanyl-pyrimidin-6-oxa-5-hydroxy-4- carboxybenzylamides as potent HIV-1 integrase inhibitors. Abstr. Pap. Am. Chem. Soc, 2010:240;137-Medi.
Li C, et al. Design, synthesis and SAR study of novel Spiro azapyrimidinone HIV integrase inhibitors. Abstr. Pap. Am. Chem. Soc, 2010:240;134-Medi.
Naidu B.N, et al. Synthesis and HIV-1 integrase inhibitory activity of C2-C-linked heterocyclic-5-hydroxy-6-oxo dihydropyrimidine-4-carboxamides. Abstr. Pap. Am. Chem. Soc, 2010:240;130-Medi.
Sorenson M, et al. Study of C2-N-linked heterocyclic pyrimidin-6-oxa-5-hydroxy-4-carboxamide derivatives as HIV integrase inhibitors. Abstr. Pap. Am. Chem. Soc, 2010:240;133-Medi.
Walker M.A, et al. Discovery and preclinical evaluation of the HIV integrase inhibitor BMS-727740. Abstr. Pap. Am. Chem. Soc, 2010:240;135-Medi.
Charpentier C, et al. In vitro phenotypic susceptibility of HIV-2 clinical isolates to the integrase inhibitor S/ GSK1349572. Antiviral Ther, 2010:15;A58-A58.
Crosby D.C, et al. Design, Synthesis, and Biological Evaluation of Novel Hybrid Dicaffeoyltartaric/Diketo Acid and Tetrazole-Substituted L-Chicoric Acid Analogue Inhibitors of Human Inmmunodeficiency Virus Type 1 Integrase. J. Med. Chem, 2010:53(22);8161-8175.
Ferrara M, Fiore F, Summa V, Gardelli C. Development of 2-pyrrolidinyl-N-methyl pyrimidones as potent and orally bioavailable HIV integrase inhibitors. Bioorg. Med. Chem. Lett, 2010:20(17);5031-5034.
Ferro S, et al New chloro, fluorobenzylindole derivatives as integrase strand-transfer inhibitors (INSTIs) and their mode of action. Bioorg. Med. Chem. 2010:18(15);5510-5518.
Hadi V, et al. Development of the next generation of HIV-1 integrase inhibitors: Pyrazolone as a novel inhibitor scaffold. Bioorg. Med. Chem. Lett. 2010:20(22);6854-6857.
Hayouka Z, et al. Cyclic peptide inhibitors of HIV-1 integrase derived from the LEDGF/p75 protein. Bioorg. Med. Chem. 2010:18(23);8388-8395.
Johns B.A. HIV-1 Integrase Strand Transfer Inhibitors. Annu Rep Med Chem 2010:45;263-276.
Jones E.D, et al. Design of a series of bicyclic HIV-1 integrase inhibitors. Part 1: Selection of the scaffold. Bioorg. Med. Chem. Lett. 2010:20(19);5913-5917.
Le G.A, et al. Discovery of potent HIV integrase inhibitors active against raltegravir resistant viruses. Bioorg. Med. Chem. Lett. 2010:20(17);5013-5018.
Le G.A, Design of a series of bicyclic HIV-1 integrase inhibitors. Part 2: Azoles: Effective metal chelators. Bioorg. Med. Chem. Lett. 2010:20(19);5909-5912.
Li B.J, Chiang C.C, Hsu L.Y. QSAR Studies of 3,3 '-(Substituted-benzylidene)-bis-4-hydroxycoumarin, Potential HIV-1 Integrase Inhibitor. J. Chin. Chem. Soc. 2010:57(4A);742-749.
Luo Z.G, Tan J.J, Zeng Y, Wang C.X, Hu L.M. Development of Integrase Inhibitors of Quinolone Acid Derivatives for Treatment of AIDS: An Overview. Mini-Rev. Med. Chem. 2010;10(11):1046-1057.
Maes M et al. Peptide inhibitors of HIV-1 integrase: from mechanistic studies to improved lead compounds. J. Pept. Sci. 2010:16;163-163.
Maurin C, et al. New 2-arylnaphthalenediols and triol inhibitors of HIV-1 integrase-Discovery of a new polyhydroxylated antiviral agent. Bioorg. Med. Chem. 2010:18(14);5194-5201.
Mouscadet J.F, Desmaele D. Chemistry and Structure-Activity Relationship of the Styrylquinoline-Type HIV integrase Inhibitors. Molecules 2010, 15(5), 3048-3078.
Northfield E, et al. Modified Cyclic Peptides as Inhibitors of HIV-1 Integrase Activity. J. Pept. Sci. 2010:16; 130-130.
Ramkumar K, et al. Design, Synthesis and Structure-activity Studies of Rhodanine Derivatives as HIV-1 Integrase Inhibitors. Molecules 2010:15(6);3958-3992.
Selvam P, Chandramohan M, Prabhu N .S, Humar M.S. Design, Molecular Modelling Studies on Isatin Analogues as Novel Inhibitors of HIV Integrase. Antiviral Res. 2010:86(1);A45-A45.

(56) References Cited

OTHER PUBLICATIONS

Suzuki S, et al. Peptide HIV-1 Integrase Inhibitors from HIV-1 Gene Products. J. Med. Chem. 2010:53(14); 5356-5360.
Tanis S.P, et al. Azaindole N-methyl hydroxamic acids as HIV-1 integrase inhibitors-II. The impact of physicochemical properties on ADME and PK. Bioorg. Med. Chem. Lett. 2010:20(24);7429-7434.
Vandekerckhove L. GSK-1349572, a novel integrase inhibitor for the treatment of HIV infection. Curr. Opin. Investig. Drugs 2010:11(2);203-212.
Yang L.F, et al. Synthesis of polyhydroxylated aromatics having amidation of piperazine nitrogen as HIV-1 integrase inhibitor. Bioorg. Med. Chem. Lett. 2010:20(18);5469-5471.
Yoshinaga T, Kanamori-Koyama M, Seki T, Sato A, Fujiwara T. Strong inhibition of wild-type and integrase inhibitor (INI)—resistant HIV integrase (IN) strand transfer reaction by the novel INI S/GSK1349572. Antiviral Ther. 2010:15;A12-A12.
Yu S.H, Zhao S.T, Liu C, Zhong Y, Zhao G.S. Synthesis and HIV-1 Integrase Inhibitory Activity of Furanone Derivatives. Chem. Res. Chin. Univ. 2010:26(2);225-229.
Zatsepin T, Korolev S, Smolov M, Gottikh M, Agapkina J. Novel allosteric inhibitors of HIV-1 integrase on the base of multimodified oligonucleotides. Febs J. 2010:277;94-94.
Zolopa A.R, et al. Activity of Elvitegravir, a Once-Daily Integrase Inhibitor, against Resistant HIV Type 1: Results of a Phase 2, Randomized, Controlled, Dose-Ranging Clinical Trial. J. Infect. Dis. 2010:201(6);814-822.
Agapkina J, Zatsepin T, Knyazhanskaya E, Mouscadet J.F, Gottikh M. Structure-Activity Relationship Studies of HIV-1 Integrase Oligonucleotide Inhibitors. ACS Med. Chem. Lett. 2011:2(7);532-537.
Billamboz M, et al. 2-Hydroxyisoquinoline-1,3(2H,4H)-diones as inhibitors of HIV-1 integrase and reverse transcriptase RNase H domain: Influence of the alkylation of position 4. Eur. J. Med. Chem. 2011:46(2);535-546.
Billamboz M, et al. Magnesium Chelating 2-Hydroxyisoquinoline-1,3(2H,4H)-diones, as Inhibitors of HIV-1 Integrase and/or the HIV-1 Reverse Transcriptase Ribonuclease H Domain: Discovery of a Novel Selective Inhibitor of the Ribonuclease H Function. J. Med. Chem. 2011:54(6);1812-1824.
Bodiwala H.S, et al. Design and synthesis of caffeoyl-anilides as portmanteau inhibitors f HIV-1 integrase and CCR5. Bioorg. Med. Chem. 2011:19(3);1256-1263.
Cotelle P. 3-Hydroxy-6,7-dihydropyrimido [2,1-c][1,4]oxazin-4(9H)-ones as new HIV-1 integrase inhibitors WO2011046873 A1. Expert Opin. Ther. Pat. 2011:21(11);1799-1804.
De Luca L, et al. 4-[1-(4-Fluorobenzyl)-4-hydroxy-1H-indo1-3-yl]-2-hydroxy-4-oxobut-2-enoic acid as a prototype to develop dual inhibitors of HIV-1 integration process. Antiviral Res. 2011:92(1);102-107.
Di Santo R. Diketo Acids Derivatives as Dual Inhibitors of Human Immunodeficiency Virus Type 1 Integrase and the Reverse Transcriptase RNase H Domain. Curr. Med. Chem. 2011:18(22);3335-3342.
Elyakova L.A, Vaskovsky B.V, Khoroshilova N.I, Vantseva S.I, Agapkina Y.Y. Isolation and structure of a novel peptide inhibitor of HIV-1 integrase from marine polychaetes. Russ. J. Bioorg. Chem. 2011:37(2);207-216.
Fan X, et al. Design of HIV-1 integrase inhibitors targeting the catalytic domain as well as its interaction with LEDGF/ p75: A scaffold hopping approach using salicylate and catechol groups. Bioorg. Med. Chem. 2011:19(16);4935-4952.
Hare S, et al. Structural and Functional Analyses of the Second-Generation Integrase Strand Transfer Inhibitor Dolutegravir (S/GSK1349572). Mol. Pharmacol. 2011:80(4);565-572.
He Q.Q, et al. Synthesis and biological evaluation of HQCAs with aryl or benzyl substituents on N-1 position as potential HIV-1 integrase inhibitors. Bioorg. Med. Chem. 2011:19(18);5553-5558.
Hewer R, Traut T, Williams B, Coates J. The Design and Synthesis of Pyrolle-Carbaldehydes as HIV-1 Integrase Strand-Transfer Inhibitors. Antiviral Res. 2011:90(2);A50-A50.
Tomberlin G.H, et al. Dolutegravir (S/GSK1349572) Exhibits Significantly Slower Dissociation than Raltegravir and Elvitegravir from Wild-Type and Integrase Inhibitor-Resistant HIV-1 Integrase-DNA Complexes. Antimicrob. Agents Chemother. 2011:55(10):4552-4559.
Johnson T.W, et al. Design and Synthesis of Novel N-Hydroxy-Dihydronaphthyridinones as Potent and Orally Bioavailable HIV-1 Integrase Inhibitors. J. Med. Chem. 2011:54(9);3393-3417.
Kobayashi M, et al. In Vitro Antiretroviral Properties of S/GSK1349572, a Next-Generation HIV Integrase Inhibitor. Antimicrob. Agents Chemother. 2011:55(2);813-821.
Lenz J.C.C, Rockstroh J.K. S/GSK1349572, a new integrase inhibitor for the treatment of HIV: promises and challenges. Expert Opin. Invest. Drugs 2011:20(4):537-548.
Ma K.Q, et al. Rational design of 2-pyrrolinones as inhibitors of HIV-1 integrase. Bioorg. Med. Chem. Lett. 2011:21 (22);6724-6727.
Mukundan V.T, Do N.Q, Phan A.T. HIV-1 integrase inhibitor T30177 forms a stacked dimeric G-quadruplex structure containing bulges. Nucleic Acids Res. 2011:39(20);8984-8991.
Nagasawa J.Y, et al. 6-Benzylamino 4-oxo-1,4-dihydro-1,8-naphthyridines and 4-oxo-1,4-dihydroquinolines as HIV integrase inhibitors. Bioorg. Med. Chem. Lett. 2011:21(2);760-763.
Patel P, et al. Pharmacokinetics of the HIV integrase inhibitor S/GSK1349572 co-administered with acid-reducing agents and multivitamins in healthy volunteers. J. Antimicrob. Chemother. 2011:66(7);1567-1572.
Platts M.Y, et al. A concise synthesis of HIV integrase inhibitors bearing the dipyridone acid motif. Tetrahedron Lett. 2011:52(4);512-514.
Tang J, et al. 6-Benzoyl-3-hydroxypyrimidine-2,4-diones as dual inhibitors of HIV reverse transcriptase and integrase. Bioorg. Med. Chem. Lett. 2011:21(8);2400-2402.
Tang J, et al. N-3 Hydroxylation of Pyrimidine-2,4-diones Yields Dual Inhibitors of HIV Reverse Transcriptase and Integrase. ACS Med. Chem. Lett. 2011:2(1);63-67.
Tang J, et al. 3-Hydroxypyrimidine-2,4-diones as an Inhibitor Scaffold of HIV Integrase. J. Med. Chem. 2011:54(7); 2282-2292.
Wagstaff K, Rawlinson S, Hearps A, Jans D. Novel Inhibitors of Nuclear Translocation of HIV-1 Integrase. Antiviral Res. 2011:90(2);A48-A48.
Zatsepin T, Agapkina J, Korolev S, Gottikh M. Oligonucleotide Conjugates as Inhibitors of HIV-1 Integrase and Reverse Transcriptase. Nucl. Acid Ther. 2011:21(5);A31-A31.
Zhao X.Z, et al. Development of tricyclic hydroxy-1H-pyrrolopyridine-trione containing HIV-1 integrase inhibitors. Bioorg. Med. Chem. Lett. 2011:21(10);2986-2990.
Hu L.M, et al. Design and synthesis of novel beta-diketo derivatives as HIV-1 integrase inhibitors. Bioorg. Med. Chem. 2012:20(1);177-182.
Jain S.V, Sonawane L.V, Patil R.R, Bari S.B. Pharmacophore modeling of some novel indole beta-diketo acid and coumarin-based derivatives as HIV integrase inhibitors. Med. Chem. Res. 2012:21(2);165-173.
Kulkarni R, et al. The combined anti-HIV-1 activity of emtricitabine and tenofovir with the integrase inhibitors elvitegravir or raltegravir show high levels of synergy in vitro. HIV Med. 2012:13;29-29.
Zhao X.Z, Maddali K, Metifiot M, Smith S.J, Vu B.C. Bicyclic Hydroxy-1H-pyrrolopyridine-trione Containing HIV-1 Integrase Inhibitors. Chem. Biol. Drug Des. 2012:79(2);157-165.

PYRIDINONE HYDROXYCYCLOPENTYL CARBOXAMIDES: HIV INTEGRASE INHIBITORS WITH THERAPEUTIC APPLICATIONS

RELATED APPLICATIONS AND GRANT SUPPORT

The present application claims the benefit of priority from international patent application no. PCT/US2010/059183 filed Dec. 7, 2010, of which the present application is a United States national phase application; said international application claims the benefit of priority from provisional applications Ser. No. 61/283,675, filed Dec. 7, 2009 and US61/320, 429, filed Apr. 2, 2010, of identical title, the entirety of which applications are incorporated by reference herein.

The present invention was made with government support under Grant Number RO1 AI 43181 of the National Institutes of Health. Consequently, the government retains rights in the invention.

FIELD OF THE INVENTION

The present invention relates to the field of antiviral therapy, in particular the treatment of HIV infections in humans, preferably in combination therapy.

BACKGROUND OF THE INVENTION

The human immunodeficiency virus, HIV, encodes three key viral enzymes through its pol gene and these enzymes are critical for the replication of this virus [Katz & Skalka, Annu. Rev. Biochem., 63, 133-173 (1994); Frankel, Annu. Rev. Biochem., 67, 1-25 (1998)]. Drug discovery involving two of these enzymes, HIV reverse transcriptase (RT) and HIV protease (PR), have led to clinically approved therapeutic agents for the treatment of acquired immunodeficiency syndrome (AIDS) and AIDS related complex (ARC) in HAART (highly-active antiretroviral therapy) [Johnson & Gerber, in "Advances in Internal Medicine," vol. 44. Mosby: St. Louis, 1-40 (2000); De Clercq, Nature Reviews: Drug Discovery, 11, 13-25 (2002); Asante-Appiah & Skalka, Adv. Virus Res., 52, 351-369 (1999); Nair, in "Recent Advances in Nucleosides: Chemistry and Chemotherapy," Elsevier Science: Netherlands, 149-166 (2002)]. However, the third enzyme of the pol gene, HIV integrase, has received less consideration [Miller & Hazuda, Current Opinion in Microbiology, 4, 535-539 (2001); Nair, Rev. Med. Virol., 12, 179-193 (2002); Nair, Rev. Med. Virol., 17, 277-295 (2007); Nair, Current Pharmaceutical Design, 9, 2553-2565 (2003); Pommier, et al., Nature Rev. Drug Discovery 4, 236-248 (2005)]. At present there is only one integrase inhibitor (Raltegravir, Isentress) that is approved for clinical use for HIV/AIDS [J. Med. Chem. 51, 5843-5855 (2008); US Patent Publ. No. 2006/0122205 A1, NDA Report 22-145, Sep. 5, 2007]. HIV-1 integrase is involved in the integration of HIV DNA into human chromosomal DNA. Because integrase has no human counterpart and because it is required for HIV replication, it is an attractive target for the discovery of anti-HIV agents.

A variety of compounds are inhibitors of HIV integrase including oligonucleotides, dinucleotides, heterocycles, natural products, diketo acids, functionalized naphthyridines and pyrimidines and others [Nair, Rev. Med. Virol., 17, 277-295 (2007); Egbertson, Curr. Top. Med. Chem. 7, 1251-1272 (2007)]. Some diketo acids with aryl or heteroaryl substitutions are inhibitors of HIV integrase, but most commonly of only the strand transfer step [Wai, et al., "4-Aryl-2,4-dioxobutanoic acid inhibitors of HIV-1 integrase and viral replication in cells," J. Med. Chem. 43, 4923-4926 (2000); Pais, G. C. G., et al., "Structure activity of 3-aryl-1,3-diketo-containing compounds as HIV-1 integrase inhibitors," J. Med. Chem. 45, 3184-3194 (2002); Sechi, M., et al., "Design and synthesis of novel indole beta-diketo acid derivatives as HIV-1 integrase inhibitors," J. Med. Chem. 47, 5298-5310 (2004); Nair, et al., "HIV integrase inhibitors with nucleobase scaffolds: discovery of a highly potent anti-HIV agent," J. Med. Chem. 49, 445-447 (2006); Nair, et al., "Conceptually novel HIV integrase inhibitors with nucleobase scaffolds: discovery of a highly potent anti-HIV agent," Antiviral Res. 70, A26 (2006); Uchil et al., "Novel strategy to assemble the β-diketo acid pharmacophore of HIV integrase inhibitors on purine nucleobase scaffolds, J. Org. Chem. 72, 8577-8579 (2007), Sato, et al., "Novel HIV-1 integrase inhibitors derived from quinolone antibiotics," J. Med. Chem. 49, 1506-1508 (2006); Garvey et al., "The Napthyridinone GSK365735 is a novel, potent human immunodeficiency virus type 1 integrase inhibitor and antiretroviral," Antimicrob. Agents Chemother. 52, 901-908 (2008); Min et al., "Pharmacokinetics (PK) and safety in healthy and HIV-infected subjects and short-term antiviral efficacy of S/GSK1265744, a new generation once daily HIV integrase inhibitor," $49^{th}$ ICAAC Abstract no. H-1228, p 249 (2009), Xu et al., "Discovery of GS-9350: A novel pharmacoenhancer without anti-HIV activity," $49^{th}$ ICAAC Abstract no. H-934, p 248 (2009), Min et al., "Pharmacokinetics and safety of S/GSK1349572, a next-generation HIV integrase inhibitor, in healthy volunteers," Antimicrob. Agents in Chemother. 54, 254-258 (2010), Johns et al., "Discovery of S/GSK1349572: a once-daily next generation integrase inhibitor with a superior resistance profile," $17^{th}$ CROI Abstract no. 55, p 86 (2010), Cohen, et al., "Single-tablet, fixed-dose regimen of elvitegravir/emtricitabine/tenofovir disoproxil fumarate/GS-9350 achieves a high rate of virologic suppression and GS-9350 is an effective booster," $17^{th}$ CROI Abstract no. 58LB, p 87 (2010), Nair et al., New Pyridinone Diketo Acid Inhibitors of HIV-1 Integrase: Anti-HIV Data, SAR Analysis, Microsome Stability, Cytochrome P450 Studies and Rodent Pharmacokinetics, $49^{th}$ ICAAC Abstracts, F1-2023, p 211 (2009), Nair et al., "Beta-diketo acids with purine nucleobase scaffolds: novel selective inhibitors of the strand transfer step of HIV integrase," Bioorg. Med. Chem. Lett. 16, 1920-1923 (2006), Chi et al., "A novel diketo phosphonic acid that exhibits specific, strand-transfer inhibition of HIV integrase and anti-HIV activity," Bioorg. Med. Chem. Lett. 17, 1266-1269 (2007)]. Other publications in the area are of peripheral relationship to this invention disclosure.

Patents of relevance to this invention disclosure are: Selnick, H. G. et al., (Merck & Co. Inc.), "Preparation of nitrogen-containing 4-heteroaryl-2,4-dioxobutyric acids useful as HIV integrase inhibitors," WO 9962513; Young, S. D., et al., (Merck & Co. Inc.), "Preparation of aromatic and heteroaromatic 4-aryl-2,4-dioxobutyric acid derivatives useful as HIV integrase inhibitors," WO 9962897; Fujishita, T., et al., Yoshinaga, T., et al. (Shionogi & Co. Ltd.), "Preparation of aromatic heterocycle compounds having HIV integrase inhibiting activities," WO 0039086; Akihiko, S., (Shionogi & Co. Ltd.), "Medicinal compositions containing propenone derivatives," WO 0196329; Payne, L. S., et al., (Merck & Co. Inc.; Tularik, Inc.), "Preparation of 1,3-diaryl-1,3-propanediones as HIV integrase inhibitors," WO 0100578; Egbertson, M., et al., (Merck & Co. Ltd.), "HIV integrase inhibitors," WO 9962520. Some of the patents cited above are closely related. However, none of the patents or publications describe the class of compounds according to the present invention.

Other patents of peripheral relationship to this invention are: Anthony, et al., (Merck & Co. Inc.), "Aza and polyazanapthalenyl-carboxamides useful as HIV integrase inhibitors," WO 02/30426; Sato, et al., (Japan Tobacco Inc.), "Preparation of 4-oxoquinoline derivatives as HIV integrase inhibitors," WO 2004046115; Sato, et al., (Japan Tobacco Inc.), "Novel 4-oxoquinoline compounds and use thereof as HIV integrase inhibitors," WO 2005113509; Crescenzi, et al., (Instituto Di Richerche Di Biologia Molecolare P. Angeletti SPA) "Preparation of N-substituted hydroxypyrimidinone carboxamide inhibitors of HIV integrase," WO 2003035077; Belyk, et al., (Merck & Co. Inc., Instituto Di Richerche Di Biologia Molecolare P. Angeletti SPA), "Preparation of N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide potassium salts as HIV integrase inhibitors," WO 2006060712; Belyk et al., (Merck & Co. Inc.), "Potassium salt of an HIV integrase inhibitor," US 2006, 0122205 A1; Sato, et al., (Japan Tobacco Inc.), "Preparation of quinolizinone compounds as HIV integrase inhibitors," WO 2006033422; Yoshida, H., et al., (Shionogi & Co. Ltd.), "Preparation of carbamoyl-pyridinone derivative having HIV integrase inhibitory activity," WO 2006030807; Dress, et al., (Pfizer, Inc.), "Preparation of N-hydroxy pyrrolopyridinecarboxamides as inhibitors of HIV integrase," WO 2006027694; Naidu, et al., (Bristol-Myers Squibb Co.), "HIV integrase inhibitors," US 2005/0261322; Naidu, et al., (Bristol-Myers Squibb Co.), "Bicyclic heterocycles as HIV integrase inhibitors," US 2005/0267105; Naidu, et al., (Bristol-Myers Squibb Co.), "Bicyclic heterocycles as HIV integrase inhibitors," US 2006/0199956 and Nair et al., "Diketo acids with nucleobase scaffolds: anti-HIV replication inhibitors targeted at HIV integrase," US, 2007/7250,421; Nair, et al., "Pyridinone Diketo Acids: Inhibitors of HIV Replication in Combination Therapy, U.S. National Stage patent application Ser. No. 12/309,017, Filed Jan. 2, 2009. While some of the patents cited above are more related than others, none of the patents or publications describe the class of compounds according to the present invention disclosure.

The class of compounds described in this invention disclosure are chiral and achiral oxy-substituted cyclopentyl pyridinone diketocarboxamides and their derivatives. The compounds have been designed as inhibitors of HIV-1 integrase and have been discovered to possess significant in vitro anti-HIV activity. Two examples are shown below (FIGS. 1a and b). The chiral compound (S,S-isomer, FIG. 1a) exhibits anti-HIV activity in cell culture with an $EC_{50}$ of 25 nM (TI>1,500). The achiral compound (FIG. 1b) is more active and has an $EC_{50}$ of 10 nM (TI>10,000).

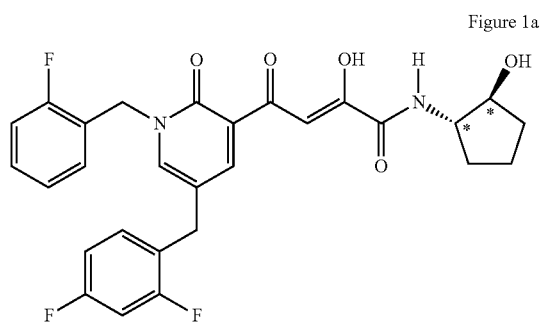

Figure 1a

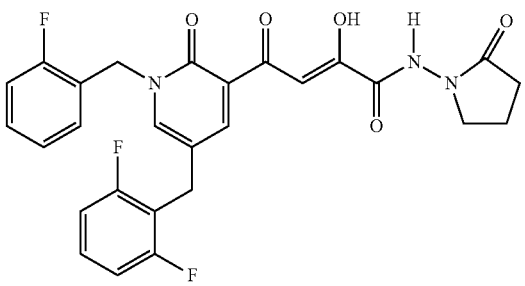

Figure 1b

SUMMARY OF THE INVENTION

Chiral and achiral oxy-substituted cyclopentyl pyridinone diketocarboxamides and their derivatives and methods for their preparations are disclosed. The compounds are represented by formula I and include chiral and achiral compounds, tautomers, regioisomers, geometric isomers, wherein the modified nucleobase scaffold and R, X and Z groups are as otherwise defined in the specification. These complex carboxamides are designed as inhibitors of HIV replication through inhibition of HIV integrase. The compounds are useful in the prevention, inhibition or treatment of infection by HIV and in the treatment of AIDS and ARC, either as the compounds, or as pharmaceutically acceptable salts, with pharmaceutically acceptable carriers, used alone or in combination with antivirals, immunomodulators, antibiotics, vaccines, and other therapeutic agents, especially other anti-HIV compounds (including other anti-HIV integrase agents), which can be used to create combination anti-HIV cocktails. Methods of treating, preventing and/or reducing the likelihood of AIDS and ARC and methods of treating or preventing infection by HIV are also described, the method comprising administering one or more compounds according to the present invention, optionally in combination with additional agents, including anti-HIV agents in effective amounts to a patient or subject in need.

Compounds according to the present invention exhibit one or more of the following characteristics desired in anti-HIV compounds: increased anti-HIV activity, enhanced bioavailability, enhanced therapeutic index, enhanced stability to metabolic degradation and little drug-to-drug interaction in comparison with prior art compounds of similar (anti-HIV) activity. The present compounds represent a material advance in the treatment and/or prevention of HIV and related secondary conditions and/or disease states.

Pharmaceutical compositions which include one or more compounds according to the present invention in combination with a pharmaceutically acceptable carrier, additive or excipient, optionally in combination with at least one additional agent as otherwise described herein represent an additional aspect of the invention. A kit comprising a pharmaceutical composition according to the present invention and instructions on how to administer the composition to a patient in need represent a further aspect of the invention.

DETAILED DESCRIPTION OF THE INVENTION

The following terms are used throughout the specification to describe the present invention. Unless otherwise indicated, a term used to describe the present invention shall be given its ordinary meaning as understood by those skilled in the art.

The term "compound", as used herein, unless otherwise indicated, refers to any specific chemical compound disclosed herein and includes tautomers, regioisomers, geometric isomers, and where applicable, optical isomers thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The breadth of the term "compound" shall be construed within the context of the use of the term. It is noted that in the present invention, where relevant, chiral atoms are represented by an asterisk (*) next to the carbon atom. The symbol ----- is used to signify a single or double bond according to the context in which the bond is used. It is noted that where a substituent should be present in context but is not specifically signified, it is understood that such substituent represents a hydrogen (H) atom.

The term "patient" or "subject" is used throughout the specification to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective" is used herein, unless otherwise indicated, to describe an amount of a compound or composition or component which, in context, is used to produce or effect an intended result, whether that result relates to the treatment of a viral, microbial or other disease state, disorder or condition associated with HIV, ARC or AIDS or alternatively, is used to produce another compound, agent or composition. This term subsumes all other effective amount or effective concentration terms which are otherwise described in the present application.

The term "scaffold" is used to mean a pyridinone chemical structure containing at least three substituents on this scaffold, one of which is the diketocarboxamide moiety as otherwise defined herein, and the other two are benzyl groups of which $R_1$, $R_2$, $R_3$ and $R_4$ are as defined herein.

The term "prevention" is used within context to mean "reducing the likelihood" of a condition or disease state from occurring as a consequence of administration or concurrent administration of one or more compounds or compositions according to the present invention, alone or in combination with another agent. Thus, the term prevention is used within the context of a qualitative measure and it is understood that the use of a compound according to the present invention to reduce the likelihood of an occurrence of a condition or disease state as otherwise described herein will not be absolute, but will reflect the ability of the compound to reduce the likelihood of the occurrence within a population of patients or subjects in need of such prevention.

The term "human immunodeficiency virus" or "HIV" shall be used to describe human immunodeficiency viruses 1 and 2 (HIV-1 and HIV-2).

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A Category 2 (ARC) infection is characterized by the following criteria: The patient's T-cells have dropped below 500 but never below 200, and that patient has never had any Category 3 diseases (as set forth below) but have had at least one of the following defining illnesses—

Bacillary angiomatosis
Candidiasis, oropharyngeal (thrush)
Candidiasis, vulvovaginal; persistent, frequent, or poorly responsive to therapy
Cervical dysplasia (moderate or severe)/cervical carcinoma in situ
Constitutional symptoms, such as fever (38.5 C) or diarrhea lasting longer than 1 month
Hairy leukoplakia, oral
Herpes zoster (shingles), involving at least two distinct episodes or more than one dermatome
Idiopathic thrombocytopenic purpura
Listeriosis
Pelvic inflammatory disease, particularly if complicated by tubo-ovarian abscess
Peripheral neuropathy According to the U.S. government, in Category 2 ARC, the immune system shows some signs of damage but it isn't life-threatening.

A Category 3 (AIDS) infection is characterized by the following criteria:
your T-cells have dropped below 200 or
you have had at least one of the following defining illnesses—
Candidiasis of bronchi, trachea, or lungs
Candidiasis, esophageal
Cervical cancer, invasive**
Coccidioidomycosis, disseminated or extrapulmonary
Cryptococcosis, extrapulmonary
Cryptosporidiosis, chronic intestinal (greater than 1 month's duration)
Cytomegalovirus disease (other than liver, spleen, or nodes)
Cytomegalovirus retinitis (with loss of vision)
Encephalopathy, HIV-related
Herpes simplex: chronic ulcer(s) (greater than 1 month's duration); or bronchitis, pneumonitis, or esophagitis
Histoplasmosis, disseminated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
*Mycobacterium avium* complex or *M. kansasii*, disseminated or extrapulmonary
*Mycobacterium tuberculosis*, any site (pulmonary** or extrapulmonary)
*Mycobacterium*, other species or unidentified species, disseminated or extrapulmonary
*Pneumocystis carinii* pneumonia
Pneumonia, recurrent**
Progressive multifocal leukoencephalopathy
*Salmonella* septicemia, recurrent
Toxoplasmosis of brain
Wasting syndrome due to HIV The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided preferably that effective concentrations of coadministered compounds or compositions are found in the subject at a given time. The term coadministration also encompasses, in certain instances, the serial administration of agents which are administered serially in a patient to produce an intended effect, regardless of the time of administration and concentration of agent found in the subject.

The term "independently" is used herein to indicate that a variable, which is independently applied, varies independently from application to application.

The present invention is directed to compounds of the general molecular formula I, combinations thereof, or pharmaceutically acceptable salts thereof, in the inhibition of HIV integrase, the inhibition, prevention which reduces the likelihood of or treatment of HIV infections and in the treatment of AIDS and ARC. Compounds of formula I are defined as follows:

Formula I including chiral isomers, geometric isomers, tautomers, regioisomers, and pharmaceutically acceptable salts thereof, wherein the pyridinone scaffold and R, X, Z groups are as otherwise defined in the specification Wherein $R_1$, $R_2$, $R_3$ and $R_4$ are each independently H or a halogen (F, Cl, Br or I, preferably F);

X and Z are each independently represented by the following:
X=CH (carbon center is chiral)
X=N (center is achiral)
Z=—OH (carbon carrying OH which is sp3 hybridized and chiral); and
Z==O (a keto group; i.e., a carbon carrying oxygen which is sp2 hybridized and achiral).

In preferred compounds according to the present the invention, $R_1$, $R_2$, $R_3$ and $R_4$ are as follows:
$R_1$=o-F, $R_2$=H, $R_3$=p-F, $R_4$=o-F (by way of convention, for example, o-F represents an ortho substituted fluorine, p-F represents a para substituted fluorine)
$R_1$=p-F, $R_2$=H, $R_3$=p-F, $R_4$=o-F
$R_1$=o-F, $R_2$=o-F, $R_3$=o-F, $R_4$=H
$R_1$=o-F, $R_2$=H, $R_3$=o-F, $R_4$=o-F
$R_1$=o-F, $R_2$=H, $R_3$=p-F, $R_4$=H
$R_1$=o-F, $R_2$=p-F, $R_3$=p-F, $R_4$=o-F
$R_1$=o-F, $R_2$=o-F, $R_3$=o-F, $R_4$=o-F
X is CH or N; and
Z is OH or =O, or a pharmaceutically acceptable salt or ester thereof.

Also embraced by the present invention are pharmaceutical compositions useful for inhibiting HIV integrase, comprising an effective amount of a compound of this invention as described herein, and a pharmaceutically acceptable carrier, additive or excipient. Pharmaceutical compositions useful for treating infection by HIV or for treating AIDS or ARC are also included by the present invention. The present invention also includes methods for inhibiting the viral enzyme, HIV integrase, and a method of inhibiting HIV growth and/or replication, or treating an HIV infection or for treating AIDS or ARC in a patient in need thereof. In addition, the present invention is directed to a pharmaceutical composition comprising, in combination, a therapeutically effective amount of a compound of the present invention in combination with a therapeutically effective amount of an agent for the treatment of AIDS selected from (i) an AIDS or HIV antiviral agent, (ii) an anti-infective agent, (iii) an immunomodulator, (iv) other useful therapeutic agents including antibiotics and other antiviral agents.

The compounds of the present invention also embrace regioisomers with respect to the pyridinone scaffold and $R_1$, $R_2$, $R_3$ and $R_4$ and these regioisomeric forms are included in the present invention. The compounds also embrace geometric isomers and these forms are also included in the present invention.

Tautomeric forms may also exist with compounds of the present invention. Thus, the terminology "and tautomers thereof" is used in describing tautomeric forms of compounds of formula I such as Ia and Ib (shown below). By naming compounds as being represented by the general formula I and tautomers thereof, it is understood that for the purposes of the present invention that tautomers Ia and Ib are also included. Similarly, by referring to compound (Ia), it is understood for the purposes of the present application that tautomers (I) and (Ib) are also intended to be included. The same holds true for references to tautomer (Ib).

The compounds of the present invention have both chiral (asymmetric) and achiral (symmetric) centers. Thus, optical isomers resulting from the presence of asymmetric centers represent a further aspect of the present invention. Examples of both chiral and achiral compounds are shown below in FIG. 2.

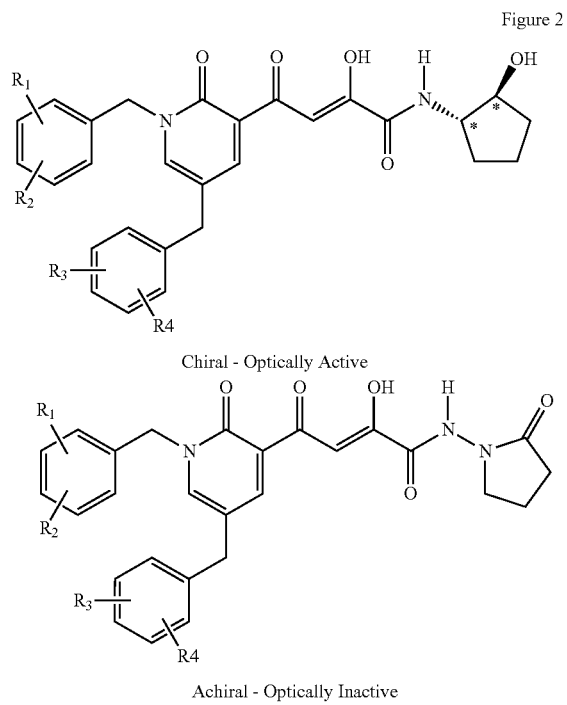

Figure 2

Chiral - Optically Active

Achiral - Optically Inactive

When the variables involving $R_1$, $R_2$, $R_3$, and $R_4$ occur more than once in any formula I, the definition on each occurrence is independent of its definition at every other occurrence. Regioisomeric pyridinones, in addition to those structurally identified, are also part of this invention. Combinations of pyridinones and variables are permissible only if, in context, such combinations result in stable compounds.

Particular compounds of structural formula I include:
1. (1S,2S)-4-(5-(2,4-difluorobenzyl)-1-(2-fluorobenzyl)-2-oxo-1,2-dihydropyridin-3-yl)-2-hydroxy-N-(2-hydroxycyclopentyl)-4-oxobut-2-enamide
2. (1R,2R)-4-(5-(2,4-difluorobenzyl)-1-(2-fluorobenzyl)-2-oxo-1,2-dihydropyridin-3-yl)-2-hydroxy-N-(2-hydroxycyclopentyl)-4-oxobut-2-enamide
3. 4-(5-(2,4-difluorobenzyl)-1-(2-fluorobenzyl)-2-oxo-1,2-dihydropyridin-3-yl)-2-hydroxy-4-oxo-N-(2-oxopyrrolidin-1-yl)but-2-enamide
4. (1S,2S)-4-(5-(2,4-difluorobenzyl)-1-(4-fluorobenzyl)-2-oxo-1,2-dihydropyridin-3-yl)-2-hydroxy-N-(2-hydroxycyclopentyl)-4-oxobut-2-enamide
5. (1R,2R)-4-(5-(2,4-difluorobenzyl)-1-(4-fluorobenzyl)-2-oxo-1,2-dihydropyridin-3-yl)-2-hydroxy-N-(2-hydroxycyclopentyl)-4-oxobut-2-enamide
6. 4-(5-(2,4-difluorobenzyl)-1-(4-fluorobenzyl)-2-oxo-1,2-dihydropyridin-3-yl)-2-hydroxy-4-oxo-N-(2-oxopyrrolidin-1-yl)but-2-enamide
7. (1S,2S)-4-(1-(2-fluorobenzyl)-5-(4-fluorobenzyl)-2-oxo-1,2-dihydropyridin-3-yl)-2-hydroxy-N-(2-hydroxycyclopentyl)-4-oxobut-2-enamide
8. (1R,2R)-4-(1-(2-fluorobenzyl)-5-(4-fluorobenzyl)-2-oxo-1,2-dihydropyridin-3-yl)-2-hydroxy-N-(2-hydroxycyclopentyl)-4-oxobut-2-enamide
9. 4-(1-(2-fluorobenzyl)-5-(4-fluorobenzyl)-2-oxo-1,2-dihydropyridin-3-yl)-2-hydroxy-4-oxo-N-(2-oxopyrrolidin-1-yl)but-2-enamide
10. (1S,2S)-4-(1-(2,6-difluorobenzyl)-5-(2-fluorobenzyl)-2-oxo-1,2-dihydropyridin-3-yl)-2-hydroxy-N-(2-hydroxycyclopentyl)-4-oxobut-2-enamide
11. (1R,2R)-4-(1-(2,6-difluorobenzyl)-5-(2-fluorobenzyl)-2-oxo-1,2-dihydropyridin-3-yl)-2-hydroxy-N-(2-hydroxycyclopentyl)-4-oxobut-2-enamide
12. 4-(1-(2,6-difluorobenzyl)-5-(2-fluorobenzyl)-2-oxo-1,2-dihydropyridin-3-yl)-2-hydroxy-4-oxo-N-(2-oxopyrrolidin-1-yl)but-2-enamide
13. (1S,2S)-4-(1,5-bis(2,4-difluorobenzyl)-2-oxo-1,2-dihydropyridin-3-yl)-2-hydroxy-N-(2-hydroxycyclopentyl)-4-oxobut-2-enamide
14. (1R,2R)-4-(1,5-bis(2,4-difluorobenzyl)-2-oxo-1,2-dihydropyridin-3-yl)-2-hydroxy-N-(2-hydroxycyclopentyl)-4-oxobut-2-enamide
15. 4-(1,5-bis(2,4-difluorobenzyl)-2-oxo-1,2-dihydropyridin-3-yl)-2-hydroxy-4-oxo-N-(2-oxopyrrolidin-1-yl)but-2-enamide
16. (1S,2S)-4-(5-(2,6-difluorobenzyl)-1-(2-fluorobenzyl)-2-oxo-1,2-dihydropyridin-3-yl)-2-hydroxy-N-(2-hydroxycyclopentyl)-4-oxobut-2-enamide
17. (1R,2R)-4-(5-(2,6-difluorobenzyl)-1-(2-fluorobenzyl)-2-oxo-1,2-dihydropyridin-3-yl)-2-hydroxy-N-(2-hydroxycyclopentyl)-4-oxobut-2-enamide
18. 4-(5-(2,6-difluorobenzyl)-1-(2-fluorobenzyl)-2-oxo-1,2-dihydropyridin-3-yl)-2-hydroxy-4-oxo-N-(2-oxopyrrolidin-1-yl)but-2-enamide
19. (1S,2S)-4-(1,5-bis(2,6-difluorobenzyl)-2-oxo-1,2-dihydropyridin-3-yl)-2-hydroxy-N-(2-hydroxycyclopentyl)-4-oxobut-2-enamide
20. (1R,2R)-4-(1,5-bis(2,6-difluorobenzyl)-2-oxo-1,2-dihydropyridin-3-yl)-2-hydroxy-N-(2-hydroxycyclopentyl)-4-oxobut-2-enamide
21. 4-(1,5-bis(2,6-difluorobenzyl)-2-oxo-1,2-dihydropyridin-3-yl)-2-hydroxy-4-oxo-N-(2-oxopyrrolidin-1-yl)but-2-enamide The compounds of the present invention are useful in the inhibition of HIV integrase, the prevention, the likelihood of reduction of and/or treatment of infection by HIV and in the treatment of the disease known as AIDS. Treating AIDS or preventing or treating infection by HIV is defined as including the treatment of a wide range of states of HIV infection: AIDS, ARC and actual or potential exposure to HIV (e.g., through blood transfusion, exchange of body fluids, bites, needle punctures, exposure to infected patient blood during medical or dental procedures, and other means, such patients or subjects being considered at risk for HIV infection).

Other applications are also part of this invention. For example, the compounds of this invention are useful in the preparation and execution of screening assays for antiviral compounds including in the isolation of viral enzyme mutants and in further understanding of the enzyme, HIV integrase.

The present invention also provides for the use of a compound of structural formula (I) to make a pharmaceutical composition useful for inhibiting HIV integrase and in the treatment of AIDS or ARC.

The compounds of the present invention may be administered in the form of well-known "pharmaceutically acceptable" salts. The latter is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, camsylate, mucate, carbonate, napsylate, chloride, nitrate, clavulanate, N-methylglucamine, citrate, ammonium salt, dihydrochloride, oleate, edetate, oxalate, edisylate, pamoate, estolate, palmitate, esylate, fumarate, phosphate, diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and others which can be used as a dosage form for modifying the solubility or hydrolysis characteristics or can be used in sustained release or pro-drug formulations. The pharmaceutically acceptable salts of this invention include those with counterions such as sodium, potassium, calcium, lithium, magnesium, zinc, and from bases such as ammonia, ethylenediamine, N-methylglutamine, lysine, arginine, ornithine, choline, N,N'-dibenzylethylenedianine, chloroprocaine, diethanolamine, procaine, N-benzylphenethylamine, diethylamine, piperazine, tris(hydroxymethyl)aminomethane, and tetramethylammonium hydroxide, among numerous others.

Also, in the case of an alcohol group being present, pharmaceutically acceptable esters may be employed, e.g., acetate, maleate, pivaloyloxymethyl and others, more preferably $C_1$-$C_{20}$ esters (preferably $C_2$ to $C_{12}$ esters) and those esters known in the art for improving solubility or hydrolysis characteristics for use as sustained release or pro-drug formulations.

Therapeutically effective amounts of the compounds of the present invention may be administered to patients orally, parenterally, by inhalation spray, topically, or rectally, in dosage unit formulations containing pharmaceutically-acceptable carriers, adjuvants and vehicles including nanoparticle drug delivery approaches. The term "pharmaceutically acceptable" is meant to infer that the carrier, diluent, excipient or other additive is biologically compatible with the other ingredients of the formulation and not deleterious to the patient or recipient. Pharmaceutical compositions are in pharmaceutical dosage form and may be administered in the form of orally-administrable suspensions or tablets, nasal sprays and injectable preparations (injectable aqueous or oleagenous suspensions or suppositories). This method of treatment is part of the invention. The administration approaches used (e.g., orally as solution or suspension, immediate release tablets, nasal aerosol or inhalation, injectable solutions or suspensions or rectally administered in the form of suppositories) involve techniques that are well-known in the art of pharmaceutical formulation.

The compounds of this invention can be administered orally to humans in a preferred form (such as tablets) and in an effective amount within a preferred dosage range of about 0.05 to 200 mg/kg, more preferably about 0.1 to about 25 mg/kg body weight in divided doses. The specific dose level and frequency of dosage for any particular patient may be varied and will depend upon a variety of factors including compound activity, compound metabolism and duration of action, patient age, body weight, general health, sex, diet, mode and time of administration, rate of excretion, drug combination, the severity of the particular condition, and the condition of the patient undergoing therapy.

The present invention also includes therapeutically effective combinations of the HIV integrase inhibitor compounds of formula I with one or more other therapeutic agents such as AIDS antivirals, other antiviral agents, immunomodulators, antiinfectives, antibiotics, vaccines or other therapeutic agents. Some examples are given below.

| ANTIVIRAL AGENTS, ANTI-INFECTIVES, IMMUNOMODULATORS, OPPORTUNISTIC INFECTION DRUGS, OTHER RELEVANT DRUGS IN AIDS | | |
|---|---|---|
| Drug Name | Manufacturer | Therapeutic Use |
| 097 | Hoechst/Bayer | HIV infection, AIDS, ARC (NNRT inhibitor) |
| Amprenivir 141W94, GW141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR 177 | Aronex Pharm | HIV infection, AIDS, ARC |
| Beta-fluoro-ddA | National Cancer Institute | AIDS-associated diseases |
| BMS-232623 (CGP-73547) | Bristol-Myers Squibb/Novartis | HIV infection, AIDS, ARC (protease inhibitor) |

ANTIVIRAL AGENTS, ANTI-INFECTIVES, IMMUNOMODULATORS, OPPORTUNISTIC INFECTION DRUGS, OTHER RELEVANT DRUGS IN AIDS

-continued

| Drug Name | Manufacturer | Therapeutic Use |
|---|---|---|
| BMS-234475 (CGP-61755) | Bristol-Myers Squibb/Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV Peripheral CMV Retinitis |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP-266) | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | Herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Scienes | ARC, AIDS |
| Indinavir | Merck | HIV infection, AIDS, ARC, asymptomatic HIV positive; combination with AZT/ddI/ddC |
| Isentress (Raltegravir) | Merck | HIV infection, AIDS, ARC (integrase inhibitor) |
| ISIS-2922 | ISIS Pharmaceuticals | CMV retinitis |
| KNI-272 | Natl. Cancer Institute | HIV-associated diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CVV retinitis, HIV infection, other CMV |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| Valaciclovir | Glaxo Wellcome | Genital HSV & CMV infections |

-continued

ANTIVIRAL AGENTS, ANTI-INFECTIVES, IMMUNOMODULATORS, OPPORTUNISTIC INFECTION DRUGS, OTHER RELEVANT DRUGS IN AIDS

| Drug Name | Manufacturer | Therapeutic Use |
|---|---|---|
| Virazole Ribavirin | Viratek/ICN (Costa Mesa, CA) | Asymptomatic HIV positive, LAS, ARC |
| VX-478 | Vertex | HIV infection, AIDS, ARC |
| Zalcitabine | Hoffmann-LaRoche | HIV infection, AIDS, ARC with AZT |
| Zidovudine; AZT | Glaxo Wellcome | HIV infection, AIDS, ARC, Kaposi's sarcoma, in combination with other therapies |
| Tenofovir diisoproxil fumarate salt (Viread ®) | Gilead | HIV infection, AIDS, (RT inhibitor) |
| Combivir ® | GSK | HIV infection, AIDS, (RT inhibitor) |
| Abacavir succinate (or Ziagen ®) | GSK | HIV infection, AIDS, (reverse transcriptase inhibitor) |
| Fuzeon ® (or T-20) | Roche/Trimeris | HIV infection, AIDS, viral Fusion inhibitor |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki Immuno PHARM | Blocks HIV fusion with CD4+ cells |
| Gamma Interferon | Genentech | ARC, in combination w/TNF |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4-IgG | Genentech | AIDS, ARC |
| rCD4-IgG Hybrids | | AIDS, ARC |
| Recombinant Soluble Human CD4 | Biogen | AIDS, ARC |

ANTIVIRAL AGENTS, ANTI-INFECTIVES, IMMUNOMODULATORS, OPPORTUNISTIC INFECTION DRUGS, OTHER RELEVANT DRUGS IN AIDS -continued

| Drug Name | Manufacturer | Therapeutic Use |
| --- | --- | --- |
| Interferon Alfa 2a | Hoffman-LaRoche | Kaposi's sarcoma, AIDS, AR, combination w/AZT |
| SK&F1-6528 Soluble T4 | Smith Kline | HIV infection |
| Thymopentin | Immunobiology Research Institute (Annandale, NJ) | HIV infection |
| Tumor Necrosis Factor (TNF) | Genentech | ARC, in combination w/gamma Interferon |
| AK602 | Kumamoto University Japan | HIV infection (entry and fusion inhibitor) |
| Alovudine | Medivir, UK Ltd. | HIV infection (nucleoside RT inhibitor) |
| Amdoxovir | RFS Pharma, LLC | Treatment of HIV and HBV infections (nucleoside RT Inhibitor) |
| AMD070 | AnorMED, Inc. | HIV infection (entry and fusion inhibitor) |
| Atazanavir (Reyataz) | Bristol -Myers Squibb | HIV infection (protease inhibitor) |
| AVX754 (apricitabine) | Avexa Ltd. | HIV infection (nucleoside RT inhibitor |
| Bevirimat | Panacos Pharmaceuticals | HIV infection (maturation inhibitor) |
| BI-201 | BioInvent | HIV infection (gene therapy, blocks HIV tat gene). |
| BMS-378806 | Bristol - Myers Squibb | HIV infection (entry inhibitor) |
| BMS-488043 | Bristol - Myers Squibb | HIV infection (entry and fusion inhibitor) |
| BMS-707035 | Bristol - Myers Squibb | HIV infection (integase inhibitor) |
| C31G | Cellegy Pharmaceuticals, Inc | HIV infection and other sexually transmitted diseases (STDs) |
| Carbopol 974P | ReProtect, LLC | Sexual transmission of HIV |
| Calanolide A | Sarawak MediChem Pharmaceuticals, Inc. | HIV infection (non-nucleoside RT inhibitor) |
| Carrageenan | FMC Biopolymer | HIV microbicide |
| Cellulose sulfate | Polydex Pharmaceuticals, Ltd. | Prevention of HIV infection and other sexually transmitted diseases |
| Cyanovirin-N | Cellegy Pharmaceuticals, Inc. | Prevention of sexual transmission of HIV infection |
| Darunavir | Tibotec | HIV infection (co-administered with ritonavir) |
| Delavirdine | Pfizer | HIV infection (non-nucleoside RT inhibitor) |
| Dextran sulfate | Ueno Fine Chemicals Industry, Ltd. | Prevention of transmission of HIV |
| Didanosine (Videx, Videx EC) | Bristol - Myers Squibb | HIV infection (nucleoside RT inhibitor) |
| Efavirenz | Bristol - Myers Squibb | HIV infection (non-nucleoside RT inhibitor) |
| Elvucitabine | Achillion Pharmaceuticals | HIV infection (nucleoside RT inhibitor) |
| Emtricitabine | Gilead Sciences | HIV infection (nucleoside RT inhibitor) |
| Fosamprenavir (Lexiva) | GlaxoSmithKline | HIV infection (protease inhibitor) |
| Fozivudine tidoxil | Heidelberg Pharma | HIV infection (entry and fusion inhibitor) |
| GS 9137 | Gilead Sciences | HIV infection (integase inhibitor) |
| GSK-873,140 (aplaviroc) | GlaxoSmithKline | HIV infection (entry and fusion inhibitor) |

ANTIVIRAL AGENTS, ANTI-INFECTIVES, IMMUNOMODULATORS, OPPORTUNISTIC INFECTION DRUGS, OTHER RELEVANT DRUGS IN AIDS -continued

| Drug Name | Manufacturer | Therapeutic Use |
|---|---|---|
| GSK-364735 | GlaxoSmithKline | HIV infection (integase inhibitor) |
| GW640385 (brecanavir) | GlaxoSmithKline | HIV infection (protease inhibitor) |
| HG0004 | Human Genome Sciences | HIV infection (entry and fusion inhibitor) |
| HGTV43 | Enzo Therapeutics | HIV infection (antisense drug) |
| Hydroxyethyl cellulose | Union Carbide | Prevent sexual transmission of HIV |
| INCB9471 | Incyte Corporation | HIV infection (entry and fusion inhibitor) |
| KP-1461 | Koronis Pharmaceuticals | HIV infection (nucleoside RT inhibitor) |
| Lopinavir | Abbott Laboratories | HIV infection (protease inhibitor) |
| Mifepristone (VGX410, RU486) | Viral Genomix | HIV infection (gene therapy, interferes with vpr) |
| MK-0518 | Merck | HIV infection (integase inhibitor) |
| PA-457 (bevirimat) | Panacos Pharmaceuticals, Inc. | Treatment of HIV (maturation inhibitor) |
| Poly(I)-Poly(C12U) (Ampligen) | Hemispherx Biopharma, Inc. | Biological response modifier |
| PPL-100 | Merck | HIV infection (protease inhibitor) |
| PRO 140 | Progenics Pharmaceuticals, Inc. | HIV infection (entry and fusion inhibitor) |
| PRO 542 | Progenics Pharmaceuticals, Inc. | HIV infection (entry and fusion inhibitor) |
| PRO 2000 | Indevus Pharmaceuticals, Inc. | Microbicide |
| Racivir | Pharmasset, Inc. | HIV infection (nucleoside RT inhibitor) |
| SCH-D (vicriviroc) | Schering - Plough Corp | HIV infection (entry and fusion inhibitor) |
| SP01A | Samaritan Pharmaceuticals | HIV infection (entry and fusion inhibitor) |
| SPL7013 | Starpharma | Microbicide |
| TAK-652 | Takeda | HIV infection (entry and fusion inhibitor) |
| Tipranavir (Aptivus) | Boehringer Ingelheim Pharmaceuticals | HIV infection (protease inhibitor) |
| TNX-355 | Tanox, Inc. | HIV infection (entry and fusion inhibitor) |
| TMC125 (etravirine) | Tibotec | HIV infection (non-nucleoside RT inhibitor) |
| UC-781 | Cellegy Pharmaceuticals, Inc | Microbicide |
| UK-427,857 (Maraviroc) website: aidsinfo.nih.gov/DrugsNew/DrugDetailNT.aspx?MenuItem=Drugs&Search=On&_id=408 | Pfizer | HIV infection (entry and fusion inhibitor) |
| Valproic acid | Abbott | Treating seizures in HIV infection |
| VRX496 | VIRxSYS | Gene therapy |
| Zalcitabine (Hivid) | Roche | HIV infection (nucleoside T inhibitor) |
| Valganciclovir (Valcyte) | Roche | Antiviral (CMV retinitis in AIDS) |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |

ANTIVIRAL AGENTS, ANTI-INFECTIVES, IMMUNOMODULATORS, OPPORTUNISTIC INFECTION DRUGS, OTHER RELEVANT DRUGS IN AIDS

| Drug Name | Manufacturer | Therapeutic Use |
|---|---|---|
| Trimethoprim | | Antibacterial |
| Trimethoprim/sulfa | | Antibacterial |
| Piritrexim | Burroughs Wellcome | PCP treatment |
| Pentamidine isethionate | Fisons Corporation | PCP prophylaxis |
| Spiramycin | Rhone-Poulenc | Cryptosporidial diarrhea |
| Intraconazole-R51211 | Janssen Pharm | Histoplasmosis; cryptococcal meningitis |
| Trimetrexate | Warner-Lambert | PCP |
| Daunorubicin | NeXstar, Sequus | Karposi's sarcoma |
| Recombinant Human Erythropoietin | Ortho Pharm. Corp. | Severe anemia assocated w/AZT therapy |
| Recombinant Human Growth Hormone | Serono | AIDS-related wasting, cachexia |
| Megestrol Acetate | Bristol-Myers Squibb | Treatment of anorexia associated w/AIDS |
| Testosterone | Alza, Smith Kline | AIDS-related wasting |
| Total Enteral Nutrition | Norwich Eaton Pharmaceuticals | Diarrhea and malabsorption in AIDS |
| Aldesleukin (Proleukin) | Chiron Corp | Biological response modifier |
| Amphotericin B (Abelecet, AmBisome, Amphocin, Amphotec, Fungizone) | Pfizer, Bristol - Myers Squibb | Antifungal |
| Azithromycin (Zithromax) | Pfizer | Antibacterial antibiotic |
| Calcium hydroxyapatite (Radiesse | Bioform Medical, Inc. | Dermal filler |
| Doxorubicin (liposomal) (Doxil) | Ortho Biotech, Alza Corporation | Antineoplastic |
| Dronabinol (Marinol) | Unimed Pharmaceuticals, Inc. | Antiemetics |
| Entecavir (Baraclude) | Bristol-Myers Squibb | Antiviral |
| Epoetin alfa (Epogen, Procrit) | Ortho Biotech | Anemia |
| Etoposide (Etopophos (phosphate salt), Toposar, VePesid) | Pfizer, Bristol-Myers Squibb | Antineoplastic |
| Fluconazole (Diflucan) | Pfizer | Antifungal |
| Interferon alfa-2 (Intron A (2b), Roferon-A (2a) | Roche, Schering -Plough | Biological response modifiers |
| Isoniazid (Nydrazid) | Sandoz, Hoffmann La-Roche | Antimycobacterial |
| Itraconazole (Sporanox) | Ortho Biotech, Janssen Pharmaceutica | Antifungal |
| Megestrol (Megace, Megace ES) | Bristol - Myers Squibb | Anticachectic |
| Paclitaxel (Onxol, Taxol) | Bristol - Myers Squibb, IVAX Pharmaceuticals | Antineoplastic |
| Peginterferon alfa-2 (PEG-Intron (2b), Pegasys (2a)) | Roche, Schering -Plough | Antiviral |
| Pentamidine (Nebupent) | American Pharmaceutical Partners, Fujisawa Health Care, Inc. | Antiprotozoal |
| Poly-L-lactic acid (Sculptra) | Dermik Laboratories | Dermal Filler |
| Rifabutin (Mycobutin) | Pharmacia Corporation | Antimycobacterial |
| Rifampin (Rifadin, Rimactane) | Aventis Pharmaceuticals | Antimycobacterial |
| Somatropin | Pharmacia Corporation, Serono Inc | Synthetic human growth hormone |
| Sulfamethoxazole/ Trimethoprim (Bactrim, Septra) (Serostim) | Alpha care Inc, Women First Health Care, King Pharmaceuticals | Antibacterial |
| Testosterone (Androderm, Androgel, Depo-Testosterone) | Pfizer Inc, Unimed Pharmaceuticals, Inc., Alza Corporation, Watson Laboratories | Androgens |
| Trimetrexate (Neutrexin) | United States Bioscience Inc, Medimmune, Inc. | Antiprotozoal |

The combinations of the compounds of this invention with AIDS antivirals (including anti-HIV integrase-based antivirals), other antivirals, immunomodulators, anti-infectives, antibiotics, vaccines, other therapeutic agents are not limited to the list in the above Table, but includes, in principle, any combination with any pharmaceutical composition useful for the treatment against infection by HIV or for treating AIDS or ARC. Preferred combinations are simultaneous or alternating treatments of a compound of the present invention and a protease inhibitor (e.g., indinavir, nelfinavir, ritonavir, saquinavir and others), a reverse transcriptase inhibitor [nucleoside (e.g., AZT, 3TC, ddC, ddI, d4T, abacavir and others, and/or non-nucleoside (e.g., efavirenz, nevirapine, and others), or some combination of two or more of these inhibitors (see Table above). A few representative examples of relevant patents citing combinations are: EPO 0,484,071, U.S. Pat. No. 5,413,999, WO 9962513.

In such combinations, the compound of the present invention and other active agents may be separately administered or concurrently administered (coadministered). In addition, the administration of one element may be prior to, concurrent to, or subsequent to the administration of other agent(s).

(−)βDioxolane-G; DXG;
(−)β-Arctigenin; Arctigenin;
(−)-Carbovir; (−)-C-D4G; (−)-Carbovir;
(−)-β-D-2,6-Diaminopurine dioxolane; Amdoxovir; DAPD; APD
(+)-2'-Deoxy-3'-oxa-4'-thiocytidine; dOTC (+)
(+)-2'-Deoxy-3'-oxa-4'-thio-5-fluorocytidine; dOTFC (+)
(+/−)-Cyclobut-G; A-69992; (+/−)-Lobucavir; C-Oxt-G; Cyclobut-G; C-Oxetanocin-G
(R)-2QuinCOAsnPhe[CHOHCH2]PipCONHtBu
(R)-3,6-Diamino-N-(aminomethyl)hexanamide; Bellenamine
(R)-PMPA; (R)-9-(2-Phosphonylmethoxypropyl)adenine; PMPA-(R); Tenofovir
(R)-PMPDAP; PMPDAP-(R)
(S)-PMPA; (S)-9-(2-Phosphonylmethoxypropyl)adenine; PMPA(S)
(S)-9-(2-Phosphonylmethoxypropyl)adenine; (S)-PMPA
α-APA; R89439; Loviride
α-APA deriv.; R87232
α-APA deriv.; R88703
α-APA enantiomer; R90385
α-L-AZT; AZT-α-L
α-L-DXC; α-L-Dioxalane-C; DXC-α-L-
α-L-FTC; FTC-α-L-
α-Monofluoromethyldehydroornithine methyl ester; MFMOME
1,1'-Azobisformamide; ADA; Azodicarbonamide
1-(11-Octylamino-10-hydroxyundecyl)-3,7-dimethylxanthine; CT-2576
1-(2',3'-Dideoxy-2'-fluoro-β-D-threo-pentofuranosyl)cytosine; Ro 31-6840
1-(2'-Fluoro-2',3'-dideoxy-B-D-erythro-pentofuranosyl) thymine; 2'FddT
1-(2OHPr)-4-Substit-piperazine, thienyl carbamate deriv.
1-(2OHPr)-4-Substit-piperazine, thienyl carbamate deriv.
1-(2OHPr)-4-Substit-piperazine, thienyl carbamate deriv.
1-(2OHPr)-4-Substit-piperazine, thienyl carbamate deriv.
1-[(2-Hydroxyethoxy)methyl]-6-(3-methylphenyl)thio) thymine; HEPT-M
1-[(2-Hydroxyethoxy)methyl]-6-(phenylthio)-2-thiothymine; HEPT-S
1-[(2-Hydroxyethoxy)methyl]-6-(phenylthio)thymine; HEPT
1-Deoxynojirimycin; Deoxynojirimycin
141W94; VX-478; Amprenavir; Agenerase®; Approved
1592U89 Succinate; Abacavir Succinate; Ziagen® Approved
1-Aminooxyethylamine; AEA
1-Methoxyoxalyl-3,5-dicaffeoylquinic acid; 1-MO-3,5-DCQA; Dicaffeoylquinic acid deriv.
1OH-2(Cbz-Tle)3PhPr [14]paracyclophane deriv.
1OH-2(Cbz-ValNH)3PhPr [13]metacyclophane deriv.
1OH-2(Cbz-ValNH)3PhPr [13]paracyclophane deriv.
1OH-2(Cbz-ValNH)3PhPr [14]paracyclophane deriv.
1OH-2(Cbz-ValNH)3PhPr [17]paracyclophane deriv.
12-Deoxyphorbol-13-(3E,5E-decadienoate); Phorbol deriv.
16.alpha.-Bromoepiandrosterone; Epi-Br; Inactivin; HE 2000; HE2000; PPB2; DHEA deriv.
1-β-D-arabinofuranosyl-5-(2-bromovinyl)uracil; BV-ara-U; BVaraU; BV ara-U; Sorivudine; SQ-32756; Bravavir; Brovavir; Usevir; YN-72; Bromovinyl araU; BVAU
2',3'-Didehydro-3'-deoxycytidine; D4C
2',3'-Dideoxydidehydroguanosine; D4G
2',3'-Didehydro-3'-deoxythymidine; D4T; Stavudine; Zerit® Approved
2',3'-Dideoxy-3'-fluoro-4-thiothymidine; 3'-F-4-Thio-ddT
2',3'-Dideoxy-3'-fluoro-5-bromouridine; FddBrU
2',3'-Dideoxy-3'-fluoro-5-chlorocytidine; 3'-F-5-Cl-ddC
2',3'-Dideoxy-3'-fluoro-5-chlorouridine; 935U83; 5-Chloro-2',3'-dideoxy-3'-fluorouridine; FddClU; Raluridine
2',3'-Dideoxy-5-ethylcytidine; 5-Et-ddC
2',3'-Dideoxyadenosine; D2A; ddAdo; ddA
2',3'-Dideoxydidehydroadenosine; d4A
2',3'-Dideoxyguanosine; D2G; ddG
2',3'-Dideoxy-3'-hydroxymethyl cytidine; 3'-Hydroxymethyl-ddC; BEA-005
2,5'-Anhydro-3'-azido-2',3'-dideoxyuridine; AZU-2,5'-anhydro
2,5'-Anhydro-3'-azido-3'-deoxythymidine; AZT-2,5'-anhydro
2',5'diSilySpiroT; TSAO-T
2',5'diSilySpiroT; TSAO-me^3T
2,6-Diamino-2',3'-dideoxypurine-9-ribofuranoside; ddDAPR; DAPDDR; 2,6-Diamino-ddP
2,6-Diaminopurine-2',3'-dideoxydidehydroriboside; ddeDAPR
2,6-Diaminopurine-3'-fluoro-2',3'-dideoxyriboside; 3'-F-ddDAPR
2-Aminobenzylstatine Valyl Cbz deriv.; Statine deriv.
2-Glycine amide-5-chlorophenyl 2-pyrryl ketone; GCPK
[2-PyridCH2NCH3CO-Val-NHCH(Bz)]CHOHCHOH; A-77003
2'-Azido-2',3'-dideoxyadenosine; 9-(2'-Azido-2',3'-dideoxy-β-D-erythropentofuranosyl)adenine; 2'-N3ddA
2'-FddA(B-D-threo); F-ddA; 2'-F-dd-ara-A; 9-(2'-Fluoro-2',3'-dideoxy-B-D-threopentafuranosyl)adenine; Lodensine
2'-N3dda (B-D-threo); 9-(2'-Azido-2',3'-dideoxy-β-threo-pentafuranosyl)adenine
2-NaphCOAsnPhe[CHOHCH2]Pro-OtBu
2-Nitrophenylphenylsulfone; NPPS
3-(3-Oxo-1-propenyl)-3'-azido-3'-deoxythymidine; 3-(3-Oxo-1-propenyl)AZT
3-(Phenylsulfonyl)-indole deriv.; L-737,126
3,5-DCQA; 3,5-Dicaffeoylquinic acid; Dicaffeoylquinic acid
3'-Azido-2',3'-dideoxy-5-[(cyanomethyl)oxy]uridine; 3'-N3-5-Cyanomethyloxy-ddU
3'-Azido-2',3'-dideoxy-5-aminouridine; 3'-N3-5-NH2-ddU
3'-Azido-2',3'-dideoxy-5-aza-6-deazauridine; C-analog of 3'-N3-ddU
3'-Azido-2',3'-dideoxy-5-bromouridine; 3'-N3-5-Br-ddU; AZddBrU
3'-Azido-2',3'-dideoxy-5-chlorocytidine; 3'-Az-5-Cl-ddC 3'-Azido-2',3'-dideoxy-5-dimethylaminouridine; 3'-N3-5-NMe2-ddU
3'-Azido-2',3'-dideoxy-5-ethyluridine; 3'-N3-5-EtddU; CS-85; AZddEtU
3'-Azido-2',3'-dideoxy-5-fluorocytidine; 3'-N3-5-F-ddC
3'-Azido-2',3'-dideoxy-5-fluorouridine; AZddFU
3'-Azido-2',3'-dideoxy-5-hydroxyuridine; 3'-N3-5-OH-ddU
3'-Azido-2',3'-dideoxy-5-iodouridine; 3'-N3-5-1-ddU; AZdIU
3'-Azido-2',3'-dideoxy-5-methyaminouridine; 3'-N3-5-NHMe-ddU
3'-Azido-2',3'-dideoxy-5-methylcytidine; CS-92; 3'-N3-5-Me-ddC
3'-Azido-2',3'-dideoxy-5-thiocyanatouridine; 3'-N3-5-SCN-ddU
3'-Azido-2',3'-dideoxy-5-trifluoromethyluridine; 3'-N3-5-CF3-ddU
3'-Azido-2',3'-dideoxycytidine; CS-91; 3'-N3-ddC
3'-Azido-2',3'-dideoxyguanosine; AZG; 3'-N3ddG
3'-Azido-2',3'-dideoxy-N4-5-dimethylcytidine; 3'-N3-N4-5-diMe-ddC
3'-Azido-2',3'-dideoxy-N4-OH-5-methylcytidine; 3'-N3-N4-OH-5-Me-ddC
3'-Azido-2',3'-dideoxyuridine; CS-87; 3'-N3ddU; AZdU; Uravidine
3'-Azido-3'-deoxy-6-azathymidine; 3'AZ-6AzaT
3-Azido-3'-deoxythymidilyl-(5',5')-2',3'-dideoxy-5'-adenylic acid; AZT-P-ddA
3'-Azido-3'-deoxythymidilyl-(5',5')-2',3'-dideoxy-5'-adenylic acid, 2-cyanoethyl ester; AZT-P(CyE)-ddA
3'-Azido-3'-deoxythymidilyl-(5',5')-2',3'-dideoxy-5'-inosinic acid; AZT-P-ddI
3'-Azido-3'-deoxythymidine-5'-(butylmethoxyvalinyl)phosphate; 5'MeOValPO3(Bu)AZT
3'-Azido-5-chloro-2',3'-dideoxyuridine; AzddClUrd; AzddClU
3'-Deoxythymidine; ddT
3'-FddA (B-D-Erythro); 9-(3'-Fluoro-2',3'-dideoxy-B-D-erythropentafuranosyl)adenine
3'-FddC; 3'-Fluoro-2',3'-dideoxycytidine
3'-FddG; 3'-Fluoro-2',3'-dideoxyguanosine
3'-FddT; Alovudine; FddT; FddThD; 3'-FLT; FLT
3'-FddU; 3'-Fluoro-2',3'-dideoxyuridine
3'-Fluoro-2',3'-dideoxy-5-iodouridine; FddIU
3'-N3-ddA; 9-(3'-Azido-2',3'-dideoxy-B-D-erythropentafuranosyl)adenine
3TC; Lamivudine; Epivir® Approved;
Lamivudine & Zidovudine; Combivir® 3TC & AZT; Approved
4'-Acetoamidophenyl-4-guadinobenzoate; AGB
4'-Az-3'-dT; 4'-Azido-3'-deoxythymidine
4'-Az-5CldU; 4'-Azido-5-chloro-2'-deoxyuridine
4'-AzdA; 4'-Azido-2'-deoxyadenosine
4'-AzdC; 4'-Azido-2'-deoxycytidine
4'-AzdG; 4'-Azido-2'-deoxyguanosine
4'-AzdI; 4'-Azido-2'-deoxyinosine
4'-AzdU; 4'-Azido-2'-deoxyuridine
4'-Azido-2'-deoxy-β-D-erythro-pentofuranosyl-5-methyl-2,4-dioxopyrimidine; 4'-Azidothymidine
4'-Cyanothymidine; 4'-CN-T
4-Methyl-5-(pyrazinyl)-3H-1,2-dithiole-3-thione; Oltipraz
5'-[(1,4-Dihydro-1-methyl-3-pyridinylcarbonyl)oxy]-3'-azido-2',3'-deoxythymidine; DP-AZT; HP-AZT; AZT Prodrug; AZT-DHP
5'-[[(Z)-4-amino-2-butenyl]methylamino]-5'-deoxyadenosine; MDL 73811
5'-Alkylglycosidecarbonate of 3'-azido-3'-deoxythymidine; AcNHGlc-hexyl-CO3 AZT
5Cl3PhS-2IndolCONH2
5-Fluoro-2',3'-dideoxycytidine; 5-F-ddC
5-Methyl-3'-azido-2',3'-dideoxyisocytidine; MeAZddIsoC
6-O-Butanoylcastanospermine; BuCast; MDL 28,574; Celgosivir
6-Chloro-9-(2,3-dideoxy-b-D-glyceropentofuranosyl)-9H-purine; D2ClP; 6-Chloro-ddP; CPDDR; 6Cl-ddP
6-Dimethylaminopurine-2',3'-dideoxyriboside; N-6-dimethylddA; DMAPDDR
7-Chloro-N-methyl-5-(1H-pyrrol-2-yl)-3H-1,4-benzodiazepin-2-amine; Ro 24-7429
7-Chloro-5-(2-pyrryl)-3H-1,4-benzodiazepin-2(H)-one; Ro 5-3335
8-Chloro-TIBO; Tivirapine; R86183
9-(2,3-Dideoxy-β-D-ribofuranosyl)-6-(methylthio)purine; D2SMeP
9-[Bis(OHMe)cBu]A; A-69463; Cyclobutyl-A; Cyclobut-A; C-oxetanocin A
A-76890
A-77212
A-80987; Ritonavir deriv., A-81525; Ritonavir deriv., A-83962; Ritonavir deriv.
A-98881; Azacyclic urea deriv.
AA; L-ascorbic acid; Calcium Ascorbate
AAP-BHAP; U-104489; PNU-104489
Abacavir & Lamivudine & Zidovudine; Trizivir® ABC & (−)-3TC & AZT
ABT-378; Lopinavir; Component of Kaletra; Aluviran®
ABT-378 & ABT-538; Kaletra®; Lopinavir & Ritonavir; Aluviran® & Norvir®
ABT-538; Norvir®; Ritonavir; Component of Kaletra; Approved
Acemannan
Adefovir; PMEA; GS-0393
Adefovir dipivoxil; BisPom PMEA; GS-840; Preveon®
AG-1343; Viracept®; Nelfinavir; Approved
AG1350; LY316957; Nelfinavir-octahydro-thienopyridine analog
AHPBA analog; R-87366
Alpha-lipoic acid; α-Lipoic acid; Thioctic acid
ALX40-4C
AMD3100; JM3100
Amprenavir phosphate; VX-175; GW433908; GW433908A (*Sodium Salt*); GW433908G (*Calcium Salt*); Fosamprenavir
Ancer 20; Z-100
Anti-sense 25-mer phosphorothioate; GEM91
Atazanavir; CGP-73547; BMS-232632; BMS 232632; Zrivada; Latazanavir; Reyataz®
Atevirdine; U-87201E; BHAP deriv.
Aurintricarboxylic acid; Dupont ATA; Dupont DA639; SD-095345; ATA
AY 9944; trans-1,4-Bis(2-dichlorobenzylaminoethyl)cyclohexane dichlorhydrate
AZT; Zidovudine; Azidothymidine; Retrovir®
AZT-PO3(CH3)-AZT; O,O'-Bis(3'-azido-3'-deoxythymidin-5'-yl)methylphosphonate
Baicalin; TJN-151
Betulinic acid; Mairin
Betulinic acid, 3-O-(3',3'-dimethylsuccinate)
BHAP deriv.
BHAP deriv.; Rescriptor®; Delavirdine; U-90152
BHAP deriv.; U-88204E
BI-RG-587; Nevirapine; Viramune® Approved
BILA 1906 BS, BILA 2011 BS; Palinavir, BILA 2185 BS Bis(2-nitrophenyl)sulfone; Bis(2NO2Ph)SO2; NSC633001
bis-ValHOEt-N2aza-peptide isostere; CGP 53820
bis-ValHOEt-N2aza-peptide isostere; CGP 53820 analog
BMS-186318
BocPhe[CHOH(CH2)3CH=CHPhCO]IleAMBI; L-687,908
BzOCValPhe[diCHOH(RR)]PheValBzOC
BzOCValPhe[diCHOH(SS)]PheValBzOC
C2-Sym Phosphinic amide deriv. (HOECHST AG)
Calanolide A; NSC675451, Calanolide B
Capravirine; S-1153
Castanospemnine
CbzAF(CHOHCH2)AVVOMe
Cbz-Asn-Apns-Pro-NH-tBu; KNI-102
CGP 61755; Lasinavir, CGP 64222
CNI-H0294
Coactinon; I-EBU; HEPT deriv.; MKC-442; Emivirine
Conocurvone; NSC650891
Coviracil; (−)FTC; (−)-2',3'-Dideoxy-5-fluoro-3'-thiacytidine; Emtricitabine; Emtriva
C-Oxetanocin-G; A-69992; (+−)Lobucavir; C-Oxt-G; Cyclobut-G; (+−)Cyclobut-G
Crixivan®; Indinavir; MK639; L-735,524; Approved
Curdlan Sulfate
CV-N; Cyanovirin-N
Cyclic Urea Amide; SD146
Cyclosporin A; Sandimmune®
[Me-Ile-4]Cyclosporin A; SDZ NIM 811
D4A (L); L-2',3'-Didehydro-2',3'-dideoxyadenosine
D4FC; D-D4FC; 2',3'-Didehydro-2',3'-dideoxy-5-fluorocytidine; DPC 817
D4FC (L); L-2',3'-Didehydro-2',3'-dideoxy-5-fluorocytidine
D4G (L); L-2',3'-Didehydro-2',3'-dideoxyguanosine
D4I (L); L-2',3'-Didehydro-2',3'-dideoxyinosine
DABO
ddC; Dideoxycytidine; Zalcitabine; Hivid®
ddI; Dideoxyinosine; Didanosine; Videx®
Dehydroepiandrosterone; DHEA; Prasterone; Dehydroisoandrosterone; EL-10
Dextran Sulfate
Dicaffeic acid ester; L-Chicoric acid
DMP-266; Sustiva®; Efavirenz; Approved
DMP-323; XM-323
DMP-450
Docosanol; n-Docosanol
dOTC (−); (−)-2'-Deoxy-3'-oxa-4'-thiocytidine
dOTFC (−); (−)-2'-Deoxy-3'-oxa-4'-thio-5-fluorocytidine
DP-178; Pentafuside; T-20; GP41 127-162 AA; Enfuvirtide; Fuzeon®
E-BPTU; HEPT deriv.; NSC 648400
E-EBU; HEPT deriv.; MKC-442 deriv.
E-EBU-dM; HEPT deriv.; MKC-442 deriv.
E-EPSeU; HEPT deriv.; MKC-442 deriv.
E-EPU; HEPT deriv.; MKC-442 deriv.
Ebselen
Etoposide
Epoxy steroid deriv.; (4α,5α,17β)-17-Hydroxy-3-oxo-4,5-epoxyandrostane-2-carboxamide
Eulicin
Fenalamide A1; Phenalamide A1; Stipiamide
Fleephilone
Fluoroquinolone deriv.; K-12
Fortovase®; Invirase®; Saquinavir; Ro31-8959; Approved
Foscarnet; Phosphonoformic acid; Foscavir;
FPMDAP, FPMPA, FPMPG
GPGRAF Octomer; SPC3
Hammerhead anti-gag RNA Ribozyme B
Harziphilone
HBY 097; Quinoxaline deriv.
HEPT deriv.; MKC-442 deriv.
HOCH2CH2 isostere; ThienopyridCON thienyl urethane deriv.
HOCH2CH2 isostere; ThienopyridCONthienyl urethane deriv.; LY326188
HPMPA
HPMPDAP
HU; Hydroxyurea; Hydrea
Hydroxocobalamin
Hypericin
Ingenol 3,5,20-triacetate; ITA; RD3-2118
Ingenol deriv.; RD4-2138
Inophyllum B, Inophyllum P
iQoa-Mta-Apns-Thz-NH-tBu; KNI-272
Isentress (Raltegravir)
IsoquinCON furanyl urethane analog
IsoquinCON thienyl urethane analog
KNI-154; Noa-Asn-Apns-Thz-NH-tBu, KNI-174; Noa-Asn-Apns-Dmt-NH-tBu
KNI-227; Qoa-Mta-Apns-Thz-NH-tBu
L-685,434, L-685, 434-6-Hydroxy derivative, L-685,434-OEtMorphderivative; L-689,502
L-685,434-OEtNMe2, L-685,434-OPrMorph derivative, L-697,593; 2-Pyridinone deriv.
L-697,639; 2-Pyridinone deriv., L-697,661; 2-Pyridinone deriv.
L-FddC; β-L-5F-ddC
Lamivudine & Zidovudine; Combivir® 3TC & AZT; Approved
LY289612, LY289612 analog, LY289612 analog
LY-300046-HCl; PETT deriv.; Trovirdine
LY314163; Saquinavir/Nelfinavir deriv.
LY-73497; N-(2-Phenethyl)-N'-(2-thiazolyl)thiourea; PETT
MAP; Methyl acetylenic putrescine
Michellamine A; NSC650898, Michellamine B; NSC649324, Michellamine F
N-6-Et-ddA; N-Ethyl-2',3'-dideoxyadenosine
N-6-methyl ddA; N6-Methyl-2',3'-dideoxyadenosine
Naphthalene 2-sulphonate polymer; PRO 2000
Nelfinavir-octahydro-thienopyridine analog
Nonoxynol 9
NSC625487; Thiazolobenzimidazole; TBZ
Oxathiin deriv.; UC-38, Oxathiin deriv.; UC-84 P9941
Penicillin Et(NH)2 Sym dimer, Penicillin G, ET(NH)2 deriv.
Penicillin, 2Isoquin-OHPrNH2 analog
Pentosan Sulfate; Elmiron; SP54; Xylan Sulfate;
PETT Cl, F deriv., PETT deriv.
Phenoxan
Phorbol deriv.; Prostratin
Platanic acid
PMEDAP, PMEG, PMEHx; PMEI, PMEMAP, PMET
PNU-140690; U-140690; Tipranavir
Pyridinone deriv.
Quinoxalin2thione deriv; S-2720
R14458; TIBO deriv.
R82150; TIBO deriv.
R82913; TIBO deriv.
Resobene
Ribavirin; Virazole
Ro 31-8959-bis-thf deriv.
Saquinavir/Nelfinavir deriv.
SB-205569; Val-Phe-Phe-HOCH2CH2 isostere analog
SSC-52151; Telinavir
SDZ PRI 053
Suramin Sodium T22
Thalidomide
Thiangazole; (−)-Thiangazole, Thiazoloisoindol-5-one, Thiazoloisoindol-5-one, deriv.
Tle-Val-Sta, 5PhBuCOOH deriv.; Statine deriv.
UC-781
Val-Val-Sta, 5PhBuCOOH deriv.; Statine deriv.
VB-11,328
Viread®; Tenofovir Disoproxil An alternative list of drugs and/or bioactive agents useful in the treatment of HIV infections, or conditions or disease states which are secondary to HIV infections is set forth hereinbelow. One or more of these agents may be used in combination (coadminstered) with at least one anti-HIV agent as otherwise disclosed herein to treat HIV or one of its secondary conditions or disease states, including AIDS/ARC, Kaposi's sarcoma, hepatitis B virus infections, other microbial infections (such as tuberculosis) etc. When used, these compounds are also included in effective amounts.

These include (at the following website): aidsinfo.nih.gov/DrugsNew/DrugDetailNT.aspx?MenuItem=Drugs&Search=On&int_id=257
ACV; AK602; AMD070; APV; ATV; ATZ; AVX754 (apricitabine); AZT; Abacavir; Abacavir/Lamivudine/Zidovudine; Abacavir sulfate; Abacavir sulfate/Lamivudine; Abacavir/Lamivudine; Abelcet; Acyclovir; Adefovir dipivoxil; Adriamycin; Agenerase; Aldesleukin; Alovudine; Aluvia; AmBisome; Amdoxovir; Amphocin; Amphotec; Amphotericin B; Ampligen; Amprenavir; Androderm; Androgel; Apricitabine; Aptivus; Atazanavir; Atripla; Azithromycin; BMS-378806; BMS-488043; Bactrim; Baraclude; Bevirimat; Biaxin; Brecanavir; BufferGel; C31G; CD4-IgG2; CS; CV-N; Calanolide A; Calcium hydroxylapatite; Carbopol 974P; Carrageenan; Carraguard; Cellulose sulfate; Clarithromycin; Combivir; Copegus; Cotrimoxazole; Crixivan; Cyanovirin-N; Cytovene; DAPD; DLV; DS; Darunavir; Delavirdine; Depo-Testosterone; Dextran sulfate; Didanosine; Diflucan; Doxil; Doxorubicin (liposomal); Dronabinol; EFV; Efavirenz; Elvucitabine; Emtricitabine; Emtricitabine; Tenofovir disoproxil fumarate; Emtriva; Enfufirtide; Entecavir; Epivir; Epoetin alfa; Epogen; Epzicom; Etopophos (phosphate salt); Etoposide; Etravirine; FTC; Fluconazole; Fortovase; Fosamprenavir; Foxivudine tidoxil; Fungizone; Fuzeon; GS 9137; GSK-873,140 (aplaviroc); GW433908; GW640385 (brecanavir); Ganciclovir; Globulin, Immune; Growth hormone (human); Hepsera; Hivid; Human growth hormone; IL-2; INH; Immune Globulin Intravenous (Human); Indinavir; Interferon alfa-2; Interleukin-2, recombinant human; Intron A (2b); Invirase; Isentress; Isoniazid; Itraconazole; KP-1461; Lamivudine/Zidovudine; Lexiva; Lopinavir/Ritonavir; MK-0518; Nebupent; Nelfinavir; Neutrexin; Nevirapine; Norvir; Nydrazid; Peptide T; PMPA Prodrug (Viread)' Prezista (Darunavir); PRO 140; PRO 2000; PRO 542 (CD4 IGg2); Procrit (Epoetin); Proleukin; Racivir; Radiesse; Rrebetol; Rescriptor; Retrovir; Reyataz; Ribavirin; Rifabutin; Rifadin; Rifampin; Rimactane; Ritonavir; Roferon-A (2a); Saquinavir; SCH-D (vicriviroc); Somatropin; Stavudinie; Sulfamethoxazole/Trimethoprim; Sustanon; Sustiva; TNX-355; Taxol; Tenofovir; Tenofovir disoproxil fumarate; Testosterone; Tipranavir; Toposar; Trimetrexate; Trizivir; Truvada (Emtriva and Viread combination); U-90152S (Delaviridine); UC-781; UK-427,857 (maraviroc); Valcyte; Valganciclovir; Valproic acid; VePesid; Vicriviroc; Videx; Viracept (Tennofovir DF); Viramune; Virazole; Viread; Vitrasert; Zalcitabine; Zerit; Ziagen; Zidovudine; Zithromax; Zovirax.

The following representative examples are provided to illustrate details for the preparation of the compounds of the present invention. The examples are not intended to be limitations on the scope of the present invention and they should not be so construed. Furthermore, the compounds described in the following examples are not to be viewed as forming the only set of compounds that is considered as the invention, and any combination of components of the compounds or their moieties may itself form a set. This has been addressed previously in this patent document. Those skilled in the art will readily comprehend that known variations of reaction conditions and synthetic conversions described in the following preparative procedures can be used to readily prepare these other compounds routinely.

Chemical Synthesis

Precursor

Example of Synthesis of Diketoacid Precursor, 4-(5-(2,4-difluorobenzyl)-1-(2-fluorobenzyl)-2-oxo-1,2-dihydropyridin-3-yl)-2-hydroxy-4-oxobut-2-enoic acid (8)

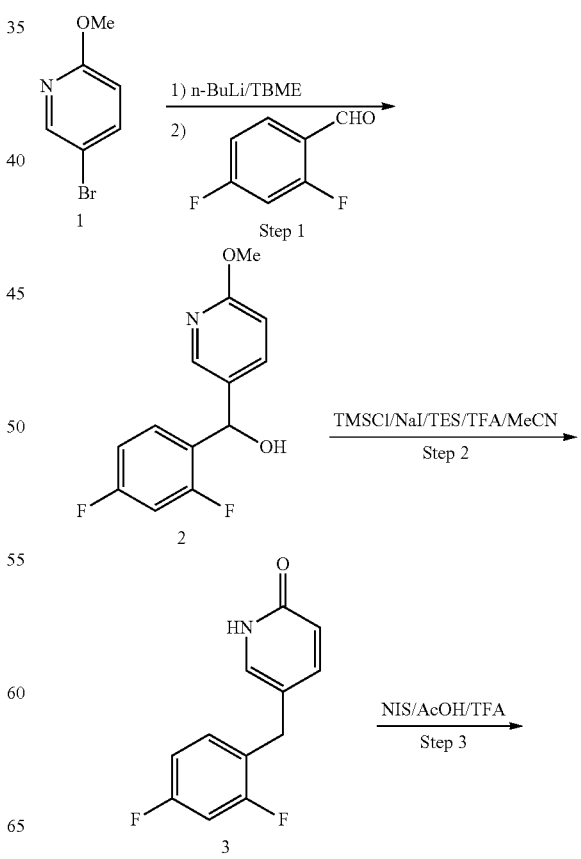

-continued

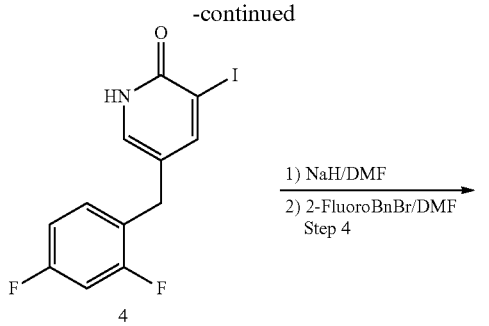
4

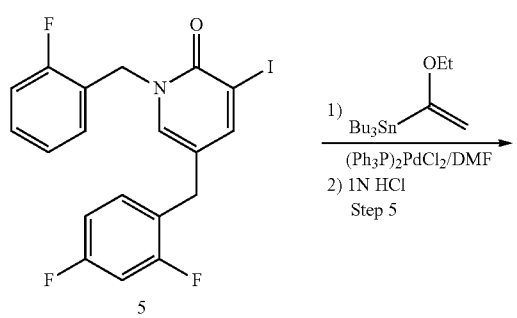
5

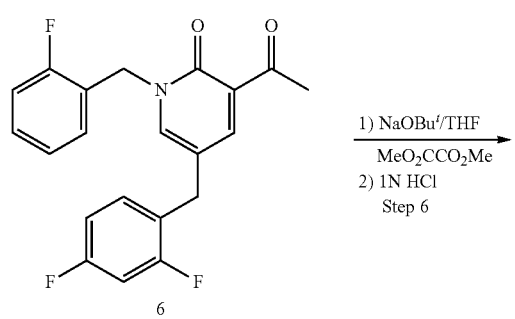
6

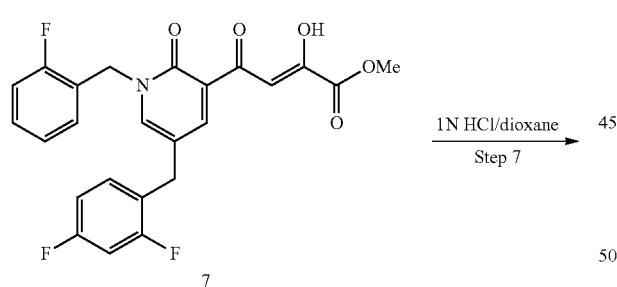
7

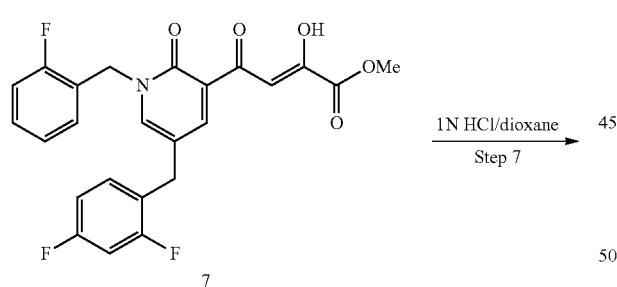
8

Step 1: Preparation of (2,4-difluorophenyl)(6-methoxypyridin-3-yl)methanol (2)

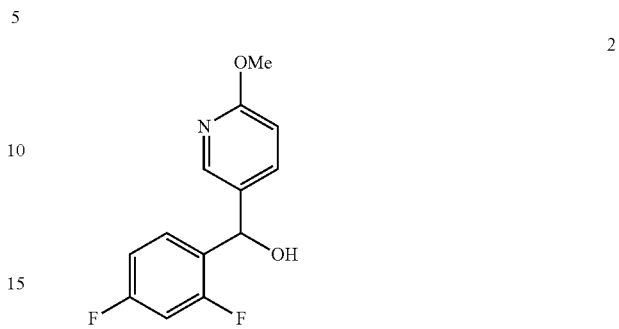
2

To a mixture of 5-bromo-2-methoxypyridine 1 (2.10 g, 10.6 mmol) in anhydrous TBME (20 ml) at −32° C. under argon atmosphere was added n-BuLi solution (5.8 ml of 2 M solution in cyclohexane, 11.7 mmol) drop wise over 15 min under argon condition. After stirring for 1 h, 2,4-difluorobenzaldehyde (1.54 g, 10.6 mmol) was added drop wise over 15 min and the reaction mixture was stirred for 30 min under −32° C. under argon atmosphere. Reaction mixture was allowed to warm up to 0° C. and quenched with saturated NH$_4$Cl (20 ml). The phases were separated and the aqueous layer was extracted with TBME (20 ml and 10 ml). All combined organic phases were washed with water (50 ml), and dried over anhydrous sodium sulfate. The solvent was evaporated in vacuo and the residue was purified by flash column chromatography on silica gel (hexanes:ethyl acetate, 85:15). Yield 2.28 g (850%). $^1$H NMR (CDCl$_3$, 500 MHz): δ 8.16 (s, 1H), 7.57-7.52 (m, 2H), 6.93-6.76 (m, 2H), 6.72 (d, 1H, J=9.0 Hz), 6.07 (d, 1H, J=3.5 Hz), 3.92 (s, 3H). $^{13}$C NMR (CDCl$_3$, 125 MHz): δ 163.9, 162.4, 159.6, 145.0, 137.2, 131.0, 128.2, 126.5, 111.5, 110.9, 103.9, 67.3, 53.6.

Step 2: Preparation of 5-(2,4-difluorobenzyl)pyridin-2(1H)-one (3)

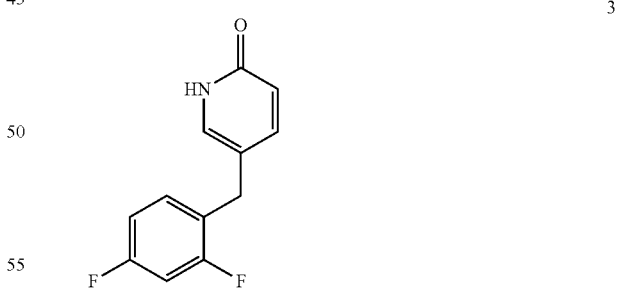
3

A mixture of (2,4-difluoro-phenyl)-(6-methoxy-pyridin-3-yl)methanol 2 (2.28 g, 9.1 mmol), sodium iodide (5.45 g, 36.4 mmol), triethylsilane (2.2 ml, 13.6 mmol) in anhydrous acetonitrile (21 ml) and was stirred at room temperature. TFA (1.1 ml, 14.3 mmol) was added at a rate that maintained the temperature below 30° C.; TMSCl (5.8 ml, 45.5 mmol) was added, and the batch was heated at 70° C. for 3 h. Upon cooling to 55° C., a 0.8 M Na$_2$SO$_3$ (11.4 ml) was added, and the reaction mixture was concentrated in vacuo to 20 ml. A solution of 0.15 M Na$_2$SO$_3$ (11.4 ml) was added, the mixture was stirred at room temperature overnight. A solution of 1.4 M K$_2$CO$_3$ (13.6 ml) was added and cooled to 0° C. The crude product was extracted with ethyl acetate (60 ml) and washed with 0.15 M Na$_2$SO$_3$ (20 ml) and water (60 ml) and dried over anhydrous sodium sulfate. The mixture was distilled, and the residue was purified by flash column chromatography on silica gel (chloroform:methanol, 90:10). Yield 1.89 g (94%). $^1$H NMR (CDCl$_3$, 500 MHz): δ 13.35 (s, 1H), 7.36-6.79 (m, 7H), 6.53 (d, 1H, J=9.2 Hz), 3.71 (s, 2H). $^{13}$C NMR (CDCl$_3$, 125 MHz): δ 164.7, 162.4, 160.4, 143.2, 132.7, 131.2, 122.3, 120.3, 118.4, 111.4, 104.1, 30.3.

Step 3: Preparation of 5-(2,4-difluorobenzyl)-3-iodopyridin-2(1H)-one (4)

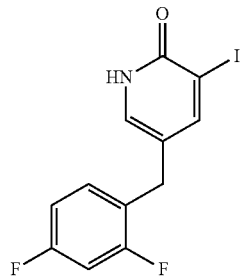

4

To a solution of 5-(2,4-difluorobenzyl)pyridin-2(1H)-one 3 (1.89 g, 8.5 mmol) in acetic acid (34 ml) was added TFA (2.2 ml), followed by N-iodosuccinimide (2.02 g, 8.5 mmol). The red homogeneous solution was allowed to stir overnight at room temperature, poured onto ice and neutralized with conc. NH$_4$OH. The solid was collected by filtration, rinsed with water, treated with methanol/dichloromethane, dried over sodium sulfate, and evaporated. The resulting brown solid was purified by flash column chromatography on silica gel (hexanes:ethyl acetate, 50:50). Yield 2.57 g (87%). $^1$H NMR (CDCl$_3$, 500 MHz): δ 13.20 (s, 1H), 7.98 (d, 1H, J=2.2 Hz), 7.26-6.81 (m, 4H), 3.70 (s, 2H). $^{13}$C NMR (CDCl$_3$, 125 MHz): δ 162.5, 161.9, 160.5, 151.9, 133.5, 131.2, 121.8, 120.0, 111.6, 104.3, 91.6, 29.9.

Step 4: Preparation of 5-(2,4-difluorobenzyl)-1-(2-fluorobenzyl)-3-iodopyridin-2(1H)-one (5)

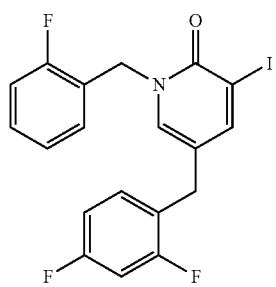

5

To a suspension of 5-(2,4-difluorobenzyl)-3-iodopyridin-2(1H)-one 4 (5.58 g, 16.1 mmol) in anhydrous DMF (160 ml) was added at room temperature NaH (60% suspension in mineral oil, 0.71 g, 17.7 mmol). After the mixture was stirred for 15 min, o-fluorobenzyl bromide (2 ml, 16.1 mmol) was added to the mixture, which was stirred for 2 h at RT. The solvent was distilled off and the residue was dissolved in ethyl acetate (200 ml), washed with water (200 ml), brine (200 ml), and dried over anhydrous sodium sulfate and the solvent was distilled off. The residue was purified by flash chromatography on silica gel (hexanes:ethyl acetate, 80:20). Yield 6.61 g (90%). $^1$H NMR (CDCl$_3$, 500 MHz): δ 7.80 (d, 1H, J=2.2 Hz), 7.55-7.51 (m, 1H), 7.32-7.27 (m, 2H), 7.13-7.04 (m, 3H), 6.86-6.79 (m, 2H), 5.14 (s, 2H), 3.64 (s, 2H). $^{13}$C NMR (CDCl$_3$, 125 MHz): δ 162.4, 162.1, 160.5, 160.2, 159.1, 149.8, 136.5, 132.1, 131.1, 130.3, 124.6, 122.5, 121.9, 118.6, 115.4, 111.5, 104.2, 93.5, 48.5, 30.0.

Step 5: Preparation of 3-acetyl-5-(2,4-difluorobenzyl)-1-(2-fluorobenzyl)pyridin-2(1H)-one (6)

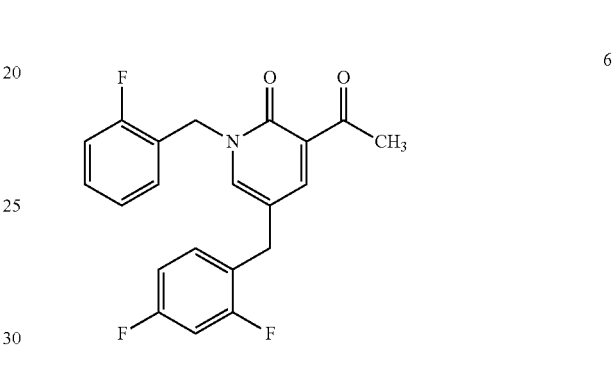

6

A mixture of 5-(2,4-difluorobenzyl)-1-(2-fluorobenzyl)-3-iodopyridin-2(1H)-one 5 (6.61 g, 14.5 mmol), bis(triphenylphosphine)palladium(II) chloride (1.02 g, 1.5 mmol), and ethoxyvinyl(tributyl)tin (10.81 g, 29.0 mmol) in anhydrous DMF (145 ml) was heated at 700 under argon condition for 1 h. DMF was distilled off and the resulting residue was dissolved in ethyl acetate (145 ml) and filtered through a pad of celite. The filtrate was stirred with 1N HCl (145 ml) for 15 min, washed with water (2×145 ml), brine (145 ml), dried over anhydrous sodium sulfate, and distilled off. The residue was purified by flash column chromatography on silica gel (hexanes:ethyl acetate, 80:20). Yield 4.21 g (78%). $^1$H NMR (CDCl$_3$, 500 MHz): δ 7.98 (d, 1H, J=2.6 Hz), 7.49-7.44 (m, 2H), 7.35-7.30 (m, 1H), 7.16-7.07 (m, 3H), 6.85-6.78 (m, 2H), 5.17 (s, 2H), 3.71 (s, 2H), 2.67 (s, 3H). $^{13}$C NMR (CDCl$_3$, 125 MHz): δ 197.6, 162.4, 162.1, 160.5, 160.4, 160.2, 144.4, 141.4, 131.4, 131.2, 130.4, 127.7, 124.6, 122.6, 122.1, 116.9, 115.6, 111.5, 104.1, 47.2, 30.9, 30.5.

Step 6: Preparation of methyl 4-(5-(2,4-difluorobenzyl)-1-(2-fluorobenzyl)-2-oxo-1,2-dihydropyridin-3-yl)-2-hydroxy-4-oxobut-2-enoate (7)

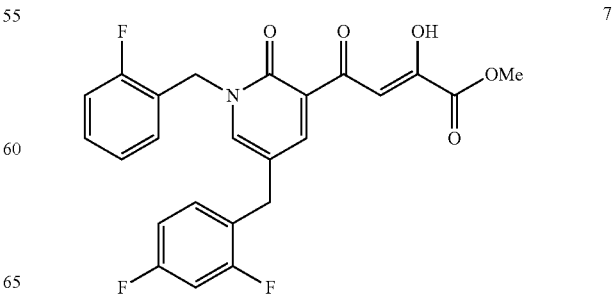

7

To a stirred solution of sodium t-butoxide (4.49 g, 45.3 mmol) in anhydrous THF (230 ml) was added dimethyl oxalate (5.41 g, 45.3 mmol) in anhydrous THF (60 ml) under argon condition. The mixture was stirred at room temperature for 30 min and a solution of 3-acetyl-5-(2,4-difluorobenzyl)-1-(2-fluorobenzyl)pyridin-2(1H)-one 6 (4.21 g, 11.3 mmol) in THF (60 ml) was added. The reaction mixture was stirred at room temperature for 3 h and then cooled in ice bath, and then 1N HCl (230 ml) was added in one portion. The crude product was extracted with ethyl acetate (2×230 ml). The combined organic layers were washed with saturated brine (2×230 ml) and ethyl acetate was distilled off to give a brown residue, which was triturated with methanol. The product was obtained by vacuum filtration. Yield 2.59 g (50%). $^1$H NMR (CDCl$_3$, 500 MHz): δ 8.18 (d, 1H, J=3.1 Hz), 7.89 (s, 1H), 7.53 (s, 1H), 7.49-7.46 (s, 1H), 7.35-7.31 (s, 1H), 7.16-7.07 (m, 3H), 6.87-6.80 (m, 2H), 5.20 (s, 2H), 3.90 (s, 3H), 3.75 (s, 2H). $^{13}$C NMR (CDCl$_3$, 125 MHz): δ 185.0, 171.9, 162.8, 162.6, 162.2, 160.6, 160.2, 159.6, 144.8, 142.0, 131.7, 131.2, 130.6, 124.8, 123.6, 122.4, 121.9, 117.7, 115.7, 111.7, 104.3, 101.8, 53.2, 47.6, 30.6.

Step 7: Preparation of 4-(5-(2,4-difluorobenzyl)-1-(2-fluorobenzyl)-2-oxo-1,2-dihydropyridin-3-yl)-2-hydroxy-4-oxobut-2-enoic acid (8)

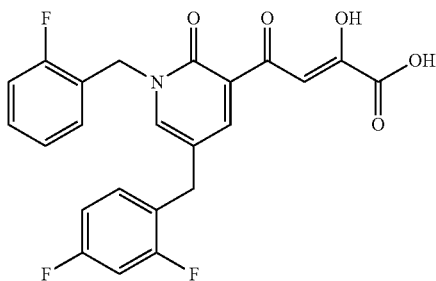

8

To a stirred solution of methyl 4-(5-(2,4-difluorobenzyl)-1-(2-fluorobenzyl)-2-oxo-1,2-dihydropyridin-3-yl)-2-hydroxy-4-oxobut-2-enoate 7 (2.59 g, 5.7 mmol) in 1,4-dioxane (125 ml) was added 1N HCl (63 ml). The reaction mixture was allowed to stir at 95° C. for 2 h. The crude product was extracted with ethyl acetate (250 ml). The solvent was evaporated under reduced pressure. The solid was crystallized in chloroform and filtered under reduced pressure. Yield 1.61 g (64%). Yellow solid, mp 187-189° C., UV (MeOH) 394 nm (ε 14,917), 320 (ε 5671). $^1$H NMR (CDCl$_3$-MeOH-d$_4$, 500 MHz): δ 8.17 (d, 1H, J=3.4 Hz), 7.88 (s, 1H), 7.54 (s, 1H), 7.48-7.45 (m, 1H), 7.36-7.30 (m, 1H), 7.17-7.07 (m, 3H), 6.87-6.81 (m, 2H), 5.19 (s, 2H), 3.76 (s, 2H). $^{13}$C NMR (DMSO-d$_6$, 125 MHz): δ 184.5, 173.3, 163.2, 161.7, 161.2, 159.8, 158.6, 144.6, 131.9, 130.0, 129.8, 124.5, 123.1, 123.0, 121.5, 116.8, 115.4, 111.6, 103.9, 100.8, 47.3, 29.2. HRMS [M+H]$^+$ calculated mass 444.1059 for C$_{23}$H$_{17}$F$_3$NO$_5$. found 444.1042.

Examples of Synthesis of Carboxamides from Diketoacid Precursor

Representative Example 1

(1S,2S)-4-(5-(2,4-difluorobenzyl)-1-(2-fluorobenzyl)-2-oxo-1,2-dihydropyridin-3-yl)-2-hydroxy-N-(2-hydroxycyclopentyl)-4-oxobut-2-enamide (9)

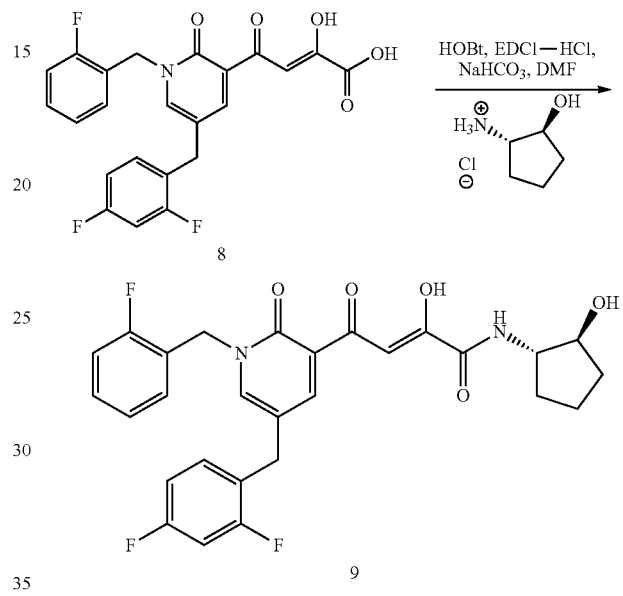

To a chilled solution of the 4-(1-(2-fluorobenzyl)-5-(4-fluorobenzyl)-2-oxo-1,2-dihydropyridin-3-yl)-2-hydroxy-4-oxobut-2-enoic acid 8 (150 mg, 0.338 mmol) in dimethylformamide (DMF) (2.0 mL), was added hydroxybenzotriazole (HOBT) (50 mg, 0.372 mmol), followed by 1-(3-dimethylaminopropyl)-3-ethylcarbodiimide hydrochloride EDCI-HCl (71 mg, 0.372 mmol). The resulting mixture was stirred for 30 min. A solution of (1S,2S)-(+)-trans-2-aminocyclopentanol hydrochloride and NaHCO$_3$ (31 mg, 0.372 mmol) was added. The resulting mixture was stirred for 2 h at 0-5° C. Thin layer chromatography (TLC) analysis indicated completion, hence cold water was added to the reaction mixture and then extracted with ethyl acetate (2×20 mL). The combined organic phase was separated and washed with water twice, then once with 1N HCl solution, then saturated aqueous NaHCO$_3$ solution. Concentration in vacuo afforded the crude product which was passed through a short plug of silica gel eluting with chloroform, the eluent was concentrated and the residual triturated with hexanes affording the product as a yellow solid in 117 mg (66.0%). The residual solvent was removed in vacuo affording pure product as a yellow solid, mp 60.0-62.9° C., [α]$^{20}_D$ +24.0 (c 0.01, MeOH), UV (MeOH) 396 nm (ε 14,455), 318 nm (ε 6327). $^1$H NMR (CDCl$_3$, 500 MHz): δ 15.33 (bs, 1H), 8.16 (d, 1H, J=2.0 Hz), 8.08 (s, 1H), 7.61-6.85 (m, 9H), 5.22 (s, 2H), 4.11 (m, 1H), 3.94 (m, 1H), 3.78 (s, 1H), 2.23 (m, 1H), 2.10 (m, 1H), 1.88 (m, 1H), 1.78 (m, 2H), 1.59 (m, 1H). $^{13}$C NMR (CDCl$_3$, 125 MHz): δ 181.3, 180.6, 163.4, 163.3, 162.4, 162.1, 162.0, 161.4, 161.3, 160.4, 160.1, 160.0, 159.2, 145.5, 143.9, 142.3, 141.6, 132.4, 132.4, 132.3, 131.5, 131.4, 131.3, 131.3, 131.2, 130.7, 130.6, 125.0, 124.9, 124.8, 122.8, 122.7, 122.5, 122.2, 122.2, 122.1, 122.1, 117.1, 115.9, 115.7, 115.6, 111.9, 111.9, 111.8, 111.7, 104.7, 104.5, 104.3, 98.3, 79.5, 79.3, 61.0, 60.6, 51.5, 47.7, 47.3, 32.9, 32.8, 32.7, 30.8, 30.7, 30.5, 21.7, 21.5. HRMS (M+H)$^+$ calculated mass 527.1794 for $C_{28}H_{26}F_3N_2O_5$. found 527.1799.

Representative Example 2

(1R,2R)-4-(5-(2,4-difluorobenzyl)-1-(2-fluorobenzyl)-2-oxo-1,2-dihydropyridin-3-yl)-2-hydroxy-N-(2-hydroxycyclopentyl)-4-oxobut-2-enamide (10)

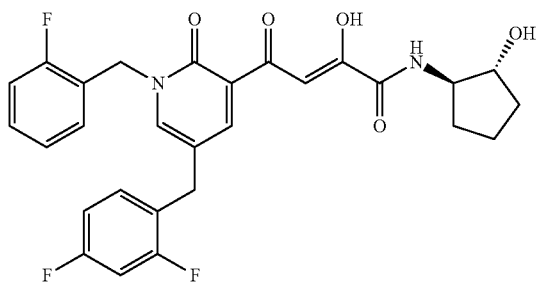

10

The titled compound was synthesized using the procedure described above using compound 8. The coupling compound, (1R,2R)-2-aminocyclopentanol hydrochloride, was synthesized by modification of the following procedure: Overman L. E.; Sugai, S., *J. Org. Chem.* 50, 4154-4155 (1985). The product was a yellow solid, mp 55-57° C., $[\alpha^{20}_D]$ –28.5 (c 0.1, MeOH), UV (MeOH) 396 nm ($\epsilon$ 14,100), 319 nm ($\epsilon$ 7444). $^1$H NMR (CDCl$_3$, 500 MHZ): δ 15.41 (bs, 1H), 8.16 (s, 1H), 8.07 (s, 1H), 7.60-6.84 (m, 9H), 5.21 (s, 2H), 4.10-3.76 (m, 5H), 2.25-1.73 (m, 6H). $^{13}$C NMR (CDCl$_3$, 125 MHZ): δ 181.1, 163.0, 162.1, 160.2, 159.0, 143.7, 141.4, 132.1, 132.1, 132.1, 131.2, 131.1, 131.1, 131.0, 130.5, 130.4, 124.7, 124.7, 122.5, 122.4, 122.3, 121.8, 116.9, 115.5, 115.3, 111.7, 111.7, 111.5, 111.5, 104.4, 104.2, 104.0, 98.1, 79.1, 60.2, 47.5, 32.5, 30.5, 30.4, 21.4. HRMS (M+H)$^+$ calculated mass 527.1794 for $C_{28}H_{26}F_3N_2O_5$. found 527.1804.

Representative Example 3

(1R,2R)-4-(1-(2-fluorobenzyl)-5-(4-fluorobenzyl)-2-oxo-1,2-dihydropyridin-3-yl)-2-hydroxy-N-(2-hydroxycyclopentyl)-4-oxobut-2-enamide (12)

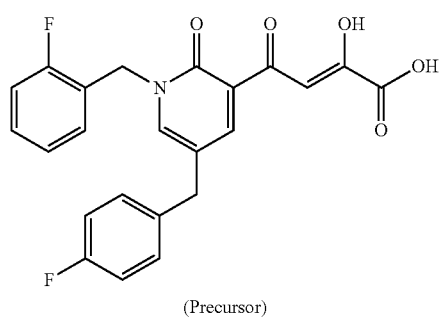

(Precursor)

The precursor, 4-[5-(4-fluoro-benzyl)-1-(2-fluoro-benzyl)-2-oxo-1,2-dihydro-pyridin-3-yl]-2-hydroxy-4-oxo-but-2-enoic acid (11), was prepared following procedure described above for 8 to give 11 as a yellow solid, mp 182-184° C., UV (MeOH) 395 nm n ($\epsilon$ 14,389), 319 nm ($\epsilon$ 6066). $^1$H NMR (CDCl$_3$/MeOH-d$_4$, 500 MHz): δ 8.14 (d, 1H, J=2.6 Hz), 7.88 (s, 1H), 7.48-7.00 (m, 9H), 5.19 (s, 2H), 3.76 (s, 2H). $^{13}$C NMR (CDCl$_3$/MeOH-d$_4$, 125 MHz): δ 185.0, 172.7, 163.8, 162.9, 162.2, 160.9, 160.2, 159.7, 144.9, 141.6, 134.4, 131.7, 130.6, 130.2, 124.8, 123.8, 122.4, 119.1, 115.8, 115.7, 101.7, 47.5, 36.8. HRMS (M+H)$^+$ calculated mass 426.1153 for $C_{23}H_{18}F_2NO_5$. found 426.1187.

(1R,2R)-4-(1-(2-fluorobenzyl)-5-(4-fluorobenzyl)-2-oxo-1,2-dihydropyridin-3-yl)-2-hydroxy-N-(2-hydroxycyclopentyl)-4-oxobut-2-enamide (12)

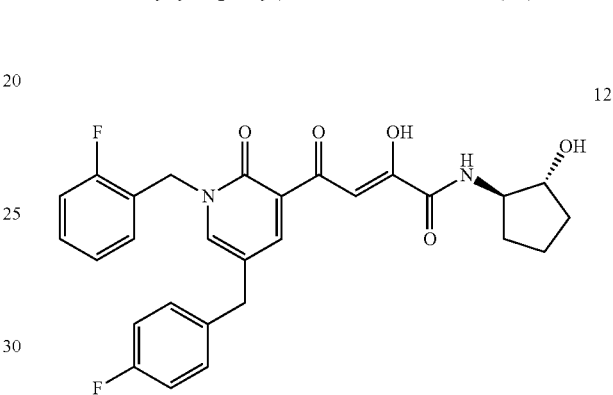

Target compound 12 was prepared from 11 using the procedure described above for 9 to give 12 as a yellow solid, mp 67-69° C., $[\alpha^{20}_D]$ –28.3, (c 0.12, MeOH), UV (MeOH) 395 nm ($\epsilon$ 12,638), 318 nm ($\epsilon$ 6759). $^1$H NMR (CDCl$_3$, 500 MHZ): δ 15.35 (bs, 1H), 8.13 (d, 1H, J=3.0 Hz), 8.08 (s, 1H), 7.61-7.03 (m, 10H), 5.21 (s, 2H), 4.10-3.76 (m, 5H), 2.25-1.57 (m, 6H). $^{13}$C NMR (CDCl$_3$, 125 MHZ): δ 181.1, 163.0, 162.7, 162.1, 160.8, 160.1, 159.0, 143.9, 141.3, 141.3, 134.4, 134.4, 132.1, 132.1, 130.4, 130.4, 130.2, 130.1, 130.1, 124.7, 124.7, 124.7, 122.5, 122.5, 122.4, 118.3, 115.8, 115.6, 115.5, 115.3, 98.1, 79.0, 60.5, 47.4, 36.7, 32.5, 30.3, 21.3. HRMS (M+H)$^+$ calculated mass 509.1888 for $C_{28}H_{27}F_2N_2O_5$. found 509.1893

Representative Example 4

(1S,2S)-4-(1-(2-fluorobenzyl)-5-(4-fluorobenzyl)-2-oxo-1,2-dihydropyridin-3-yl)-2-hydroxy-N-(2 hydroxycyclopentyl)-4-oxobut-2-enamide (13)

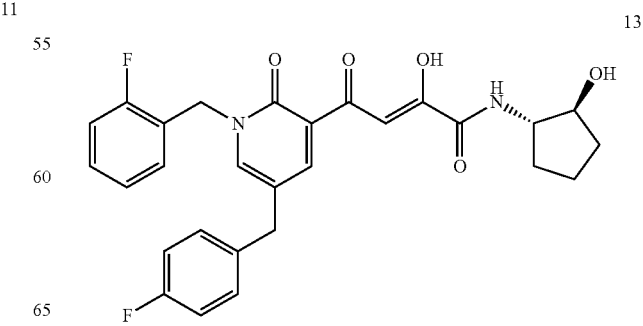

Target compound 13 was prepared from 11 using the procedure described above for 9 to give 13 as a yellow solid, mp 79-80° C., $[\alpha]^{20}_D$ +33.0 (c 0.25, MeOH), UV (MeOH) 395 nm (ε 9,000), 318 nm (ε 4923). $^1$H NMR (CDCl$_3$, 500 MHz): δ 15.31 (bs, 1H), 8.12 (s, 1H), 8.05 (s, 1H), 7.57-7.02 (m, 10H), 5.20 (s, 2H), 4.10 (m, 1H), 3.94 (m, 1H), 3.774 (s, 2H), 2.23 (m, 1H), 2.094 (m, 1H), 1.866 (m, 1H), 1.75 (m, 2H), 1.59 (m, 1H). $^{13}$C NMR (CDCl$_3$, 125 MHz); δ 181.1, 163.1, 162.8, 162.2, 160.9, 160.2, 159.1, 143.9, 141.3, 134.5, 134.4, 132.2, 132.2, 130.5, 130.4, 130.2, 130.1, 124.8, 124.7, 122.6, 122.5, 122.4, 118.3, 115.9, 115.7, 115.6, 115.4, 98.2, 79.2, 77.3, 77.1, 76.8, 60.7, 47.5, 36.8, 32.6, 30.5, 21.4. HRMS (M+H)$^+$ calculated mass 509.1888 for C$_{28}$H$_{27}$F$_2$N$_2$O$_5$. found 509.1882.

Representative Example 5

(1S,2S)-4-(5-(2,4-difluorobenzyl)-1-(4-fluorobenzyl)-2-oxo-1,2-dihydropyridin-3-yl)-2-hydroxy-N-(2-hydroxycyclopentyl)-4-oxobut-2-enamide (15)

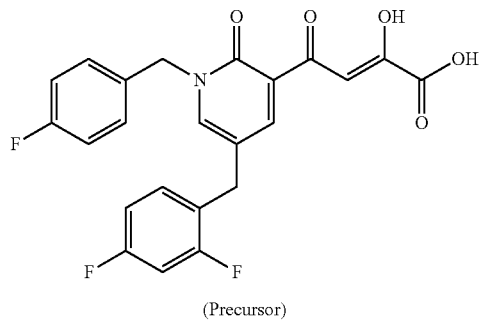

(Precursor)

The precursor compound 14 was synthesized as described above for precursor 8 to give 14 as a yellow solid, mp 197-198° C., UV (MeOH) 396 nm (ε 14070), 319 nm (ε 6226). $^1$H NMR (DMSO-d$_6$, 500 MHz): δ 15.18 (bs, 1H), 14.02 (bs, 1H), 8.33 (d, 1H, J=2.0 Hz), 8.18 (d, 1H, J=2.5 Hz), 7.83 (s, 1H), 7.46-7.07 (m, 7H), 5.19 (s, 1H), 3.84 (s, 2H). $^{13}$C NMR (DMSO-d$_6$, 125 MHz): δ 185.2, 173.7, 163.7, 163.1, 162.7, 162.6, 161.7, 161.6, 161.1, 160.7, 160.6, 159.8, 159.7, 159.1, 144.9, 144.8, 133.2, 133.2, 132.4, 132.3, 132.3, 132.3, 130.6, 130.6, 130.5, 123.6, 123.6, 123.5, 123.5, 122.0, 117.5, 115.9, 115.7, 112.2, 112.1, 112.0, 112.0, 104.6, 104.4, 104.2, 101.4, 52.1, 29.7.

(1S,2S)-4-(5-(2,4-difluorobenzyl)-1-(4-fluorobenzyl)-2-oxo-1,2-dihydropyridin-3-yl)-2-hydroxy-N-(2-hydroxycyclopentyl)-4-oxobut-2-enamide (15)

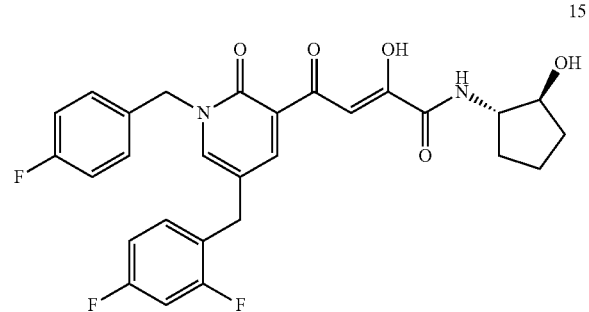 [SMILES: O=C(N[C@H]1CCC[C@@H]1O)/C(O)=C/C(=O)c1cc(Cc2ccc(F)cc2F)cn(Cc2ccc(F)cc2)c1=O]

Target compound 15 was prepared from 14 using the procedure described above for 9 to give 15 as a yellow solid, mp 88-90° C., $[\alpha]^{20}_D$ +28.8 (c 0.27, MeOH), UV (MeOH) 399 nm (ε 11,600), 318 nm (ε 6516). $^1$H NMR (CDCl$_3$, 500 MHz): δ 8.16 (s, 1H), 8.09 (s, 1H), 7.41 (s, 1H), 7.36-6.84 (m, 7H), 5.16 (s, 2H), 4.11-4.08 (m, 1H), 3.96-3.90 (m, 1H), 3.75 (s, 2H), 2.26-2.21 (m, 1H), 2.11-2.06 (m, 1H), 1.90-1.70 m, 4H). $^{13}$C NMR (CDCl$_3$, 125 MHz): δ 181.3, 180.2, 163.7, 163.2, 163.1, 161.9, 161.8, 161.7, 161.2, 161.2, 160.0, 159.9, 158.9, 145.3, 143.7, 141.6, 140.5, 131.5, 131.5, 131.2, 131.1, 131.1, 131.0, 130.3, 130.2, 130.1, 129.9, 129.9, 122.8, 122.0 121.9, 121.8, 121.8, 117.1, 116.1, 115.9, 111.8, 111.7, 111.6, 111.6, 104.5, 104.3, 104.1, 98.2, 79.3, 79.1, 60.8, 52.3, 32.7, 32.4, 30.7, 30.5, 30.2, 21.5, 21.2. HRMS (M+H)$^+$, calculated mass 527.1794 for C$_{28}$H$_{26}$F$_3$N$_2$O$_5$. found 527.1779.

Representative Example 6

(1R,2R)-4-(5-(2,4-difluorobenzyl)-1-(4-fluorobenzyl)-2-oxo-1,2-dihydropyridin-3-yl)-2-hydroxy-N-(2-hydroxycyclopentyl)-4-oxobut-2-enamide (16)

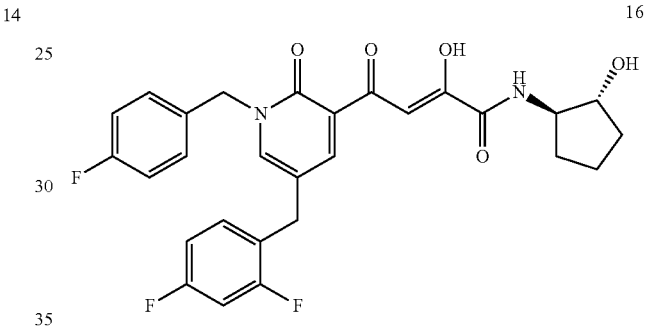

Target compound 16 was prepared from 14 using the procedure described above for 9 to give 16 as a yellow solid, mp 85-86° C., $[\alpha]^{20}_D$ −28.9 (c 0.19, MeOH), UV (MeOH) 398 nm, (ε 12,800), 321 nm (ε 6459). $^1$H NMR (CDCl$_3$, 500 MHz): δ 8.15 (s, 1H), 8.07 (s, 1H), 7.42 (s, 1H), 7.35-6.84 (m, 7H), 5.15 (s, 2H), 4.11 (m, 1H), 3.93 (m, 1H), 3.75 (s, 2H), 2.23 (m, 1H), 2.08 (m, 1H), 1.85-1.58 (m, 4H). $^{13}$C NMR (CDCl$_3$, 125 MHz): δ 181.3, 163.7, 163.1, 161.7, 159.0, 143.7, 140.6, 131.5, 131.5, 131.2, 131.1, 131.1, 131.0, 130.3, 130.2, 122.8, 121.9, 117.1, 116.1, 115.9, 111.8, 111.7, 111.6, 111.6, 104.5, 104.3, 104.1, 98.2, 79.2, 77.3, 77.1, 76.8, 60.7, 52.3, 32.6, 30.7, 30.5, 21.4, 21.2 . HRMS (M+H)$^+$ calculated mass 527.1794 for C$_{28}$H$_{26}$F$_3$N$_2$O$_5$. found 527.1794.

Representative Example 7

4-(5-(2,4-difluorobenzyl)-1-(2-fluorobenzyl)-2-oxo-1,2-dihydropyridin-3-yl)-2-hydroxy-4-oxo-N-(2-oxopyrrolidin-1-yl)but-2-enamide (17)

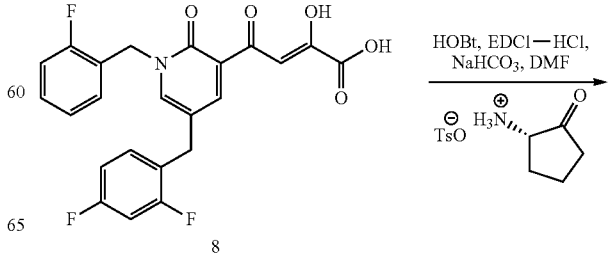

8

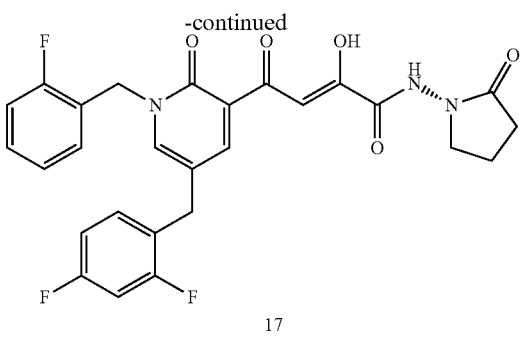

17

To a chilled solution of the 4-(1-(2-fluorobenzyl)-5-(4-fluorobenzyl)-2-oxo-1,2-dihydropyridin-3-yl)-2-hydroxy-4-oxobut-2-enoic acid 8 (150 mg, 0.338 mmol) in dimethylformamide (DMF) (2.0 mL), was added hydroxybenzotriazole (HOBT) (50 mg, 0.372 mmol), followed by 1-(3-dimethylaminopropyl)-3-ethylcarbodiimide hydrochloride EDCI-HCl (71 mg, 0.372 mmol). The resulting mixture was stirred for 30 min. To the above solution was added 1-(amino)-2-pyrollidinone, p-toluene sulfonate (101 mg, 0.372 mmol) and NaHCO$_3$ (31 mg, 0.372 mmol) was added. The resulting mixture was stirred for 2 h at 0-5° C. Thin layer chromatography (TLC) analysis indicated completion, hence cold water was added to the reaction mixture and then extracted with ethyl acetate (2×20 mL). The combined organic phase was separated and washed with water twice, then once with 1N HCl solution, then saturated aqueous NaHCO$_3$ solution. Concentration in vacuo afforded the crude product (148 mg, 86%), which was passed through a short plug of silica gel eluting with chloroform, the eluent was concentrated and the residual triturated with pentane, filtered then dried affording the product in 105 mg (61.0%). The product was a yellow solid, mp 86.0-88.0° C., UV (MeOH) 399 nm (ε 8758), 319 nm (ε 6,770). $^1$H-NMR (CDCl$_3$, 500 MHz): δ 15.25 (bs, 1H), 8.85 (s, 1H), 8.16 (s, 1H), 8.03 (s, 1H), 7.57-6.85 (m, 9H), 5.21 (s, 2H), 3.78-3.71 (m, 4H), 2.51 (m, 2H), 2.20 (m, 2H). $^{13}$C-NMR (CDCl$_3$, 125 MHz): δ 181.4, 179.5, 173.6, 163.4, 162.4, 162.0, 161.4, 161.3, 160.4, 160.1, 160.0, 159.6, 144.2, 141.8, 132.4, 131.4, 131.3, 131.3, 130.7, 130.6, 124.9, 124.9, 122.8, 122.6, 122.5, 122.2, 122.2, 122.0, 117.1, 115.8, 115.6, 111.9, 111.9, 111.7, 104.7, 104.5, 104.3, 98.8, 48.0, 47.7, 30.8, 28.6, 17.0. HRMS (M+H)$^+$ calculated mass 526.1590 for C$_{27}$H$_{23}$F$_3$N$_3$O$_5$. found 526.1578.

Representative Example 8

4-(5-(2,6-difluorobenzyl)-1-(2-fluorobenzyl)-2-oxo-1,2-dihydropyridin-3-yl)-2-hydroxy-4-oxo-N-(2-oxopyrrolidin-1-yl)but-2-enamide (18)

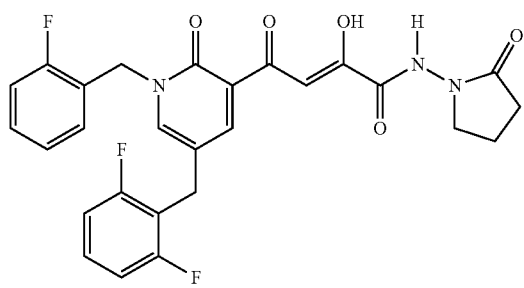

18

Target compound 18 was prepared from the corresponding trifluoro diketo acid using the procedure described above for 17 to give 18 as a yellow solid, mp 175-176° C. (amorphous powder), UV (methanol), λ$_{max}$ 401 nm (ε 9139), λ$_{max}$ 318 nm (ε 6225). $^1$H-NMR (CDCl$_3$, 500 MHz), δ 8.88 (s, 1H), 8.24 (s, 1H), 8.01 (s, 1H), 7.65 (s, 1H), 7.55 (t, J$_1$=2 Hz, J$_2$=2.5 Hz, 1H), 7.33-7.10 (m, 5H), 6.94 (t, J$_1$=7.5 Hz, J$_2$=8 Hz, 2H), 5.21 (s, 2H), 3.83 (s, 2H), 3.71 (t, J$_1$=7 Hz, J$_2$=7.5 Hz, 2H), 2.50 (t, J$_1$=7.5 Hz, J$_2$=8 Hz, 2H), 2.19 (m, 2H); $^{13}$C-NMR (CDCl$_3$, 125 MHz), δ 181.2, 179.3, 173.4, 162.2, 162.1, 162.1, 160.2, 160.2, 160.1, 159.5, 159.0, 144.0, 141.7, 132.1, 132.0, 130.4, 130.4, 128.9, 128.8, 124.7, 124.8, 122.5, 122.4, 122.3, 116.6, 115.6, 115.4, 115.0, 111.7, 111.6, 111.5, 111.4, 98.5, 47.8, 47.4, 28.4, 24.3, 16.8. HRMS [M+H]$^+$ calculated mass 526.1590 for C$_{27}$H$_{23}$F$_3$N$_3$O$_5$. found 526.1589.

Representative Example 9

4-(5-(2,4-difluorobenzyl)-1-(4-fluorobenzyl)-2-oxo-1,2-dihydropyridin-3-yl)-2-hydroxy-4-oxo-N-(2-oxopyrrolidin-1-yl)but-2-en amide (19)

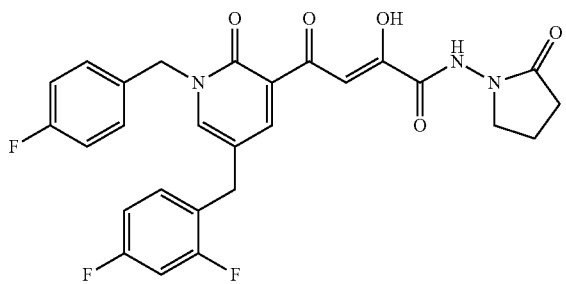

19

Target compound 19 was prepared from 14 using the procedure described above for 17 to give 19 as a yellow solid, mp 87-88° C., UV (MeOH) 400 nm (ε 8500), 320 nm (ε 6472). $^1$H NMR (CDCl$_3$, 500 MHz): δ 8.90 (s, 1H), 8.16 (s, 1H), 8.04 (s, 1H), 7.43 (s, 1H), 7.35-6.85 (m, 7H) 5.16 (s, 2H), 3.75 (s, 2H), 3.71 (m, 2H), 2.5 (m, 2H), 2.19 (m, 2H). $^{13}$C NMR (CDCl$_3$, 125 MHz): δ 181.0, 179.5, 173.5, 163.7, 163.2, 163.1, 161.9, 161.8, 161.7, 161.2, 161.1, 159.9, 159.8, 159.4, 159.0, 143.9, 140.8, 131.5, 131.4, 131.2, 131.14, 131.11, 131.06, 130.25, 130.19, 122.7, 121.96, 121.94, 121.84, 121.81, 117.2, 116.1, 115.9, 115.8, 111.8, 111.7, 111.6, 111.58, 104.5, 104.3, 104.1, 98.6, 52.3, 47.8, 30.7, 28.4, 28.3, 16.8. HRMS [M+H]$^+$ calculated mass 526.1590 for C$_{27}$H$_{23}$F$_3$N$_3$O$_5$. found 526.1590.

Representative Example 10

4-(1,5-bis(2,4-difluorobenzyl)-2-oxo-1,2-dihydropyridin-3-yl)-2-hydroxy-4-oxo-N-(2-oxopyrrolidin-1-yl)but-2-enamide (20)

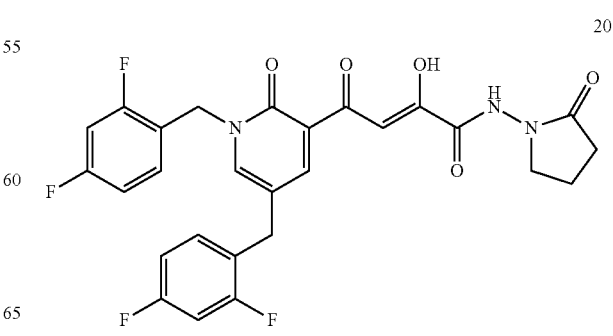

20

Target compound 20 was prepared from the corresponding tetrafluoro diketo acid using the procedure described above for 17 to give 20 as a yellow solid, mp 82-83° C., UV (MeOH) 400 nm (ε 7500), 322 nm (ε 5400). $^1$H NMR (CDCl$_3$, 500 MHz): δ 8.93 (s, 1H), 8.16 (s, 1H), 8.15 (s, 1H), 8.00 (s, 1H), 7.63-6.85 (m, 6H), 5.15 (s, 2H), 3.78 (s, 2H), 3.72 (m, 2H), 2.50 (m, 2H), 2.19 (m, 2H). $^{13}$C NMR (CDCl$_3$, 125 MHz): δ 180.9, 179.4, 173.5, 164.1, 164.0, 163.22, 163.12, 162.4, 162.3, 162.1, 162.0, 161.9, 161.8, 161.2, 161.1, 160.4, 160.3, 160.0, 159.9, 159.5, 159.0, 144.0, 141.4, 133.6, 133.5, 133.47, 133.43, 131.2, 131.16, 131.13, 131.1, 122.6, 122.0, 121.9, 121.82, 121.79, 118.5, 118.47, 118.4, 118.35, 117.1, 112.04, 112.01, 111.9, 111.8, 111.77, 111.74, 111.6, 111.57, 104.5, 104.3, 104.15, 104.1, 103.9, 103.7, 98.6, 47.9, 47.2, 30.6, 28.4, 16.8. HRMS [M+H]$^+$ calculated mass 544.1496 for C$_{27}$H$_{22}$F$_4$N$_3$O$_5$. found 544.1541.

We claim:

1. A compound according to the structural formula I:

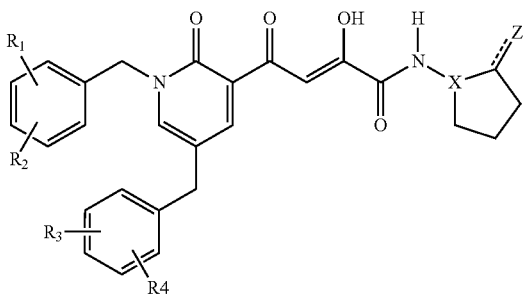

Formula I

Wherein R$_1$, R$_2$, R$_3$ and R$_4$ are each independently H or a halogen;
X is CH or N; and
Z is OH or =O, or a chiral isomer, geometric isomer, tautomer, regioisomer or a pharmaceutically acceptable salt or ester thereof.

2. A compound according to claim 1 wherein said halogen is F.

3. A compound according to claim 1 wherein R$_1$, R$_2$, R$_3$ and R$_4$ are substituted according to the following alternative sequences:
R$_1$=o-F, R$_2$=H, R$_3$ p-F, R$_4$=o-F
R$_1$=p-F, R$_2$=H, R$_3$=p-F, R$_4$=o-F
R$_1$=o-F, R$_2$=o-F, R$_3$=o-F, R$_4$=H
R$_1$=o-F, R$_2$=H, R$_3$=o-F, R$_4$=o-F o-F, R$_2$=H, R$_3$=p-F, R$_4$=H
R$_1$=o-F, R$_2$ p-F, R$_3$=p-F, R$_4$=o-F or
R$_1$=o-F, R$_2$=o-F, R$_3$=o-F, R$_4$=o-F.

4. A compound according to claim 1 wherein X is CH.
5. A compound according to claim 1 wherein X is N.
6. A compound according to claim 1 where Z is OH.
7. A compound according to claim 1 wherein Z is =O.
8. A compound according to claim 1 wherein the said compound is a pharmaceutically acceptable salt.

9. A pharmaceutical composition for treating an HIV infection, comprising a therapeutically effective amount of a compound according to claim 1 and a pharmaceutically acceptable carrier, additive or excipient.

10. The pharmaceutical composition of claim 9 wherein said composition treats said HIV infection by inhibiting HIV integrase, both wild type and mutants, in the human host.

11. A pharmaceutical composition comprising a therapeutically effective amount of a compound according to claim 1 in combination with a therapeutically effective amount of at least one compound selected from the group consisting of i) an additional anti-HIV agent, ii) an anti-infective agent other than an anti-HIV agent; and iii) an immunomodulator and a pharmaceutically acceptable carrier, additive or excipient.

12. The composition of claim 11 wherein said anti-infective agent is an antiviral agent selected from the group consisting of a protease inhibitor, a reverse transcriptase inhibitor, an additional integrase inhibitor or a combination thereof.

13. The composition of claim 12 wherein said reverse transcriptase inhibitor is a nucleoside compound.

14. The composition of claim 13 wherein said reverse transcriptase inhibitor is a non-nucleoside compound.

15. The composition of claim 12 wherein the said additional integrase inhibitor is a compound other than a pyridinone hydroxycyclopentyl carboxamide compound according to claim 1.

16. The composition according to claim 11 in oral or parenteral dosage form.

17. The composition according to claim 11 formulated for administration as an inhalation spray or a rectal suppository.

18. A method of treating an HIV infection in a patient, said method comprising administering to said patient an effective amount of a composition according to claim 11.

19. A method of reducing the likelihood of an HIV infection in a patient at risk for said infection, said method comprising administering to said patient an effective amount of a composition according to claim 11.

20. A method of treating a patient with AIDS or ARC comprising administering to said patient a therapeutically effective amount of the composition according to claim 1.

21. A method of inhibiting HIV integrase in a subject, said method comprising administering to said subject a therapeutically effective amount of a compound according to claim 1.

22. The method of claim 21 wherein said subject is a human.

23. The method according to claim 18, wherein said compound according to the structure:

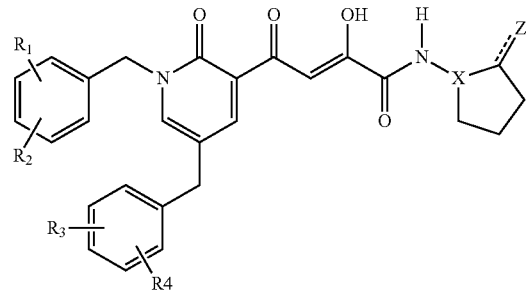

Formula I wherein R$_1$, R$_2$, R$_3$ and R$_4$ are each independently H or a halogen; X is CH or N; and Z is OH or =O or a chiral isomer, geometric isomer, tautomer, regioisomer or a pharmaceutically acceptable salt or ester thereof, is combined with a therapeutically effective amount of at least one additional compound selected from the group consisting of i) an additional anti-HIV agent, ii) an anti-infective agent other than an anti-HIV agent and iii) an immunomodulator, in combination with a pharmaceutically acceptable carrier, additive or excipient.

24. The method according to claim 20, wherein said the compound according to the structure:

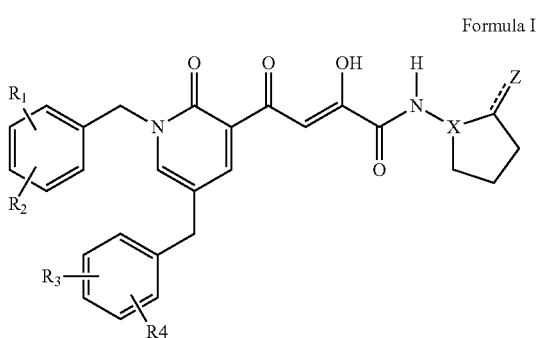

Formula I wherein R₁, R₂, R₃ and R₄ are each independently H or a halogen; X is CH or N; and Z is OH or =O or a chiral isomer, geometric isomer, tautomer, regioisomer or a pharmaceutically acceptable salt or ester thereof, is combined with a therapeutically effective amount of at least one additional compound selected from the group consisting of i) an additional anti-HIV agent, ii) an anti-infective agent other than an anti-HIV agent and iii) an immunomodulator, in combination with a pharmaceutically acceptable carrier, additive or excipient.

25. A method of treating an HIV infection in a human host comprising administering to said host in combination, an effective amount of a compound according to the structure:

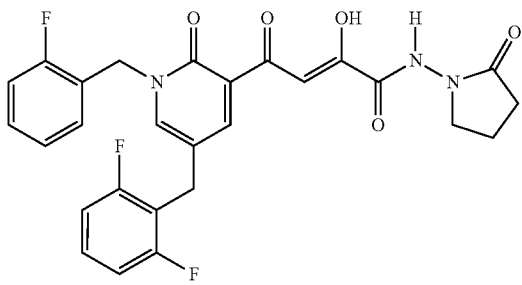 [SMILES: O=C(NN1CCCC1=O)/C(O)=C/C(=O)c1cc(Cc2c(F)cccc2F)cn(Cc2ccccc2F)c1=O]

in combination with a therapeutically effective amount of at least one additional compound selected from the group consisting of i) an additional anti-HIV agent, ii) an anti-infective agent other than an anti-HIV agent and iii) an immunomodulator, in combination with a pharmaceutically acceptable carrier, additive or excipient.

26. A pharmaceutical composition according to claim 9 further comprising at least one additional compound selected from the group consisting of
(−)bDioxolane-G; DXG
(−)b-Arctigenin; Arctigenin
(−)-Carbovir; (−)—C-D4G; (−)-Carbovir
(−)-b-D-2,6-Diaminopurine dioxolane; Amdoxovir; DAPD; APD
(+)-2′-Deoxy-3′-oxa-4′-thiocytidine; dOTC (+)
(+)-2′-Deoxy-3′-oxa-4′-thio-5-fluorocytidine; dOTFC (+)
(+/−)-Cyclobut-G; A-69992; (+/−)-Lobucavir; C-Oxt-G; Cyclobut-G; C-Oxetanocin-G
(R)-2QuinCOAsnPhe[CHOHCH2]PipCONHtBu
(R)-3,6-Diamino-N-(aminomethyl)hexanamide; Bellenamine
(R)-PMPA; (R)-9-(2-Phosphonylmethoxypropyl)adenine; PMPA-(R); Tenofovir
(R)-PMPDAP; PMPDAP-(R)
(S)-PMPA; (S)-9-(2-Phosphonylmethoxypropyl)adenine; PMPA(S)
(S)-9-(2-Phosphonylmethoxypropyl)adenine; (S)-PMPA
a-APA; R89439; Loviride
a-APA derivative; R87232
a-APA derivative; R88703
a-APA enantiomer; R90385
a-L-AZT; AZT-a-L
a-L-DXC; a-L-Dioxalane-C; DXC-a-L-
a-L-FTC; FTC-a-L-
a-Monofluoromethyldehydroornithine methyl ester; MFMOME
1,1′-Azobisformamide; ADA; Azodicarbonamide
1-(11-Octylamino-10-hydroxyundecyl)-3,7-dimethylxanthine; CT-2576
1-(2′,3′-Dideoxy-2′-fluoro-b-D-threo-pentofuranosyl)cytosine; Ro 31-6840
1-(2′-Fluoro-2′,3′-dideoxy-B-D-erythro-pentofuranosyl) thymine; 2′FddT
1-(2OHPr)-4-Substit-piperazine, thienyl carbamate derivative
1-(2OHPr)-4-Substit-piperazine, thienyl carbamate derivative
1-(2OHPr)-4-Substit-piperazine, thienyl carbamate derivative
1-(2OHPr)-4-Substit-piperazine, thienyl carbamate derivative
1-[(2-Hydroxyethoxy)methyl]-6-(3-methylphenyl)thio) thymine; HEPT-M
1-[(2-Hydroxyethoxy)methyl]-6-(phenylthio)-2-thiothymine; HEPT-S
1-[(2-Hydroxyethoxy)methyl]-6-(phenylthio)thymine; HEPT
1-Deoxynojirimycin; Deoxynojirimycin
141W94; VX-478; Amprenavir
1592U89 Succinate; Abacavir Succinate
1-Aminooxyethylamine; AEA
1-Methoxyoxalyl-3,5-dicaffeoylquinic acid; 1-MO-3,5-DCQA; Dicaffeoylquinic acid derivative
1OH-2(Cbz-Tle)3PhPr [14]paracyclophane derivative
1OH-2(Cbz-ValNH)3PhPr [13]metacyclophane derivative
1OH-2(Cbz-ValNH)3PhPr [13]paracyclophane derivative
1OH-2(Cbz-ValNH)3PhPr [14]paracyclophane derivative
1OH-2(Cbz-ValNH)3PhPr [17]paracyclophane derivative
12-Deoxyphorbol-[3-(3E,5E-decadienoate); Phorbol derivative
16-alpha-Bromoepiandrosterone; Epi-Br; Inactivin; HE2000; PPB2; DHEA derivative
1-b-D-arabinofuranosyl-5-(2-bromovinyl)uracil; BV-ara-U; BVaraU; BV ara-U; Sorivudine; SQ-32756; Bravavir; Brovavir; Usevir; YN-72; Bromovinyl araU; BVAU
2′,3′-Didehydro-3′-deoxycytidine; D4C
2′,3′-Dideoxydidehydroguanosine; D4G
2′,3′-Didehydro-3′-deoxythymidine; D4T; Stavudine
2′,3′-Dideoxy-3′-fluoro-4-thiothymidine; 3′-F-4-Thio-ddT
2′,3′-Dideoxy-3′-fluoro-5-bromouridine; FddBrU
2′,3′-Dideoxy-3′-fluoro-5-chlorocytidine; 3′-F-5-Cl-ddC
2′,3′-Dideoxy-3′-fluoro-5-chlorouridine; 935U83; 5-Chloro-2′,3′-dideoxy-3′-fluorouridine;
FddClU; Raluridine
2′,3′-Dideoxy-5-ethylcytidine; 5-Et-ddC
2′,3′-D1deoxyadenosine; D2A; ddAdo; ddA
2′,3′-Dideoxydidehydroadenosine; d4A
2′,3′-D1deoxyguanosine; D2G; ddG
2′,3′-Dideoxy-3′-hydroxymethyl cytidine; 3′-Hydroxymethyl-ddC; BEA-005

2,5'-Anhydro-3'-azido-2',3'-dideoxyuridine; AZU-2,5'-anhydro
2,5'-Anhydro-3'-azido-3'-deoxythymidine; AZT-2,5'-anhydro
2',5'diSilySpiroT; TSAO-T; 2',5'diSilySpiroT; TSAO-me^3T
2,6-Diamino-2',3'-dideoxypurine-9-ribofuranoside; ddDAPR; DAPDDR; 2,6-Diamino-ddP
2,6-Diaminopurine-2',3'-dideoxydidehydroriboside; ddeDAPR
2,6-Diaminopurine-3'-fluoro-2',3'-dideoxyriboside; 3'-F-ddDAPR
2-Aminobenzylstatine Valyl Cbz derivative; Statine derivative
2-Glycine amide-5-chlorophenyl 2-pyrryl ketone; GCPK [2-PyridCH2NCH3CO-Val-NHCH(Bz)]CHOHCHOH; A-77003
2'-Azido-2',3'-dideoxyadenosine; 9-(2'-Azido-2',3'-dideoxy-B-D-erythropentofuranosyl)adenine; 2'-N3ddA
2'-FddA(B-D-threo); F-ddA; 2'-F-dd-ara-A; 9-(2'-Fluoro-2',3'-dideoxy-B-D-threopentafuranosyl)adenine; Lodensine
2'-N3ddA (B-D-threo); 9-(2'-Azido-2',3'-dideoxy-b-threopentafuranosyl)adenine
2-NaphCOAsnPhe[CHOHCH2]Pro-OtBu
2-Nitrophenylphenylsulfone; NPPS
3-(3-Oxo-1-propenyl)-3'-azido-3'-deoxythymidine; 3-(3-Oxo-1-propenyl)AZT
3-(Phenylsulfonyl)-indole derivative; L-737,126
3,5-DCQA; 3,5-Dicaffeoylquinic acid; Dicaffeoylquinic acid
3'-Azido-2',3'-dideoxy-5-[(cyanomethyl)oxy]uridine; 3'-N3-5-Cyanomethyloxy-ddU
3'-Azido-2',3'-dideoxy-5-aminouridine; 3'-N3-5-NH2-ddU
3'-Azido-2',3'-dideoxy-5-aza-6-deazauridine; C-analog of 3'-N3-ddU
3'-Azido-2',3'-dideoxy-5-bromouridine; 3'-N3-5-Br-ddU; AZddBrU
3'-Azido-2',3'-dideoxy-5-chlorocytidine; 3'-Az-5-Cl-ddC
3'-Azido-2',3'-dideoxy-5-dimethylaminouridine; 3'-N3-5-NMe2-ddU
3'-Azido-2',3'-dideoxy-5-ethyluridine; 3'-N3-5-EtddU; CS-85; AZddEtU
3'-Azido-2',3'-dideoxy-5-fluorocytidine; 3'-N3-5-F-ddC
3'-Azido-2',3'-dideoxy-5-fluorouridine; AZddFU
3'-Azido-2',3'-dideoxy-5-hydroxyuridine; 3'-N3-5-OH-ddU
3'-Azido-2',3'-dideoxy-5-iodouridine; 3'-N3-5-1-ddU; AZddIU
3'-Azido-2',3'-dideoxy-5-methyaminouridine; 3'-N3-5-NHMe-ddU
3'-Azido-2',3'-dideoxy-5-methylcytidine; CS-92; 3'-N3-5-Me-ddC
3'-Azido-2',3'-dideoxy-5-thiocyanatouridine; 3'-N3-5-SCN-ddU
3'-Azido-2',3'-dideoxy-5-trifluoromethyluridine; 3'-N3-5-CF3-ddU
3'-Azido-2',3'-dideoxycytidine; CS-91; 3'-N3-ddC
3'-Azido-2',3'-dideoxyguanosine; AZG; 3'-N3ddG
3'-Azido-2',3'-dideoxy-N4-5-dimethylcytidine; 3'-N3-N4-5-diMe-ddC
3'-Azido-2',3'-dideoxy-N4-OH-5-methylcytidine; 3'-N3-N4-OH-5-Me-ddC
3'-Azido-2',3'-dideoxyuridine; CS-87; 3'-N3ddU; AZdU; Uravidine
3'-Azido-3'-deoxy-6-azathymidine; 3'AZ-6AzaT
3-Azido-3'-deoxythymidilyl-(5',5')-2',3'-dideoxy-5'-adenylic acid; AZT-P-ddA
3'-Azido-3'-deoxythymidilyl-(5',5)-2',3'-dideoxy-5'-adenylic acid, 2-cyanoethyl ester; AZT-P(CyE)-ddA
3'-Azido-3'-deoxythymidilyl-(5',5)-2',3'-dideoxy-5'-inosinic acid; AZT-P-ddI
3'-Azido-3'-deoxythymidine-5'-(butylmethoxyvalinyl) phosphate; 5'MeOValPO3(Bu)AZT
3'-Azido-5-chloro-2',3'-dideoxyuridine; AzddClUrd; AzddClU
3'-Deoxythymidine; ddT
3'-FddA (B-D-Erythro); 9-(3'-Fluoro-2',3'-dideoxy-B-D-erythropentafuranosyl)adenine
3'-FddC; 3'-Fluoro-2',3'-dideoxycytidine
3'-FddG; 3'-Fluoro-2',3'-dideoxyguanosine
3'-FddT; Alovudine; FddT; FddThD; 3'-FLT; FLT
3'-FddU; 3'-Fluoro-2',3'-dideoxyuridine
3'-Fluoro-2',3'-dideoxy-5-iodouridine; FddIU
3'-N3-ddA; 9-(3'-Azido-2',3'-dideoxy-B-D-erythropentafuranosyl)adenine
3TC; Lamivudine
Lamivudine & Zidovudine
4-Acetoamidophenyl-4-guadinobenzoate; AGB
4'-Az-3'-dT; 4'-Azido-3'-deoxythymidine
4'-Az-5CldU; 4'-Azido-5-chloro-2'-deoxyuridine
4'-AzdA; 4'-Azido-2'-deoxyadenosine
4'-AzdC; 4'-Azido-2'-deoxycytidine
4'-AzdG; 4'-Azido-2'-deoxyguanosine
4'-AzdI; 4'-Azido-2'-deoxyinosine
4'-AzdU; 4'-Azido-2'-deoxyuridine
4'-Azido-2'-deoxy-b-D-erythro-pentofuranosyl-5-methyl-2,4-dioxopyrimidine; 4'-Azidothymidine
4'-Cyanothymidine; 4'-CN-T
4-Methyl-5-(pyrazinyl)-3H-1,2-dithiole-3-thione; Oltipraz
5'-[(1,4-Dihydro-1-methyl-3-pyridinylcarbonyl)oxy]-3'-azido-2',3'-deoxythymidine; DP-AZT; HP-AZT; AZT Prodrug; AZT-DHP
5'-[[(Z)-4-amino-2-butenyl]methylamino]-5'-deoxyadenosine; MDL 73811
5'-Alkylglycosidecarbonate of 3'-azido-3'-deoxythymidine; AcNHGlc-hexyl-CO3 AZT
5Cl3PhS-2IndolCONH2
5-Fluoro-2',3'-dideoxycytidine; 5-F-ddC
5-Methyl-3'-azido-2',3'-dideoxyisocytidine; MeAZddIsoC
6-O-Butanoylcastanospermine; BuCast; MDL 28,574; Celgosivir
6-Chloro-9-(2,3-dideoxy-b-D-glyceropentofuranosyl)-9H-purine; D2ClP; 6-Chloro-ddP; CPDDR; 6Cl-ddP
6-Dimethylaminopurine-2',3'-dideoxyriboside; N-6-dimethylddA; DMAPDDR
7-Chloro-N-methyl-5-(1H-pyrrol-2-yl)-3H-1,4-benzodiazepin-2-amine; Ro 24-7429
7-Chloro-5-(2-pyrryl)-3H-1,4-benzodiazepin-2(H)-one; Ro 5-3335
8-Chloro-TIBO; Tivirapine; R86183
9-(2,3-Dideoxy-b-D-ribofuranosyl)-6-(methylthio)purine; D2SMeP
9-[Bis(OHMe)cBu]A; A-69463; Cyclobutyl-A; Cyclobut-A; C-oxetanocin A
A-76890
A-77212
A-80987; Ritonavir derivative
A-81525; Ritonavir derivative
A-83962; Ritonavir derivative A-98881; Azacyclic urea derivative
AA; L-ascorbic acid; Calcium Ascorbate
AAP-BHAP; U-104489; PNU-104489
Abacavir & Lamivudine & Zidovudine
ABT-378; Lopinavir
ABT-378 & ABT-538; Lopinavir & Ritonavir
ABT-538; Ritonavir
Acemannan
Adefovir; PMEA; GS-0393
Adefovir dipivoxil; BisPom PMEA; GS-840
AG-1343; Nelfinavir
AG1350; LY316957; Nelfinavir-octahydro-thienopyridine analog
AHPBA analog; R-87366
Alpha-lipoic acid; a-Lipoic acid; Thioctic acid
ALX40-4C
AMD3100; JM3100
Amprenavir phosphate; VX-175; GW433908; GW433908A (*Sodium Salt*); GW433908G (*Calcium Salt*); Fosamprenavir
Ancer 20; Z-100
Anti-sense 25-mer phosphorothioate; GEM91
Atazanavir; CGP-73547; BMS-232632; BMS 232632; Zrivada; Latazanavir
Atevirdine; U-87201E; BHAP derivative
Aurintricarboxylic acid; Dupont ATA; Dupont DA639; SD-095345; ATA
AY 9944; trans-1,4-Bis(2-dichlorobenzylaminoethyl)cyclohexane dichlorhydrate
AZT; Zidovudine; Azidothymidine
AZT-PO3(CH3)-AZT; O,O'-Bis(3'-azido-3'-deoxythymidin-5'-yl)methylphosphonate
Baicalin; TJN-151
Betulinic acid; Mairin
Betulinic acid, 3-O-(3',3'-dimethylsuccinate)
BHAP derivative
Delavirdine; U-90152
U-88204E
BI-RG-587; Nevirapine
BILA 1906 BS
BILA 2011 BS; Palinavir
BILA 2185 BS
Bis(2-nitrophenyl)sulfone; Bis(2NO2Ph)SO2; NSC633001
bis-ValHOEt-N2aza-peptide isostere; CGP 53820
bis-ValHOEt-N2aza-peptide isostere; CGP 53820 analog
BMS-186318
BocPhe[CHOH(CH2)3CH=CHPhCO]IleAMBI; L-687,908
BzOCValPhe[diCHOH(RR)]PheValBzOC
BzOCValPhe[diCHOH(SS)]PheValBzOC C2-Sym Phosphinic amide derivative (HOECHST AG)
Calanolide A; NSC675451
Calanolide B
Capravirine; S-1153
Castanospermine
CbzAF(CHOHCH2)AVVOMe
Cbz-Asn-Apns-Pro-NH-tBu; KNI-102
CGP 61755; Lasinavir
CGP 64222
CNI-H0294
Coactinon; I-EBU; HEPT derivative; MKC-442; Emivirine
Conocurvone; NSC650891
Coviracil; (−)FTC; (−)-2',3'-Dideoxy-5-fluoro-3'-thiacytidine; Emtricitabine; Emtriva
C-Oxetanocin-G; A-69992; (+−)Lobucavir; C-Oxt-G; Cyclobut-G; (+−)Cyclobut-G
Indinavir; MK639; L-735,524
Curdlan Sulfate
CV-N; Cyanovirin-N
Cyclic Urea Amide; SD146
Cyclosporin A
[Me-Ile-4]Cyclosporin A; SDZ NIM 811
D4A (L); L-2',3'-Didehydro-2',3'-dideoxyadenosine
D4FC; D-D4FC; 2',3'-Didehydro-2',3'-dideoxy-5-fluorocytidine; DPC 817
D4FC (L); L-2',3'-Didehydro-2',3'-dideoxy-5-fluorocytidine
D4G (L); L-2',3'-Didehydro-2',3'-dideoxyguanosine
D4I (L); L-2',3'-Didehydro-2',3'-dideoxyinosine
DABO
ddC; Dideoxycytidine; Zalcitabine
ddI; Dideoxyinosine; Didanosine
Dehydroepiandrosterone; DHEA; Prasterone; Dehydroisoandrosterone; EL-10
Dextran Sulfate
Dicaffeic acid ester; L-Chicoric acid
DMP-266; Efavirenz; Approved
DMP-323; XM-323
DMP-450
Docosanol; n-Docosanol
dOTC (−); (−)-2'-Deoxy-3'-oxa-4'-thiocytidine
dOTFC (−); (−)-2'-Deoxy-3'-oxa-4'-thio-5-fluorocytidine
DP-178; Pentafuside; T-20; GP41 127-162 AA; Enfuvirtide
E-BPTU; HEPT derivative; NSC 648400
E-EBU; HEPT derivative; MKC-442 derivative
E-EBU-dM; HEPT derivative; MKC-442 derivative
E-EPSeU; HEPT derivative; MKC-442 derivative
E-EPU; HEPT derivative; MKC-442 derivative
Ebselen
Etoposide
Epoxy steroid derivative; (4a,5a,17b)-17-Hydroxy-3-oxo-4,5-epoxyandrostane-2-carboxamide
Eulicin
Fenalamide A1; Phenalamide A1; Stipiamide
Fleephilone
Fluoroquinolone derivative; K-12
Saquinavir; Ro31-8959; Approved
Foscarnet; Phosphonoformic acid; Foscavir
FPMDAP
FPMPA
FPMPG
GPGRAF Octomer; SPC3
Hammerhead anti-gag RNA Ribozyme B
Harziphilone
HBY 097; Quinoxaline derivative
HEPT derivative; MKC-442 derivative
LY326188
HPMPA
HPMPDAP
HU; Hydroxyurea; Hydrea
Hydroxocobalamin
Hypericin
Ingenol 3,5,20-triacetate; ITA; RD3-2118
Ingenol derivative; RD4-2138
Inophyllum B
Inophyllum P
iQoa-Mta-Apns-Thz-NH-tBu; KNI-272
Isentress (Raltegravir)
IsoquinCON furanyl urethane analog
IsoquinCON thienyl urethane analog KNI-154; Noa-Asn-Apns-Thz-NH-tBu
KNI-174; Noa-Asn-Apns-Dmt-NH-tBu
KNI-227; Qoa-Mta-Apns-Thz-NH-tBu
L-685,434
L-685, 434-6-Hydroxy derivative
L-685,434-sOEtMorphderivative; L-689,502
L-685,434-OEtNMe2
L-685,434-OPrMorph derivative
L-697,593; 2-Pyridinone derivative
L-697,639; 2-Pyridinone derivative
L-697,661; 2-Pyridinone derivative
L-FddC; b-L-5F-ddC
Lamivudine & Zidovudine; 3TC & AZT; Approved
LY289612
LY289612 analog
LY-300046-HCl; PETT derivative; Trovirdine
LY314163; Saquinavir/Nelfinavir derivative
LY-73497; N-(2-Phenethyl)-N'-(2-thiazolyl)thiourea; PETT
MAP; Methyl acetylenic putrescine
Michellamine A; NSC650898
Michellamine B; NSC649324
Michellamine F
N-6-Et-ddA; N-Ethyl-2',3'-dideoxyadenosine
N-6-methyl ddA; N6-Methyl-2',3'-dideoxyadenosine
Naphthalene 2-sulphonate polymer; PRO2000
Nelfinavir-octahydro-thienopyridine analog
Nonoxynol 9
NSC625487; Thiazolobenzimidazole; TBZ
Oxathiin derivative; UC-38
Oxathiin derivative; UC-84
P9941
Penicillin Et(NH)2 Sym dimer
Penicillin G, ET(NH)2 derivative
Penicillin, 2Isoquin-OHPrNH2 analog
Pentosan Sulfate; Elmiron; SP54; Xylan Sulfate
PETT Cl, F derivative
PETT derivative
Phenoxan
Phorbol derivative; Prostratin
Platanic acid
PMEDAP
PMEG
PMEHx; PMEI
PMEMAP
PMET
PNU-140690; U-140690; Tipranavir
Pyridinone derivative
Quinoxalin2thione derivative; S-2720
R14458; TIBO derivative
R82150; TIBO derivative
R82913; TIBO derivative
Resobene
Ribavirin; Virazole
Ro 31-8959-bis-thf derivative
Saquinavir/Nelfinavir derivative
SB-205569; Val-Phe-Phe-HOCH2CH2 isostere analog
SC-52151; Telinavir
SDZ PRI 053
Suramin Sodium
T22
Thalidomide
Thiangazole; (−)-Thiangazole
Thiazoloisoindol-5-one
Thiazoloisoindol-5-one, derivative
Tle-Val-Sta, 5PhBuCOOH derivative; Statine derivative
UC-781
Val-Val-Sta, 5PhBuCOOH derivative; Statine derivative VB-11,328 and
Tenofovir Disoproxil.

27. A pharmaceutical composition according to claim 9 further comprising at least one additional compound selected from the group consisting of ACV; AK602; AMD070; APV; ATV; ATZ; AVX754 (apricitabine); AZT; Abacavir; Abacavir/Lamivudine/Zidovudine; Abacavir sulfate; Abacavir sulfate/Lamivudine; Abacavir/Lamivudine; Abelecet; Acyclovir; Adefovir dipivoxil; Adriamycin; Agenerase; Aldesleukin; Alovudine; Aluvia; AmBisome; Amdoxovir; Amphocin; Amphotec; Amphotericin B; Ampligen; Amprenavir; Androderm; Androgel; Apricitabine; Aptivus; Atazanavir; Atripla; Azithromycin; BMS-378806; BMS-488043; Bactrim; Baraclude; Bevirimat; Biaxin; Brecanavir; BufferGel; C31G; CD4-IgG2; CS; CV-N; Calanolide A; Calcium hydroxylapatite; Carbopol 974P; Carrageenan; Carraguard; Cellulose sulfate; Clarithromycin; Copegus; Cotrimoxazole; Crixivan; Cyanovirin-N; Cytovene; DAPD; DLV; DS; Darunavir; Delavirdine; Depo-Testosterone; Dextran sulfate; Didanosine; Diflucan; Doxil; Doxorubicin (liposomal); Dronabinol; EFV; Efavirenz; Elvucitabine; Emtricitabine; Emtricitabine; Tenofovir disoproxil fumarate; Emtriva; Enfufirtide; Entecavir; Epivir; Epoetin alfa; Epogen; Epzicom; Etopophos (phosphate salt); Etoposide; Etravirine; FTC; Fluconazole; Fortovase; Fosamprenavir; Foxivudine tidoxil; Fungizone; Fuzeon; GS 9137; GSK-873,140 (aplaviroc); GW433908; GW640385 (brecanavir); Ganciclovir; Globulin, Immune; Growth hormone (human); Hepsera; Hivid; Human growth hormone; IL-2; INH; Immune Globulin Intravenous (Human); Indinavir; Interferon alfa-2; Interleukin-2, recombinant human; Intron A (2b); Invirase; Isentress; Isoniazid; Itraconazole; KP-1461; Lamivudine/Zidovudine; Lexiva; Lopinavir/Ritonavir; MK-0518; Nebupent; Nelfinavir, Neutrexin; Nevirapine; Norvir; Nydrazid; Peptide T; PMPA Prodrug (Viread)' Prezista (Darunavir); PRO 140; PRO 2000; PRO 542 (CD4 IGg2); Procrit (Epoetin); Proleukin; Racivir; Radiesse; Rrebetol; Rescriptor; Retrovir; Reyataz; Ribavirin; Rifabutin; Rifadin; Rifampin; Rimactane; Ritonavir; Roferon-A (2a); Saquinavir; SCH-D (vicriviroc); Somatropin; Stavudinie; Sulfamethoxazole/Trimethoprim; Sustanon; Sustiva; TNX-355; Taxol; Tenofovir, Tenofovir disoproxil fumarate; Testosterone; Tipranavir; Toposar; Trimetrexate; Trizivir; Truvada (Erotriva and Viread combination); U-90152S (Delaviridine); UC-781; UK-427, 857 (maraviroc); Valcyte; Valganciclovir, Valproic acid; VePesid; Vicriviroc; Videx; Viracept (Tennofovir DF); Viramune; Virazole; Viread; Vitrasert; Zalcitabine; Zerit; Ziagen; Zidovudine; Zithromax; Zovirax, and mixtures thereof.

28. The composition according to claim 27 in oral or parenteral dosage form.

29. The composition according to claim 27 formulated for administration as an inhalation spray or a rectal suppository.

30. A method of treating an HIV infection in a patient, said method comprising administering to said patient an effective amount of a composition according to claim 27.

31. A method of reducing the likelihood of an HIV infection in a patient at risk of said infection, said method comprising administering to said patient an effective amount of a composition according to claim 27 to said patient.

32. A method of treating a patient with AIDS or ARC comprising administering to said patient a therapeutically effective amount of a composition according to claim 27.

33. A method of inhibiting HIV integrase in a subject, said method comprising administering to said subject a therapeutically effective amount of a composition according to claim 27.

34. The method according to claim 30 wherein said patient or subject is a human.

35. A method of treating an HIV infection in a human host comprising administering to said host in combination, an effective amount of a first compound according to the structure:

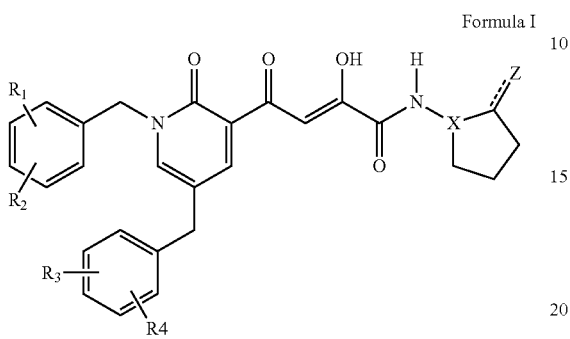

Formula I where R₁=o-F, R₂=H, R₃=p-F, R₄=o-F
R₁=p-F, R₂=H, R₃=p-F, R₄=o-F
R₁=o-F, R₂=o-F, R₃=o-F, R₄=H
R₁=o-F, R₂=H, R₃=o-F, R₄=o-F
R₁=o-F, R₂=H, R₃=p-F, R₄=H
R₁=o-F, R₂=p-F, R₃=p-F, R₄=o-F, or
R₁=o-F, R₂=o-F, R₃=o-F, R₄=o-F
X is CH or N; and
Z is OH or =O; in combination with an effective amount at least one additional agent set forth below:
    (−)bDioxolane-G; DXG
    (−)b-Arctigenin; Arctigenin
    (−)-Carbovir; (−)—C-D4G; (−)-Carbovir
    (−)-b-D-2,6-Diaminopurine dioxolane; Amdoxovir; DAPD; APD
    (+)-2'-Deoxy-3'-oxa-4'-thiocytidine; dOTC (+)
    (+)-2'-Deoxy-3'-oxa-4'-thio-5-fluorocytidine; dOTFC (+)
    (+/−)-Cyclobut-G; A-69992; (+/−)-Lobucavir; C-Oxt-G; Cyclobut-G; C-Oxetanocin-G
    (R)-2QuinCOAsnPhe[CHOHCH2]PipCONHtBu
    (R)-3,6-Diamino-N-(aminomethyl)hexanamide; Bellenamine
    (R)-PMPA; (R)-9-(2-Phosphonylmethoxypropyl)adenine; PMPA-(R); Tenofovir
    (R)-PMPDAP; PMPDAP-(R)
    (S)-PMPA; (S)-9-(2-Phosphonylmethoxypropyl)adenine; PMPA(S)
    (S)-9-(2-Phosphonylmethoxypropyl)adenine; (S)-PMPA
    a-APA; R89439; Loviride
    a-APA derivative; R87232
    a-APA derivative; R88703
    a-APA enantiomer; R90385
    a-L-AZT; AZT-a-L
    a-L-DXC; a-L-Dioxalane-C; DXC-a-L-
    a-L-FTC; FTC-a-L-
    a-Monofluoromethyldehydroornithine methyl ester; MFMOME
    1,1'-Azobisformamide; ADA; Azodicarbonamide
    1-(11-Octylamino-10-hydroxyundecyl)-3,7-dimethylxanthine; CT-2576
    1-(2',3'-Dideoxy-2'-fluoro-b-D-threo-pentofuranosyl)cytosine; Ro 31-6840
    1-(2'-Fluoro-2',3'-dideoxy-B-D-erythro-pentofuranosyl) thymine; 2'FddT
    1-(2OHPr)-4-Substit-piperazine, thienyl carbamate derivative
    1-(2OHPr)-4-Substit-piperazine, thienyl carbamate derivative
    1-(2OHPr)-4-Substit-piperazine, thienyl carbamate derivative
    1-(2OHPr)-4-Substit-piperazine, thienyl carbamate derivative
    1-[(2-Hydroxyethoxy)methyl]-6-(3-methylphenyl)thio) thymine; HEPT-M
    1-[(2-Hydroxyethoxy)methyl]-6-(phenylthio)-2-thiothymine; HEPT-S
    1-[(2-Hydroxyethoxy)methyl]-6-(phenylthio)thymine; HEPT
    1-Deoxynojirimycin; Deoxynojirimycin
    141W94; VX-478; Amprenavir
    1592U89 Succinate; Abacavir Succinate
    1-Aminooxyethylamine; AEA
    1-Methoxyoxalyl-3,5-dicaffeoylquinic acid; 1-MO-3,5-DCQA; Dicaffeoylquinic acid derivative
    1OH-2(Cbz-Tle)₃PhPr [14]paracyclophane derivative
    1OH-2(Cbz-ValNH)₃PhPr [13]metacyclophane derivative
    1OH-2(Cbz-ValNH)₃PhPr [13]paracyclophane derivative
    1OH-2(Cbz-ValNH)₃PhPr [14]paracyclophane derivative
    1OH-2(Cbz-ValNH)₃PhPr [17]paracyclophane derivative
    12-Deoxyphorbol-[3-(3E,5E-decadienoate); Phorbol derivative
    16-alpha-Bromoepiandrosterone; Epi-Br; Inactivin; HE2000; PPB2; DHEA derivative
    1-b-D-arabinofuranosyl-5-(2-bromovinyl)uracil; BV-ara-U; BVaraU; BV ara-U; Sorivudine; SQ-32756; Bravavir; Brovavir; Usevir; YN-72; Bromovinyl araU; BVAU
    2',3'-Didehydro-3'-deoxycytidine; D4C
    2',3'-Dideoxydidehydroguanosine; D4G
    2',3'-Didehydro-3'-deoxythymidine; D4T; Stavudine
    2',3'-Dideoxy-3'-fluoro-4-thiothymidine; 3'-F-4-Thio-ddT
    2',3'-Dideoxy-3'-fluoro-5-bromouridine; FddBrU
    2',3'-Dideoxy-3'-fluoro-5-chlorocytidine; 3'-F-5-Cl-ddC
    2',3'-Dideoxy-3'-fluoro-5-chlorouridine; 935U83; 5-Chloro-2',3'-dideoxy-3'-fluorouridine; FddClU; Raluridine
    2',3'-Dideoxy-5-ethylcytidine; 5-Et-ddC
    2',3'-D1deoxyadenosine; D2A; ddAdo; ddA
    2',3'-Dideoxydidehydroadenosine; d4A
    2',3'-D1deoxyguanosine; D2G; ddG
    2',3'-Dideoxy-3'-hydroxymethyl cytidine; 3'-Hydroxymethyl-ddC; BEA-005
    2,5'-Anhydro-3'-azido-2',3'-dideoxyuridine; AZU-2,5'-anhydro
    2,5'-Anhydro-3'-azido-3'-deoxythymidine; AZT-2,5'-anhydro
    2',5'diSilySpiroT; TSAO-T; 2',5'diSilySpiroT; TSAO-meˆ3T
    2,6-Diamino-2',3'-dideoxypurine-9-ribofuranoside; ddDAPR; DAPDDR; 2,6-Diamino-ddP
    2,6-Diaminopurine-2',3'-dideoxydidehydroriboside; ddeDAPR
    2,6-Diaminopurine-3'-fluoro-2',3'-dideoxyriboside; 3'-F-ddDAPR
    2-Aminobenzylstatine Valyl Cbz derivative; Statine derivative
    2-Glycine amide-5-chlorophenyl 2-pyrryl ketone; GCPK
    [2-PyridCH2NCH3CO-Val-NHCH(Bz)]CHOHCHOH; A-77003

2'-Azido-2',3'-dideoxyadenosine; 9-(2'-Azido-2',3'-dideoxy-B-D-erythropentofuranosyl)adenine; 2'-N3ddA
2'-FddA(B-D-threo); F-ddA; 2'-F-dd-ara-A; 9-(2'-Fluoro-2',3'-dideoxy-B-D-threopentafuranosyl)adenine; Lodensine
2'-N3ddA (B-D-threo); 9-(2'-Azido-2',3'-dideoxy-b-threopentafuranosyl)adenine
2-NaphCOAsnPhe[CHOHCH2]Pro-OtBu
2-Nitrophenylphenylsulfone; NPPS
3-(3-Oxo-1-propenyl)-3'-azido-3'-deoxythymidine; 3-(3-Oxo-1-propenyl)AZT
3-(Phenylsulfonyl)-indole derivative; L-737,126
3,5-DCQA; 3,5-Dicaffeoylquinic acid; Dicaffeoylquinic acid
3'-Azido-2',3'-dideoxy-5-[(cyanomethyl)oxy]uridine; 3'-N3-5-Cyanomethyloxy-ddU
3'-Azido-2',3'-dideoxy-5-aminouridine; 3'-N3-5-NH2-ddU
3'-Azido-2',3'-dideoxy-5-aza-6-deazauridine; C-analog of 3'-N3-ddU
3'-Azido-2',3'-dideoxy-5-bromouridine; 3'-N3-5-Br-ddU; AZddBrU
3'-Azido-2',3'-dideoxy-5-chlorocytidine; 3'-Az-5-Cl-ddC
3'-Azido-2',3'-dideoxy-5-dimethylaminouridine; 3'-N3-5-NMe2-ddU
3'-Azido-2',3'-dideoxy-5-ethyluridine; 3'-N3-5-EtddU; CS-85; AZddEtU
3'-Azido-2',3'-dideoxy-5-fluorocytidine; 3'-N3-5-F-ddC
3'-Azido-2',3'-dideoxy-5-fluorouridine; AZddFU
3'-Azido-2',3'-dideoxy-5-hydroxyuridine; 3'-N3-5-OH-ddU
3'-Azido-2',3'-dideoxy-5-iodouridine; 3'-N3-5-1-ddU; AZddIU
3'-Azido-2',3'-dideoxy-5-methyaminouridine; 3'-N3-5-NHMe-ddU
3'-Azido-2',3'-dideoxy-5-methylcytidine; CS-92; 3'-N3-5-Me-ddC
3'-Azido-2',3'-dideoxy-5-thiocyanatouridine; 3'-N3-5-SCN-ddU
3'-Azido-2',3'-dideoxy-5-trifluoromethyluridine; 3'-N3-5-CF3-ddU
3'-Azido-2',3'-dideoxycytidine; CS-91; 3'-N3-ddC
3'-Azido-2',3'-dideoxyguanosine; AZG; 3'-N3ddG
3'-Azido-2',3'-dideoxy-N4-5-dimethylcytidine; 3'-N3-N4-5-diMe-ddC
3'-Azido-2',3'-dideoxy-N4-OH-5-methylcytidine; 3'-N3-N4-OH-5-Me-ddC
3'-Azido-2',3'-dideoxyuridine; CS-87; 3'-N3ddU; AZdU; Uravidine
3'-Azido-3'-deoxy-6-azathymidine; 3'AZ-6AzaT
3-Azido-3'-deoxythymidilyl-(5',5)-2',3'-dideoxy-5'-adenylic acid; AZT-P-ddA
3'-Azido-3'-deoxythymidilyl-(5',5)-2',3'-dideoxy-5'-adenylic acid, 2-cyanoethyl ester; AZT-P(CyE)-ddA
3'-Azido-3'-deoxythymidilyl-(5',5)-2',3'-dideoxy-5'-inosinic acid; AZT-P-ddI
3'-Azido-3'-deoxythymidine-5'-(butylmethoxyvalinyl) phosphate; 5'MeOValPO3(Bu)AZT
3'-Azido-5-chloro-2',3'-dideoxyuridine; AzddClUrd; Azd-dClU
3'-Deoxythymidine; ddT
3'-FddA (B-D-Erythro); 9-(3'-Fluoro-2',3'-dideoxy-B-D-erythropentafuranosyl)adenine
3'-FddC; 3'-Fluoro-2',3'-dideoxycytidine
3'-FddG; 3'-Fluoro-2',3'-dideoxyguanosine
3'-FddT; Alovudine; FddT; FddThD; 3'-FLT; FLT
3'-FddU; 3'-Fluoro-2',3'-dideoxyuridine
3'-Fluoro-2',3'-dideoxy-5-iodouridine; FddIU
3'-N3-ddA; 9-(3'-Azido-2',3'-dideoxy-B-D-erythropentafuranosyl)adenine
3TC; Lamivudine
Lamivudine & Zidovudine
4'-Acetoamidophenyl-4-guadinobenzoate; AGB
4'-Az-3'-dT; 4'-Azido-3'-deoxythymidine
4'-Az-5CldU; 4'-Azido-5-chloro-2'-deoxyuridine
4'-AzdA; 4'-Azido-2'-deoxyadenosine
4'-AzdC; 4'-Azido-2'-deoxycytidine
4'-AzdG; 4'-Azido-2'-deoxyguanosine
4'-AzdI; 4'-Azido-2'-deoxyinosine
4'-AzdU; 4'-Azido-2'-deoxyuridine
4'-Azido-2'-deoxy-b-D-erythro-pentofuranosyl-5-methyl-2,4-dioxopyrimidine; 4'-Azidothymidine
4'-Cyanothymidine; 4'-CN-T
4-Methyl-5-(pyrazinyl)-3H-1,2-dithiole-3-thione; Oltipraz
5'-[(1,4-Dihydro-1-methyl-3-pyridinylcarbonyl)oxy]-3'-azido-2',3'-deoxythymidine; DP-AZT; HP-AZT; AZT Prodrug; AZT-DHP
5'-[[(Z)-4-amino-2-butenyl]methylamino]-5'-deoxyadenosine; MDL 73811
5'-Alkylglycosidecarbonate of 3'-azido-3'-deoxythymidine; AcNHGlc-hexyl-CO3 AZT
5Cl3PhS-2IndolCONH2
5-Fluoro-2',3'-dideoxycytidine; 5-F-ddC
5-Methyl-3'-azido-2',3'-dideoxyisocytidine; MeAZddIsoC
6-O-Butanoylcastanospermine; BuCast; MDL 28,574; Celgosivir
6-Chloro-9-(2,3-dideoxy-b-D-glyceropentofuranosyl)-9H-purine; D2ClP; 6-Chloro-ddP; CPDDR; 6Cl-ddP
6-Dimethylaminopurine-2',3'-dideoxyriboside; N-6-dimethylddA; DMAPDDR
7-Chloro-N-methyl-5-(1H-pyrrol-2-yl)-3H-1,4-benzodiazepin-2-amine; Ro 24-7429
7-Chloro-5-(2-pyrryl)-3H-1,4-benzodiazepin-2(H)-one; Ro 5-3335
8-Chloro-TIBO; Tivirapine; R86183
9-(2,3-Dideoxy-b-D-ribofuranosyl)-6-(methylthio)purine; D2SMeP
9-[Bis(OHMe)cBu]A; A-69463; Cyclobutyl-A; Cyclobut-A; C-oxetanocin A
A-76890
A-77212
A-80987; Ritonavir derivative
A-81525; Ritonavir derivative
A-83962; Ritonavir derivative
A-98881; Azacyclic urea derivative
AA; L-ascorbic acid; Calcium Ascorbate
AAP-BHAP; U-104489; PNU-104489
Abacavir & Lamivudine & Zidovudine
ABT-378; Lopinavir
ABT-378 & ABT-538; Lopinavir & Ritonavir
ABT-538; Ritonavir
Acemannan
Adefovir; PMEA; GS-0393
Adefovir dipivoxil; BisPom PMEA; GS-840
AG-1343; Nelfinavir
AG1350; LY316957; Nelfinavir-octahydro-thienopyridine analog
AHPBA analog; R-87366
Alpha-lipoic acid; a-Lipoic acid; Thioctic acid
ALX40-4C
AMD3100; JM3100

Amprenavir phosphate; VX-175; GW433908; GW433908A (*Sodium Salt*); GW433908G (*Calcium Salt*); Fosamprenavir
Ancer 20; Z-100
Anti-sense 25-mer phosphorothioate; GEM91
Atazanavir; CGP-73547; BMS-232632; BMS 232632; Zrivada; Latazanavir
Atevirdine; U-87201E; BHAP derivative
Aurintricarboxylic acid; Dupont ATA; Dupont DA639; SD-095345; ATA
AY 9944; trans-1,4-Bis(2-dichlorobenzylaminoethyl)cyclohexane dichlorhydrate
AZT; Zidovudine; Azidothymidine
AZT-PO3(CH3)-AZT; O,O'-Bis(3'-azido-3'-deoxythymidin-5'-yl)methylphosphonate
Baicalin; TJN-151
Betulinic acid; Mairin
Betulinic acid, 3-O-(3',3'-dimethylsuccinate)
BHAP derivative
Delavirdine; U-90152
U-88204E
BI-RG-587; Nevirapine
BILA 1906 BS
BILA 2011 BS; Palinavir
BILA 2185 BS
Bis(2-nitrophenyl)sulfone; Bis(2NO2Ph)SO2; NSC633001
bis-ValHOEt-N2aza-peptide isostere; CGP 53820
bis-ValHOEt-N2aza-peptide isostere; CGP 53820 analog
BMS-186318
BocPhe[CHOH(CH2)3CH=CHPhCO]IleAMBI; L-687, 908
BzOCValPhe[diCHOH(RR)]PheValBzOC
BzOCValPhe[diCHOH(SS)]PheValBzOC C2-Sym Phosphinic amide derivative (HOECHST AG)
Calanolide A; NSC675451
Calanolide B
Capravirine; S-1153
Castanospermine
CbzAF(CHOHCH2)AVVOMe
Cbz-Asn-Apns-Pro-NH-tBu; KNI-102
CGP 61755; Lasinavir
CGP 64222
CNI-H0294
Coactinon; I-EBU; HEPT derivative; MKC-442; Emivirine
Conocurvone; NSC650891
Coviracil; (−)FTC; (−)-2',3'-Dideoxy-5-fluoro-3'-thiacytidine; Emtricitabine; Emtriva
C-Oxetanocin-G; A-69992; (+−)Lobucavir; C-Oxt-G; Cyclobut-G; (+−)Cyclobut-G
Indinavir; MK639; L-735,524
Curdlan Sulfate
CV-N; Cyanovirin-N
Cyclic Urea Amide; SD146
Cyclosporin A
[Me-Ile-4]Cyclosporin A; SDZ NIM 811
D4A (L); L-2',3'-Didehydro-2',3'-dideoxyadenosine
D4FC; D-D4FC; 2',3'-Didehydro-2',3'-dideoxy-5-fluorocytidine; DPC 817
D4FC (L); L-2',3'-Didehydro-2',3'-dideoxy-5-fluorocytidine
D4G (L); L-2',3'-Didehydro-2',3'-dideoxyguanosine
D4I (L); L-2',3'-Didehydro-2',3'-dideoxyinosine
DABO
ddC; Dideoxycytidine; Zalcitabine
ddI; Dideoxyinosine; Didanosine
Dehydroepiandrosterone; DHEA; Prasterone; Dehydroisoandrosterone; EL-10
Dextran Sulfate
Dicaffeic acid ester; L-Chicoric acid
DMP-266; Efavirenz; Approved
DMP-323; XM-323
DMP-450
Docosanol; n-Docosanol
dOTC (−); (−)-2'-Deoxy-3'-oxa-4'-thiocytidine
dOTFC (−); (−)-2'-Deoxy-3'-oxa-4'-thio-5-fluorocytidine
DP-178; Pentafuside; T-20; GP41 127-162 AA; Enfuvirtide
E-BPTU; HEPT derivative; NSC 648400
E-EBU; HEPT derivative; MKC-442 derivative
E-EBU-dM; HEPT derivative; MKC-442 derivative
E-EPSeU; HEPT derivative; MKC-442 derivative
E-EPU; HEPT derivative; MKC-442 derivative
Ebselen
Etoposide
Epoxy steroid derivative; (4a,5a,17b)-17-Hydroxy-3-oxo-4,5-epoxyandrostane-2-carboxamide
Eulicin
Fenalamide A1; Phenalamide A1; Stipiamide
Fleephilone
Fluoroquinolone derivative; K-12
Saquinavir; Ro31-8959; Approved
Foscarnet; Phosphonoformic acid; Foscavir
FPMDAP
FPMPA
FPMPG
GPGRAF Octomer; SPC3
Hammerhead anti-gag RNA Ribozyme B
Harziphilone
HBY 097; Quinoxaline derivative
HEPT derivative; MKC-442 derivative
LY326188
HPMPA
HPMPDAP
HU; Hydroxyurea; Hydrea
Hydroxocobalamin
Hypericin
Ingenol 3,5,20-triacetate; ITA; RD3-2118
Ingenol derivative; RD4-2138
Inophyllum B
Inophyllum P
iQoa-Mta-Apns-Thz-NH-tBu; KNI-272
Isentress (Raltegravir)
IsoquinCON furanyl urethane analog
IsoquinCON thienyl urethane analog
KNI-154; Noa-Asn-Apns-Thz-NH-tBu
KNI-174; Noa-Asn-Apns-Dmt-NH-tBu
KNI-227; Qoa-Mta-Apns-Thz-NH-tBu
L-685,434
L-685, 434-6-Hydroxy derivative
L-685,434-sOEtMorphderivative; L-689,502
L-685,434-OEtNMe2
L-685,434-OPrMorph derivative
L-697,593; 2-Pyridinone derivative
L-697,639; 2-Pyridinone derivative
L-697,661; 2-Pyridinone derivative
L-FddC; b-L-5F-ddC
Lamivudine & Zidovudine; 3TC & AZT; Approved
LY289612
LY289612 analog
LY-300046-HCl; PETT derivative; Trovirdine
LY314163; Saquinavir/Nelfinavir derivative LY-73497; N-(2-Phenethyl)-N'-(2-thiazolyl)thiourea; PETT
MAP; Methyl acetylenic putrescine
Michellamine A; NSC650898
Michellamine B; NSC649324
Michellamine F
N-6-Et-ddA; N-Ethyl-2',3'-dideoxyadenosine
N-6-methyl ddA; N6-Methyl-2',3'-dideoxyadenosine
Naphthalene 2-sulphonate polymer; PRO2000
Nelfinavir-octahydro-thienopyridine analog
Nonoxynol 9
NSC625487; Thiazolobenzimidazole; TBZ
Oxathiin derivative; UC-38
Oxathiin derivative; UC-84
P9941
Penicillin Et(NH)2 Sym dimer
Penicillin G, ET(NH)2 derivative
Penicillin, 2Isoquin-OHPrNH2 analog
Pentosan Sulfate; Elmiron; SP54; Xylan Sulfate
PETT Cl, F derivative
PETT derivative
Phenoxan
Phorbol derivative; Prostratin
Platanic acid
PMEDAP
PMEG
PMEHx; PMEI
PMEMAP
PMET
PNU-140690; U-140690; Tipranavir
Pyridinone derivative
Quinoxalin2thione derivate; S-2720
R14458; TIBO derivative
R82150; TIBO derivative
R82913; TIBO derivative
Resobene
Ribavirin; Virazole
Ro 31-8959-bis-thf derivative
Saquinavir/Nelfinavir derivative
SB-205569; Val-Phe-Phe-HOCH2CH2 isostere analog
SC-52151; Telinavir
SDZ PRI 053
Suramin Sodium
T22
Thalidomide
Thiangazole; (-)-Thiangazole
Thiazoloisoindol-5-one
Thiazoloisoindol-5-one, derivative
Tle-Val-Sta, 5PhBuCOOH derivative; Statine derivative
UC-781
Val-Val-Sta, 5PhBuCOOH derivative; Statine derivative
VB-11,328 and
Tenofovir Disoproxil
and mixtures thereof.

36. A method according to claim 35, wherein said first compound is

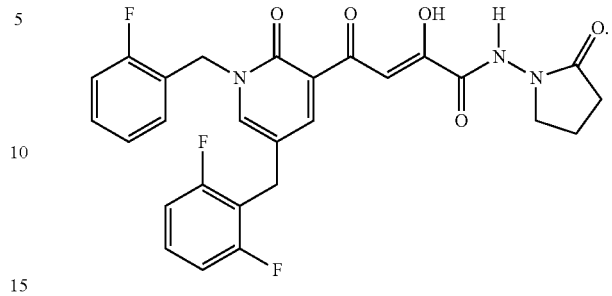

37. A method of treating an HIV infection in a human host comprising administering to said host in combination, an effective amount of a first compound according to the structure:

Formula I

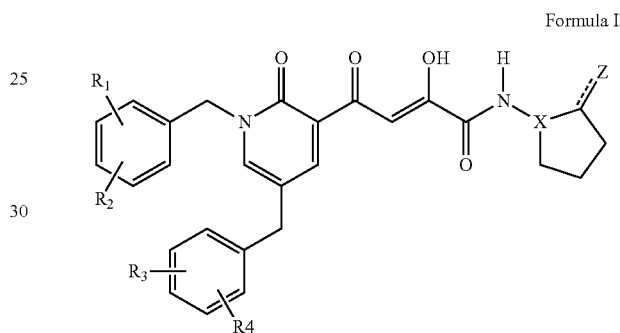

Where $R_1$=o-F, $R_2$=H, $R_3$=p-F, $R_4$=o-F
$R_1$=p-F, $R_2$=H, $R_3$=p-F, $R_4$=o-F
$R_1$=o-F, $R_2$=o-F, $R_3$=o-F, $R_4$=H
$R_1$=o-F, $R_2$=H, $R_3$=o-F, $R_4$=o-F
$R_1$=o-F, $R_2$=H, $R_3$=p-F, $R_4$=H
$R_1$=o-F, $R_2$=p-F, $R_3$ p-F, $R_4$=o-F or
$R_1$=o-F, $R_2$=o-F, $R_3$=o-F, $R_4$=o-F;
X is CH or N; and
Z is OH or =O;
or a pharmaceutically acceptable salts thereof, in combination with at least one additional compound selected from the group consisting of ACV; AK602; AMD070; APV; ATV; ATZ; AVX754 (apricitabine); AZT; Abacavir; Abacavir/Lamivudine/Zidovudine; Abacavir sulfate; Abacavir sulfate/Lamivudine; Abacavir/Lamivudine; Abelecet; Acyclovir; Adefovir dipivoxil; Adriamycin; Agenerase; Aldesleukin; Alovudine; Aluvia; AmBisome; Amdoxovir; Amphocin; Amphotec; Amphotericin B; Ampligen; Amprenavir; Androderm; Androgel; Apricitabine; Aptivus; Atazanavir; Atripla; Azithromycin; BMS-378806; BMS-488043; Bactrim; Baraclude; Bevirimat; Biaxin; Brecanavir; BufferGel; C31G; CD4-IgG2; CS; CV-N; Calanolide A; Calcium hydroxylapatite; Carbopol 974P; Carrageenan; Carraguard; Cellulose sulfate; Clarithromycin; Copegus; Cotrimoxazole; Crixivan; Cyanovirin-N; Cytovene; DLV; DS; Darunavir; Delavirdine; Depo-Testosterone; Dextran sulfate; Didanosine; Diflucan; Doxil; Doxorubicin (liposomal); Dronabinol; UV; Efavirenz; Elvucitabine; Emtricitabine; Emtricitabine; Tenofovir disoproxil fumarate; Emtriva; Enfufirtide; Entecavir, Epivir; Epoetin alfa; Epogen; Epzicom; Etopophos (phosphate salt); Etoposide; Etravirine; FTC; Fluconazole; Fortovase;

Fosamprenavir; Foxivudine tidoxil; Fungizone; Fuzeon; GS 9137; GSK-873,140 (aplaviroc); GW433908; GW640385 (brecanavir); Ganciclovir, Globulin, Immune; Growth hormone (human); Hepsera; Hivid; Human growth hormone; IL-2; INH; Immune Globulin Intravenous (Human); Indinavir; Interferon alfa-2; Interleukin-2, recombinant human; Intron A (2b); Invirase; Isentress; Isoniazid; Itraconazole; KP-1461; Lamivudine/Zidovudine; Lexiva; Lopinavir/Ritonavir; MK-0518; Nebupent; Nelfinavir; Neutrexin; Nevirapine; Norvir; Nydrazid; Peptide T; PMPA Prodrug (Viread)' Prezista (Darunavir); PRO 140; PRO 2000; PRO 542 (CD4 IGg2); Procrit (Epoetin); Proleukin; Racivir; Radiesse; Rrebetol; Rescriptor, Retrovir, Reyataz; Ribavirin; Rifabutin; Rifadin; Rifampin; Rimactane; Ritonavir, Roferon-A (2a); Saquinavir, SCH-D (vicriviroc); Somatropin; Stavudinie; Sulfamethoxazole/Trimethoprim; Sustanon; Sustiva; TNX-355; Taxol; Tenofovir; Tenofovir disoproxil fumarate; Testosterone; Tipranavir; Toposar; Trimetrexate; Trizivir, Truvada (Emtriva and Viread combination); U-90152S (Delaviridine); UC-781; UK-427,857 (maraviroc); Valcyte; Valganciclovir; Valproic acid; VePesid; Vicriviroc; Videx; Viracept (Tennofovir DF); Viramune; Virazole; Viread; Vitrasert; Zalcitabine; Zerit; Ziagen; Zidovudine; Zithromax; Zovirax and mixtures thereof, further in combination with a pharmaceutically acceptable carrier, additive or excipient.

38. A method according to claim 37 wherein the first compound is

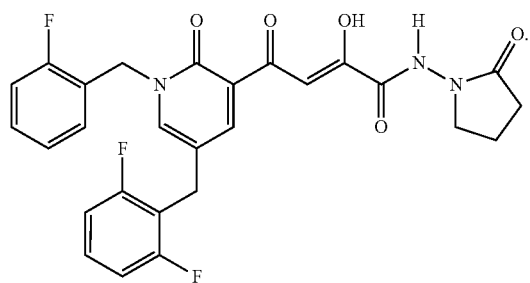 [SMILES: O=C(NN1CCCC1=O)/C(O)=C/C(=O)c1cc(Cc2c(F)cccc2F)cn(Cc2ccccc2F)c1=O]

39. The compound:
(1S,2S)-4-(5-(2,4-difluorobenzyl)-1-(2-fluorobenzyl)-2-oxo-1,2-dihydropyridin-3-yl)-2-hydroxy-N-(2-hydroxycyclopentyl)-4-oxobut-2-enamide
(1R,2R)-4-(5-(2,4-difluorobenzyl)-1-(2-fluorobenzyl)-2-oxo-1,2-dihydropyridin-3-yl)-2-hydroxy-N-(2-hydroxycyclopentyl)-4-oxobut-2-enamide
4-(5-(2,4-difluorobenzyl)-1-(2-fluorobenzyl)-2-oxo-1,2-dihydropyridin-3-yl)-2-hydroxy-4-oxo-N-(2-oxopyrrolidin-1-yl)but-2-enamide
(1S,2S)-4-(5-(2,4-difluorobenzyl)-1-(4-fluorobenzyl)-2-oxo-1,2-dihydropyridin-3-yl)-2-hydroxy-N-(2-hydroxycyclopentyl)-4-oxobut-2-enamide
(1R,2R)-4-(5-(2,4-difluorobenzyl)-1-(4-fluorobenzyl)-2-oxo-1,2-dihydropyridin-3-yl)-2-hydroxy-N-(2-hydroxycyclopentyl)-4-oxobut-2-enamide
4-(5-(2,4-difluorobenzyl)-1-(4-fluorobenzyl)-2-oxo-1,2-dihydropyridin-3-yl)-2-hydroxy-4-oxo-N-(2-oxopyrrolidin-1-yl)but-2-enamide
(1S,2S)-4-(1-(2-fluorobenzyl)-5-(4-fluorobenzyl)-2-oxo-1,2-dihydropyridin-3-yl)-2-hydroxy-N-(2-hydroxycyclopentyl)-4-oxobut-2-enamide
(1R,2R)-4-(1-(2-fluorobenzyl)-5-(4-fluorobenzyl)-2-oxo-1,2-dihydropyridin-3-yl)-2-hydroxy-N-(2-hydroxycyclopentyl)-4-oxobut-2-enamide
4-(1-(2-fluorobenzyl)-5-(4-fluorobenzyl)-2-oxo-1,2-dihydropyridin-3-yl)-2-hydroxy-4-oxo-N-(2-oxopyrrolidin-1-yl)but-2-enamide
(1S,2S)-4-(1-(2,6-difluorobenzyl)-5-(2-fluorobenzyl)-2-oxo-1,2-dihydropyridin-3-yl)-2-hydroxy-N-(2-hydroxycyclopentyl)-4-oxobut-2-enamide
(1R,2R)-4-(1-(2,6-difluorobenzyl)-5-(2-fluorobenzyl)-2-oxo-1,2-dihydropyridin-3-yl)-2-hydroxy-N-(2-hydroxycyclopentyl)-4-oxobut-2-enamide
4-(1-(2,6-difluorobenzyl)-5-(2-fluorobenzyl)-2-oxo-1,2-dihydropyridin-3-yl)-2-hydroxy-4-oxo-N-(2-oxopyrrolidin-1-yl)but-2-enamide
(1S,2S)-4-(1,5-bis(2,4-difluorobenzyl)-2-oxo-1,2-dihydropyridin-3-yl)-2-hydroxy-N-(2-hydroxycyclopentyl)-4-oxobut-2-enamide
(1R,2R)-4-(1,5-bis(2,4-difluorobenzyl)-2-oxo-1,2-dihydropyridin-3-yl)-2-hydroxy-N-(2-hydroxycyclopentyl)-4-oxobut-2-enamide
4-(1,5-bis(2,4-difluorobenzyl)-2-oxo-1,2-dihydropyridin-3-yl)-2-hydroxy-4-oxo-N-(2-oxopyrrolidin-1-yl)but-2-enamide
(1S,2S)-4-(5-(2,6-difluorobenzyl)-1-(2-fluorobenzyl)-2-oxo-1,2-dihydropyridin-3-yl)-2-hydroxy-N-(2-hydroxycyclopentyl)-4-oxobut-2-enamide
(1R,2R)-4-(5-(2,6-difluorobenzyl)-1-(2-fluorobenzyl)-2-oxo-1,2-dihydropyridin-3-yl)-2-hydroxy-N-(2-hydroxycyclopentyl)-4-oxobut-2-enamide
4-(5-(2,6-difluorobenzyl)-1-(2-fluorobenzyl)-2-oxo-1,2-dihydropyridin-3-yl)-2-hydroxy-4-oxo-N-(2-oxopyrrolidin-1-yl)but-2-enamide
(1S,2S)-4-(1,5-bis(2,6-difluorobenzyl)-2-oxo-1,2-dihydropyridin-3-yl)-2-hydroxy-N-(2-hydroxycyclopentyl)-4-oxobut-2-enamide
(1R,2R)-4-(1,5-bis(2,6-difluorobenzyl)-2-oxo-1,2-dihydropyridin-3-yl)-2-hydroxy-N-(2-hydroxycyclopentyl)-4-oxobut-2-enamide, or
4-(1,5-bis(2,6-difluorobenzyl)-2-oxo-1,2-6 hydropyridin-3-yl)-2-hydroxy-4-oxo-N-(2-oxopyrrolidin-1-yl)but-2-enamide.

40. A pharmaceutical composition comprising a compound according to claim 39 in combination with a pharmaceutically acceptable carrier, additive or excipient.

41. The composition according to claim 40 in oral or parenteral dosage form.

42. A kit comprising a pharmaceutical composition according to claim 11 and instructions for a medical professional and/or a patient on how to administer said composition.

43. The method according to claim 31 wherein said patient or subject is a human.

44. The method according to claim 32 wherein said patient or subject is a human.

45. The method according to claim 33 wherein said patient or subject is a human.

* * * * *

UNITED STATES PATENT AND TRADEMARK OFFICE
CERTIFICATE OF CORRECTION

| | | |
|---|---|---|
| PATENT NO. | : 8,703,801 B2 | Page 1 of 1 |
| APPLICATION NO. | : 13/513448 | |
| DATED | : April 22, 2014 | |
| INVENTOR(S) | : Vasu Nair et al. | |

It is certified that error appears in the above-identified patent and that said Letters Patent is hereby corrected as shown below:

In the Specification

Under Related Applications and Government Support, the second paragraph currently reads:
The present invention was made with government support under Grant Number RO1 AI 43181 of the National Institutes of Health. Consequently, the government retains rights in the invention.

Replace current paragraph with the following:
This invention was made with government support under Agreement Nos. AI043181 and RR016621 awarded by the NIH. The Government has certain rights in the invention. (37CFR 401.14 f(4))

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*